United States Patent
Goetz et al.

(10) Patent No.: US 11,186,874 B2
(45) Date of Patent: Nov. 30, 2021

(54) ERK1 AND ERK2 MUTATIONS THAT CONFER RESISTANCE TO MAPK PATHWAY INHIBITORS

(71) Applicant: Dana-Farber Cancer Institute, Inc., Boston, MA (US)

(72) Inventors: Eva M. Goetz, Salem, MA (US); Levi A. Garraway, Newton, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 461 days.

(21) Appl. No.: 15/373,173

(22) PCT Filed: Jun. 11, 2015

(86) PCT No.: PCT/US2015/035337
§ 371 (c)(1),
(2) Date: Dec. 8, 2016

(87) PCT Pub. No.: WO2015/191857
PCT Pub. Date: Dec. 17, 2015

(65) Prior Publication Data
US 2017/0268065 A1 Sep. 21, 2017

Related U.S. Application Data

(60) Provisional application No. 62/012,175, filed on Jun. 13, 2014.

(51) Int. Cl.
*C12Q 1/6886* (2018.01)

(52) U.S. Cl.
CPC ..... *C12Q 1/6886* (2013.01); *C12Q 2600/106* (2013.01); *C12Q 2600/156* (2013.01)

(58) Field of Classification Search
None
See application file for complete search history.

(56) References Cited

FOREIGN PATENT DOCUMENTS

WO WO-2009/073513 A1 6/2009
WO WO-2011/156588 A1 12/2011

OTHER PUBLICATIONS

Dulak et al Nature Genetics.Mar. 4, 2013. 45(5): 478-486 and Online Methods, 2 pages.*
Camps et al., "Catalytic Activation of the Phosphatase MKP-3 by ERK2 Mitogen-Activated Protein Kinase", Science, 280(5367): 1262-1265 (1998).
Goetz et al., "ERK Mutations Confer Resistance to Mitogen-Activated Protein Kinase Pathway Inhibitors," Cancer Research, 74(23): 7079-7089 (2014).
International Search Report and Written Opinion for International U.S. Appl. No. 15/035,337 dated Sep. 17, 2015.
Little et al., "Mechanisms of acquired resistance to ERK1/2 pathway inhibitors," Oncogene, 32(10): 1207-1215 (2012).
Nijenhuis et al., "Is combination therapy the next step to overcome resistance and reduce toxicities in melanoma?" Cancer Treat Rev, 39(4): 305-312 (2013).
Valiathan et al., "Common Docking Domain Mutation E322K of the ERK2 Gene is Infrequent in Oral Squamous Cell Carcinomas," Asian Pac J Cancer P, 13(12): 6155-6157 (2012).

* cited by examiner

Primary Examiner — Carla J Myers
(74) Attorney, Agent, or Firm — Foley Hoag LLP

(57) ABSTRACT

Isolated mutant ERK polypeptides and nucleic acids encoding the mutant ERK polypeptides are provided. Methods of screening cancer-containing samples for an ERK polypeptide mutation that confers resistance to treatment with a first MAPK pathway inhibitor are provided. Methods of optimizing treatment of a subject having cancer and methods of identifying compounds useful in treating cancer are also provided.

9 Claims, 17 Drawing Sheets
Specification includes a Sequence Listing.

Figure 3
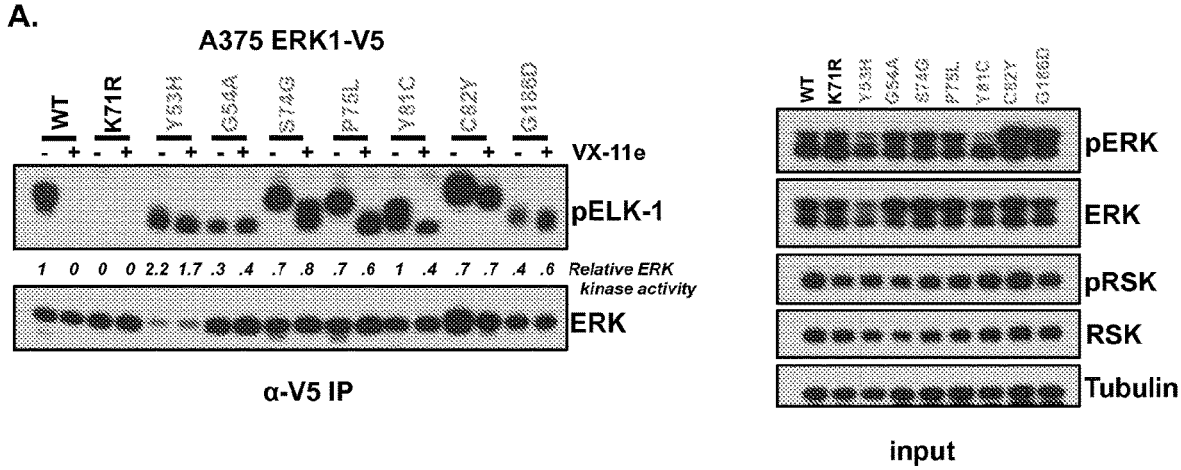
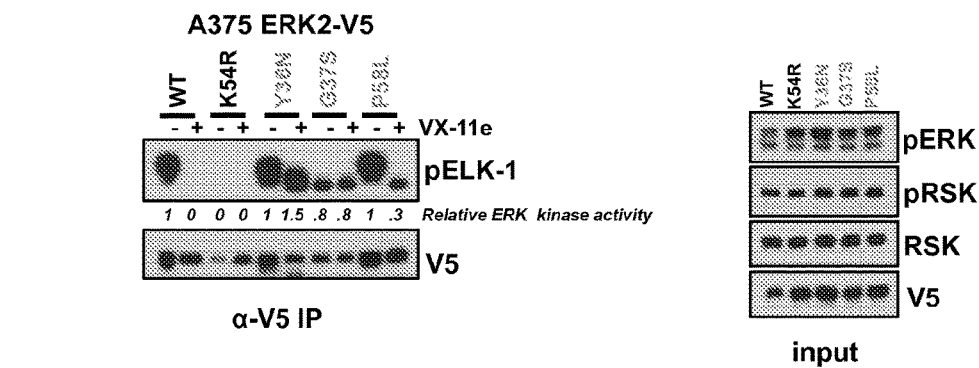

Figure 5
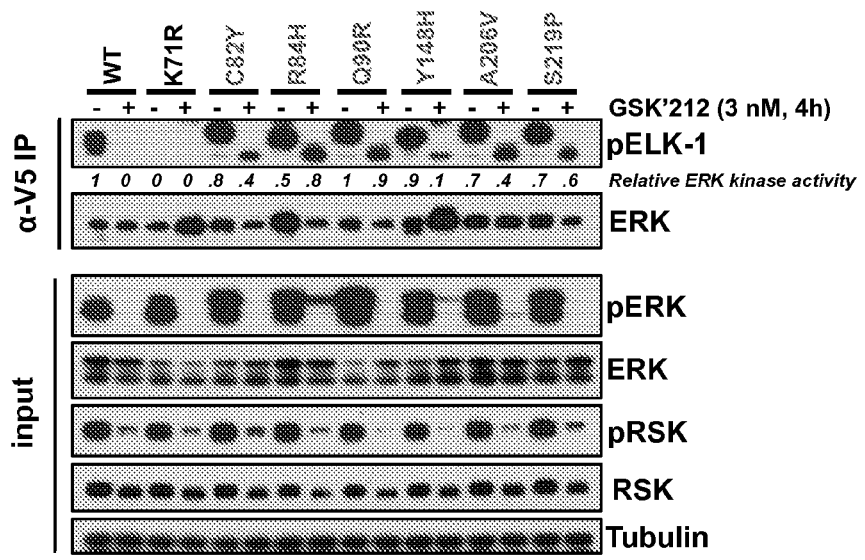
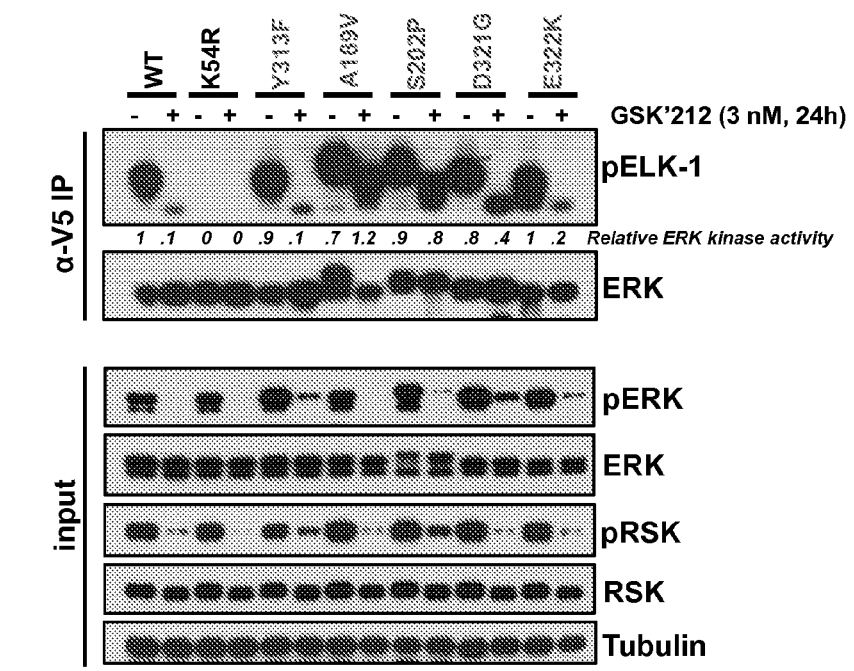

Figure 6
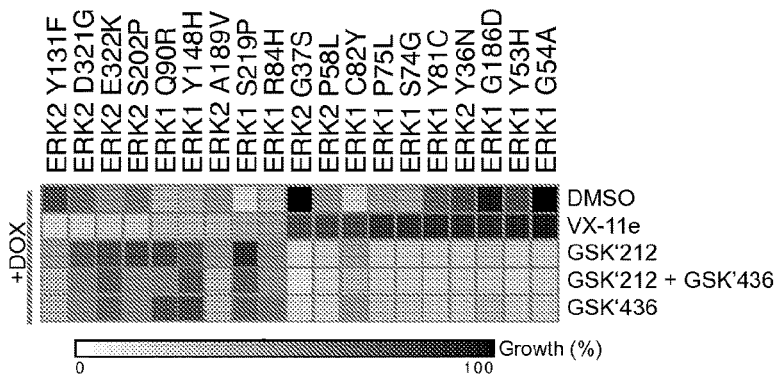
B. SKmel19
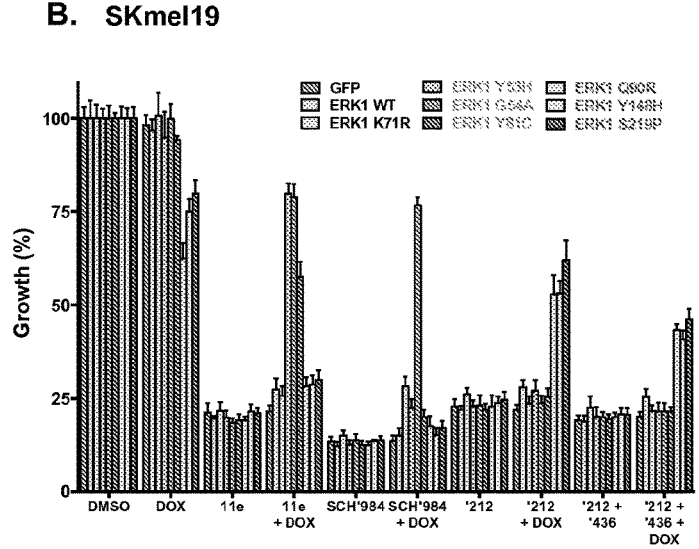
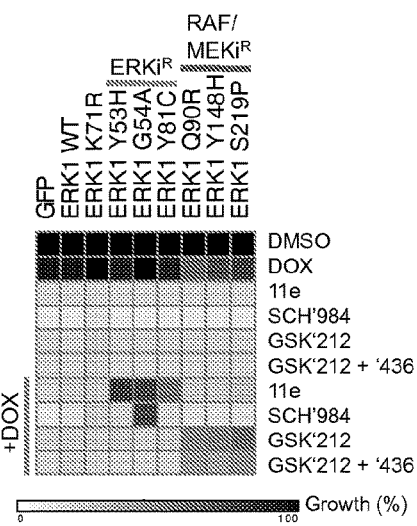
C. SKmel19
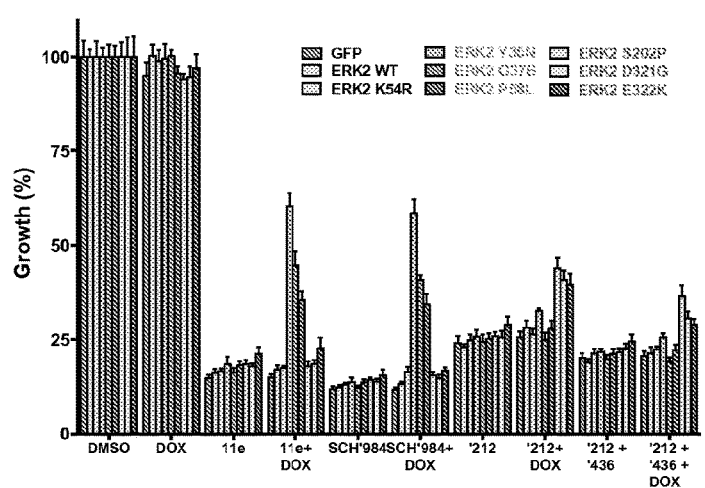
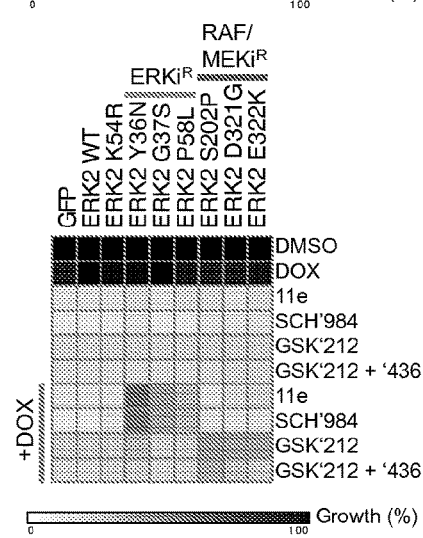

Figure 7
A.
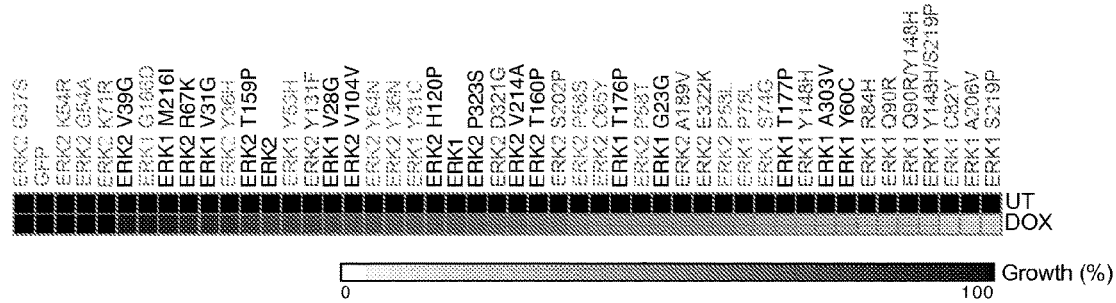
B.
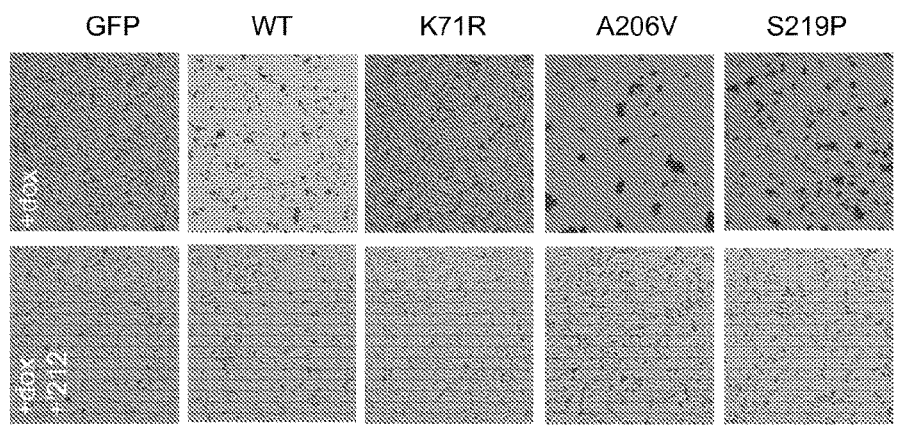
C.
| ERK1 colony | cDNA sequence | ERK2 colony | cDNA sequence |
|---|---|---|---|
| ERK1-1 | del 118-138 | ERK2-1 | del 49-140 |
| ERK1-2 | Q239H | ERK2-2 | del 49-140 |
| ERK1-3 | Y148* | ERK2-3 | del 49-140 |
| ERK1-4 | G11fs | ERK2-4 | del 49-140 |
| ERK1-5 | cDNA duplication | ERK2-5 | del 49-140 |
| ERK1-6 | I153fs | | |
| ERK1-K71R-1 | K71R | ERK1-K54R-1 | K54R |
| ERK1-K71R-2 | K71R | ERK1-K54R-2 | K54R |
| ERK1-K71R-3 | K71R | ERK1-K54R-3 | K54R |
| ERK1-K71R-4 | K71R | ERK1-K54R-4 | K54R |
| ERK1-K71R-5 | K71R | ERK1-K54R-5 | K54R |
| ERK1-K71R-6 | K71R | | |

Figure 10
A.
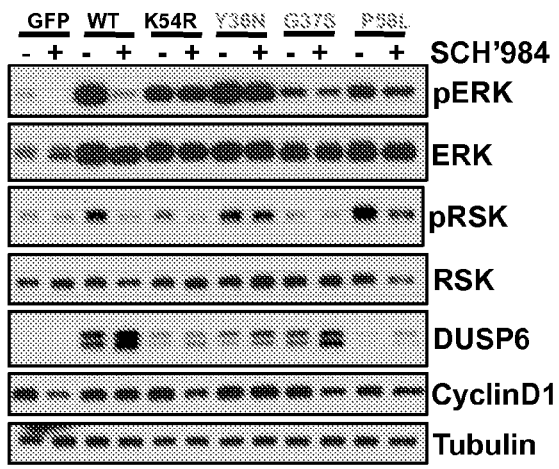
B.
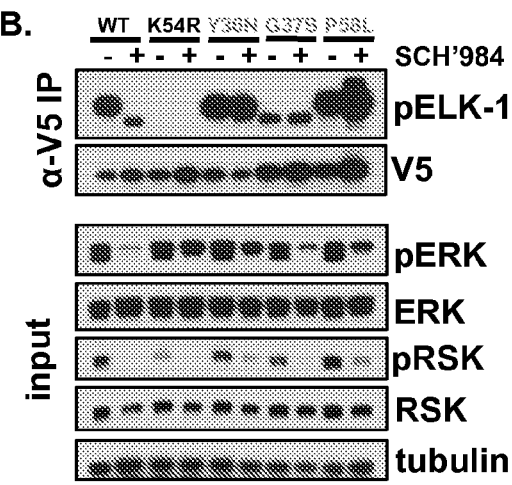

| aa 1 | aa 2 | mut1 | Freq aa1 | mut2 | Freq aa2 | Freq co-mut | reads |
|---|---|---|---|---|---|---|---|
| Y53C | Y60C | A->G | 0.018 | A->G | 0.01 | 0.0093 | 213980 |
| Y81C | Y60C | A->G | 0.067 | A->G | 0.01 | 0.0085 | 169462 |
| Y81C | Y53C | A->G | 0.067 | A->G | 0.018 | 0.0085 | 119232 |

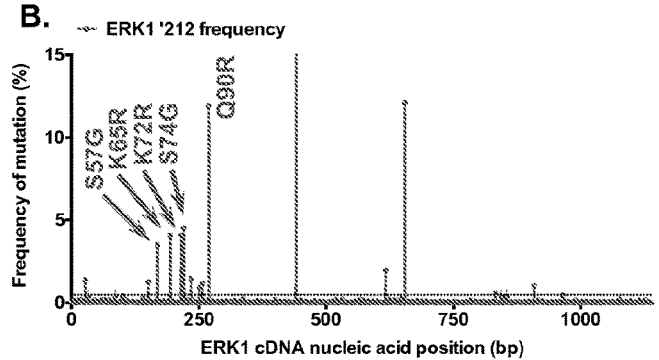

B. ERK1 '212 frequency

| aa 1 | aa 2 | mut1 | Freq aa1 | mut2 | Freq aa2 | Freq co-mut | reads |
|---|---|---|---|---|---|---|---|
| Q90R | S74G | A->G | 0.121 | A->G | 0.048 | 0.0411 | 263189 |
| S74G | K72R | A->G | 0.048 | A->G | 0.041 | 0.0393 | 342289 |
| K65R | S57G | A->G | 0.042 | A->G | 0.041 | 0.0389 | 244610 |
| K72R | K65R | A->G | 0.041 | A->G | 0.041 | 0.0387 | 286836 |
| S74G | K65R | A->G | 0.048 | A->G | 0.041 | 0.0384 | 279464 |
| K72R | S57G | A->G | 0.042 | A->G | 0.041 | 0.0379 | 218723 |
| S74G | S57G | A->G | 0.049 | A->G | 0.041 | 0.0375 | 211858 |
| Q90R | K72R | A->G | 0.121 | A->G | 0.041 | 0.0373 | 249115 |
| Q90R | K65R | A->G | 0.121 | A->G | 0.041 | 0.0367 | 191079 |
| Q90R | S57G | A->G | 0.121 | A->G | 0.042 | 0.0366 | 126229 |
| Y148H | S219P | T->C | 0.333 | T->C | 0.117 | 0.0161 | 19779 |
| Y148H | Q90R | T->C | 0.334 | A->G | 0.116 | 0.01 | 52042 |

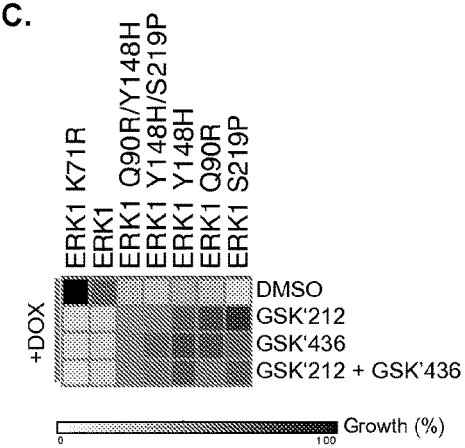

C.

Growth (%)

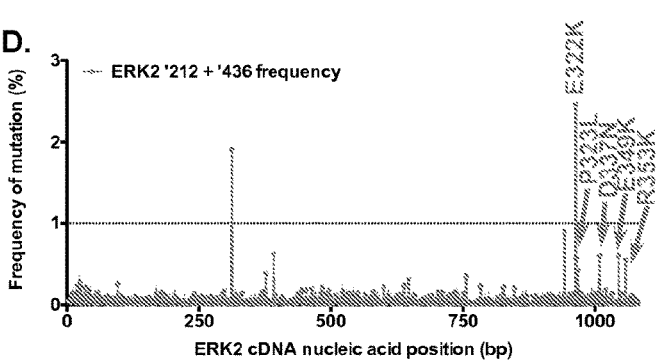

D. ERK2 '212 + '436 frequency

| aa 1 | aa 2 | mut1 | Freq aa1 | mut2 | Freq aa2 | Freq co-mut | reads |
|---|---|---|---|---|---|---|---|
| E349K | R353K | G->A | 0.011 | G->A | 0.009 | 0.0057 | 13248 |
| R353K | D337N | G->A | 0.009 | G->A | 0.008 | 0.0055 | 12555 |
| E322K | D337N | G->A | 0.082 | G->A | 0.007 | 0.0052 | 75489 |
| E322K | P323L | G->A | 0.08 | C->T | 0.006 | 0.0051 | 154742 |
| E349K | D337N | G->A | 0.012 | G->A | 0.007 | 0.0051 | 22222 |
| D337N | P323L | G->A | 0.007 | C->T | 0.006 | 0.0046 | 76025 |
| E322K | E349K | G->A | 0.085 | G->A | 0.013 | 0.0044 | 19406 |
| P323L | R353K | C->T | 0.011 | G->A | 0.009 | 0.0042 | 10279 |
| E349K | P323L | G->A | 0.013 | C->T | 0.008 | 0.004 | 19907 |

Figure 16

Table 4

| ERKi | Screen frequency | | 11e | | SCH-772984 | | Validation GSK'212 | | GSK'436 | | GSK'212+GSK'436 | |
|---|---|---|---|---|---|---|---|---|---|---|---|---|
| ERK1/ERK2 | ERK1 | ERK2 | ERK1 | ERK2 | ERK1 | ERK2 | ERK1 | ERK2 | ERK1 | ERK2 | ERK1 | ERK2 |
| G23G/- | 7.2% | <0.1% | S | | | | S | | S | | S | |
| I48N/?? | 0.8% | 0.4% | R | | | | S | S | S | S | S | S |
| Y53C/Y?? | 1.8% | <0.1% | | | | | | | | | | |
| Y53H/Y36N/H¹ | 1.1% | 22.0% | R | R | R* | R | S | S | S | S | S | S |
| G54S/G37S¹ | 0.8% | 3.6% | R | R | R | R | S | S | S | S | S | S |
| G54A/?? | 1.2% | 0.4% | S | | S | | | | | | | |
| Y60C/Y43 | 1.0% | <0.1% | | | | | | | | | | |
| K65R/K?? | 1.1% | <0.1% | | | | | | | | | | |
| K72R/K?? | 2.0% | <0.1% | | | | | | | | | | |
| I73S/I?? | 1.4% | <0.1% | | | | | | | | | | |
| S74G/?? | 2.7% | 0.3% | R | | | | S | S | S | S | S | S |
| P75L/P58L | 10.0% | 3.4% | R | R | | R | S | S | S | S | S | S |
| P75S/P58S/T¹ | 1.8% | <0.1% | | R | | | | | | | | |
| E77E/?? | 1.0% | <0.1% | | | | | | | | | | |
| Y81C/Y?? | 7.1% | <0.1% | R | | | | S | | S | | S | |
| Y??/Y64N¹ | <0.1% | <0.1% | | | | | | | | | | |
| C82Y/C65Y¹ | 8.9% | 0.4% | R | R | R | | S | S | S | S | S | S |
| R84H/R67K | <0.1% | 0.6% | S | S | | | R | S | R | S | R | S |
| V??/V104V | <0.1% | 2.6% | | | | | | | | | | |
| D??/D106D | <0.1% | 1.1% | | | | | | | | | | |
| G186D/G??? | 4.6% | 0.5% | R | | R | | S | | S | | S | |
| L??/L170L | <0.1% | 1.4% | | | | | | | | | | |
| Q???/??? | <0.1% | 1.4% | | | | | | | | | | |
| L306L/?? | 2.1% | <0.1% | | | | | | | | | | |
| P???/P323P | <0.1% | 0.6% | | | | | | | | | | |

¹ observed by sanger sequencing
* at lower concentrations

Figure 17

Table 5

| RAF/MEKi | Screen frequency | | | | Validation | | | | | | | |
|---|---|---|---|---|---|---|---|---|---|---|---|---|
| | GSK'212 | | GSK'212 + GSK'436 | | GSK'212 | | GSK'436 | | GSK'212+GSK'436 | | 11e | |
| ERK1/ERK2 | ERK1 | ERK2 | ERK1 | ERK2 | ERK1 | ERK2 | ERK1 | ERK2 | ERK1 | ERK2 | ERK1 | ERK2 |
| G51S/G54 | 1.3% | <0.1% | 0.2% | <0.1% | | | | | | | | |
| S57G/C60 | 3.5% | <0.1% | 0.4% | <0.1% | | | | | | | | |
| K65R/K68 | 4.1% | <0.1% | 0.4% | 1.0% | | | | | | | | |
| S74G/S77 | 4.5% | <0.1% | 0.6% | <0.1% | | | | | | | | |
| Q79*/Q82 | 1.5% | <0.1% | 1.7% | <0.1% | S | | | | S | | S | S |
| R84H/R67K | 0.9% | <0.1% | 10.2% | <0.1% | R | S | R | S | R | S | S | S |
| R84S/R67 | 0.2% | <0.1% | 0.7% | <0.1% | | | | | | | | |
| L86R/PL69 | 1.2% | <0.1% | 4.6% | <0.1% | | | | | | | | |
| Q90R/K73 | 11.9% | <0.1% | 2.6% | <0.1% | R | S | R | S | S | S | S | S |
| V104V | <0.1% | 0.8% | <0.1% | 1.9% | | | | | | | | |
| S135N/T116 | <0.1% | <0.1% | 0.7% | <0.1% | | | | | | | | |
| Y148H/Y131N/H | 34.9% | 1.2% | 42.8% | 0.6% | R | R | R | R | R | R | S | S |
| Y131F/C/S | <0.1% | 4.1% | <0.1% | <0.1% | R | R | R | R | R | R | S | S |
| A206V/A189V | 2.0% | <0.1% | 1.1% | <0.1% | R | S | S | S | S | S | S | S |
| M216I/M199 | 0.2% | <0.1% | 6.4% | <0.1% | R | R | R | R | R | R | | |
| S219P/S202P | 12.1% | <0.1% | 0.8% | <0.1% | R | S | R | S | R | S | S | S |
| Y205N | <0.1% | 0.7% | <0.1% | <0.1% | | | | | | | | |
| V214A | <0.1% | 12.0% | <0.1% | <0.1% | | | | | | | | |
| L252L | <0.1% | 0.6% | <0.1% | 0.4% | | | | | | | | |
| R278*/R261 | 0.6% | <0.1% | 2.7% | <0.1% | S | | S | | S | | S | |
| A303V/A286 | 1.0% | <0.1% | <0.1% | <0.1% | S | | S | | S | | S | |
| L287M | <0.1% | 1.8% | <0.1% | <0.1% | | | | | | | | |
| E303K | <0.1% | 0.5% | <0.1% | <0.1% | | | | | | | | |
| D321G | <0.1% | 11.3% | <0.1% | 2.5% | S | R | R | R | R | R | S | S |
| E322K | <0.1% | 8.4% | <0.1% | 0.4% | S | R | R | R | R | S | S | S |
| P323L | <0.1% | 0.5% | <0.1% | <0.1% | | | | | | | | |
| P323S | <0.1% | 4.4% | <0.1% | <0.1% | | | | | | | | |
| D337N | <0.1% | 0.6% | <0.1% | 0.6% | | | | | | | | |
| E349K | <0.1% | 1.0% | <0.1% | 0.6% | | | | | | | | |
| R353K | <0.1% | 0.7% | <0.1% | 0.5% | | | | | | | | |

# ERK1 AND ERK2 MUTATIONS THAT CONFER RESISTANCE TO MAPK PATHWAY INHIBITORS

RELATED APPLICATIONS

This application claims the benefit under 35 U.S.C. § 371 of International Application No. PCT/US2015/035337, filed Jun. 11, 2015, which claims the benefit of Provisional Application No. 62/012,175, filed Jun. 13, 2014 which are incorporated by reference herein in their entirety.

SEQUENCE LISTING

The instant application contains a Sequence Listing which has been submitted electronically in ASCII format and is hereby incorporated by reference in its entirety. The ASCII copy, created on Jun. 7, 2015, is named 14293-440 sequence listing_ST25.txt and is approximately 29.8 KB in size.

BACKGROUND

BRAF is mutated in approximately 50% of melanomas, resulting in constitutive activation of the MAPK pathway (BRAF-MEK-ERK) (1). Inhibitors targeting RAF and MEK (a key downstream effector kinase in the pathway) improve survival of BRAF-mutant melanoma patients, and are thus in common clinical use for this indication (2-4). In particular, combined RAF/MEK inhibition appears to improve progression free survival compared to RAF or MEK monotherapy (2, 5). Despite these therapeutic successes, nearly all patients develop progressive disease that is resistant to these agents (2, 6).

Multiple studies describing mechanisms of resistance to RAF/MEK inhibition have been published. Reactivation of the MAPK pathway through a variety of means, including alternatively spliced BRAF, NRAS or MEK1/2 mutations, COT up-regulation, or receptor tyrosine kinase signaling, is the most common drug resistance mechanism (7-11). Since all of these agents converge on sustained activation of ERK, the clinical development of small molecule ERK inhibitors is of considerable interest. More generally, ERK signaling represents a key downstream effector of RAS mutations in many cancer types, suggesting that ERK inhibitors might eventually have multiple indications in oncology.

ERK1 and ERK2 proteins are 84% identical and comprise the only known substrates of MEK, resulting in dual phosphorylation that fully activates ERK kinase activity. Conversely, ERKs are negatively regulated by dephosphorylation by dual specificity phosphatases (DUSPs) (12, 13). DUSPs also become induced by ERK signaling, creating a negative feedback loop (14). Other downstream ERK effectors include kinases such as RSK and MSK, cytoskeletal molecules, nucleoporins, and transcription factors (e.g., c-FOS, ELK-1, ETS-1, MITF). Oncogenic dysregulation of this ERK program may profoundly impact cell proliferation and survival (15). As an additional feedback mechanism, ERK can target upstream kinases with inactivating phosphorylation events (e.g., RAF-1) (16).

Recently, MAPK1$^{E322K}$ (ERK2) mutations were identified at low frequency (8%) in cervical carcinoma (17). The glutamic acid residue at position 322 is located in common docking domain (also called the D-site recruitment site) through which ERK1/2 binds to substrates. This is also where negative regulators of ERK bind, such as DUSP6. Therefore, although ERK2$^{E322K}$ does not exhibit increased basal kinase activity in vitro, it likely remains activated in vivo because of reduced DUSP binding and hence loss of negative regulation (18). The adjacent residue (D321) is homologous to the sevenmaker (rlsem) gain-of-function ERK mutation in *Drosophila melanogaster*. Both homologues show reduced binding to their cognate phosphatase negative regulators, resulting in elevated activity (19).

Several small molecule ERK inhibitors have entered clinical trials. Given the importance of secondary kinase mutations as resistance mechanisms in many oncogene-driven cancers, we wished to discover mutations in ERK that confer resistance to ERK inhibitors. We reasoned that at least some such ERK mutations might also confer resistance to RAF/MEK inhibitors. (In this regard, such studies might also identify constitutively active variants of ERK, which have remained elusive despite intensive study.) Random mutagenesis screens have successfully identified clinically relevant resistance alleles (20, 21) in multiple kinase oncogene driven malignancies. Thus, we employed random mutagenesis in BRAF-mutant melanoma cells to identify mutations in ERK1 or ERK2 that could confer resistance to MAPK inhibitors.

Elucidation of the mechanisms that underlie resistance to specific agents is essential to discovering treatment approaches that are for effective long-term treatment strategies, for new methods of identifying patients that are likely to benefit from the treatment strategies, and for methods of treating patients with the effective long-term treatment strategies. Methods for screening new inhibitors are also needed.

BRIEF SUMMARY

The present invention relates to the development of resistance to therapeutic agents in the treatment of cancer and identification of targets that confer resistance to treatment of cancer. The present invention also relates to identification of parallel drug targets for facilitating an effective long-term treatment strategy and to identifying patients that would benefit from such treatment.

In one aspect, a method of screening a cancer cell-containing sample of a subject for an ERK mutation conferring resistance to treatment with a first MAPK pathway inhibitor is provided. The method includes extracting nucleic acid from cells of the cancer; and identifying in the sample a nucleic acid molecule encoding an ERK1 polypeptide including one or more mutations with respect to a nucleic acid molecule encoding a wild-type ERK1 polypeptide (SEQ ID NO: 3), the one or more mutations occurring at positions encoding one or more amino acids in the ERK1 polypeptide selected from the group consisting of I48, Y53, G54, S74, P75, Y81, C82, R84, Q90, Y148, G186, A206 and S219 and/or a nucleic acid molecule encoding an ERK2 polypeptide including one or more mutations with respect to a nucleic acid molecule encoding a wild-type ERK2 polypeptide (SEQ ID NO: 4), the one or more mutations occurring at positions encoding one or more amino acids in the ERK2 polypeptide selected from the group consisting of Y36, G37, P58, Y64, C65, Y131, A189, S202, D321, and E322. The presence of the one or more of the mutations in the ERK1 polypeptide and/or the ERK2 polypeptide identifies the subject as being resistant to treatment with the first MAPK pathway inhibitor.

In another aspect, an isolated mutant ERK polypeptide having an ERK activity is provided. The mutant ERK polypeptide includes an amino acid sequence having at least one amino acid substitution as compared to a wild type ERK polypeptide selected from the group consisting of ERK1 (SEQ ID NO: 3) and ERK2 (SEQ ID NO: 4), the at least one amino acid substitution conferring resistance to a first MAPK inhibitor on the mutant ERK polypeptide, where the wild type ERK polypeptide is a) ERK1 and the at least one substitution occurs at one or more amino acid positions selected from I48, Y53, G54, S74, P75, Y81, C82, R84, Q90, Y148, G186, A206 and S219; or b) ERK2 and the at least one substitution occurs at one or more amino acid positions selected from Y36, G37, P58, Y64, C65, Y131, A189, S202, D321, and E322.

In another aspect, an isolated nucleic acid molecule encoding a mutant ERK polypeptide having an ERK activity is provided. The mutant ERK polypeptide includes an amino acid sequence having at least one amino acid substitution as compared to a wild type ERK polypeptide selected from ERK1 (SEQ ID NO: 3) and ERK2 (SEQ ID NO: 4). The at least one amino acid substitution confers resistance a first MAPK pathway inhibitor on the mutant ERK protein where the wild type ERK polypeptide is a) ERK1 and the at least one substitution occurs at one or more amino acid positions selected from I48, Y53, G54, S74, P75, Y81, C82, R84, Q90, Y148, G186, A206 and S219; or b) ERK2 and the at least one substitution occurs at one or more amino acid positions selected from Y36, G37, P58, Y64, C65, Y131, A189, S202, D321, and E322.

In yet another aspect, a cell-based screening method for identifying a test compound as a second MAPK pathway inhibitor for treatment of a subject having cancer where the subject is resistant to treatment with a first MAPK pathway inhibitor is provided. The method includes contacting a host cell including an expression vector including a nucleic acid that encodes a mutant ERK polypeptide with the test compound. Sensitivity of the host cell to the test compound identifies the compound as a second MAPK pathway inhibitor.

In another aspect, a method of identifying a compound that is useful in treating cancer is provided. The method includes providing an assay composition comprising a mutant ERK polypeptide and an ERK substrate and contacting the assay composition with a test compound under conditions that permit phosphorylation of the ERK substrate in the absence of the test compound. The method also includes determining the effect of the compound on phosphorylation of the ERK substrate, where down-modulation of phosphorylation of the ERK substrate as compared to a suitable control identifies the compound as a compound that is useful in treating cancer.

In yet another aspect, a method of identifying a compound that is useful in treating cancer is provided. The method includes providing a cell including a mutant ERK polypeptide and contacting the cell with a test compound. The method also includes determining the effect of the compound on phosphorylation of an ERK substrate or the effect of the compound on cell proliferation, where down-modulation of phosphorylation of the ERK substrate or reduction in cell proliferation as compared to a suitable control identifies the compound as a compound that is useful in treating cancer.

In another aspect, a method of optimizing treatment of a subject having cancer is provided. The method includes extracting nucleic acid from cells of the cancer and assaying a nucleic acid molecule encoding an ERK polypeptide and identifying the nucleotide sequence of a nucleic acid molecule encoding the ERK polypeptide to identify an alteration of an amino acid residue at one or more amino acids of the encoded ERK polypeptide that confers resistance to a first MAPK pathway inhibitor. The presence of nucleotides that alter the identity of an amino acid residue at one or more amino acids of the encoded ERK polypeptide relative to the amino acid at one or more positions selected from the group consisting of I48, Y53, G54, S74, P75, Y81, C82, R84, Q90, Y148, G186, A206 and S219 of ERK1 (SEQ ID NO: 3), or the presence of nucleotides that alter the identity of an amino acid residue at one or more amino acids of the encoded ERK polypeptide relative to the amino acid at one or more positions selected from the group consisting of Y36, G37, P58, Y64, C65, Y131, A189, S202, D321, and E322 of ERK2 (SEQ ID NO: 4) indicates a need to treat the subject with a second MAPK pathway inhibitor.

In yet another aspect, a method of optimizing treatment of a subject having cancer is provided. The method includes extracting nucleic acid from cells of the cancer; and assaying a nucleic acid molecule encoding an ERK polypeptide and identifying the nucleotide sequence of a nucleic acid molecule encoding the ERK polypeptide to identify an alteration of an amino acid residue at one or more amino acids of the encoded ERK polypeptide that confers resistance to a first MAPK pathway inhibitor. The method includes withdrawing administration of the first MAPK inhibitor to the subject when the nucleotides that alter the identity of an amino acid residue at one or more amino acids of the encoded ERK polypeptide relative to the amino acid include at one or more positions selected from the group consisting of I48, Y53, G54, S74, P75, Y81, C82, R84, Q90, Y148, G186, A206 and S219 of ERK1 (SEQ ID NO: 3), or the nucleotides that alter the identity of an amino acid residue at one or more amino acids of the encoded ERK polypeptide relative to the amino acid include at one or more positions selected from the group consisting of Y36, G37, P58, Y64, C65, Y131, A189, S202, D321, and E322 of ERK2 (SEQ ID NO: 4).

Figure 1:
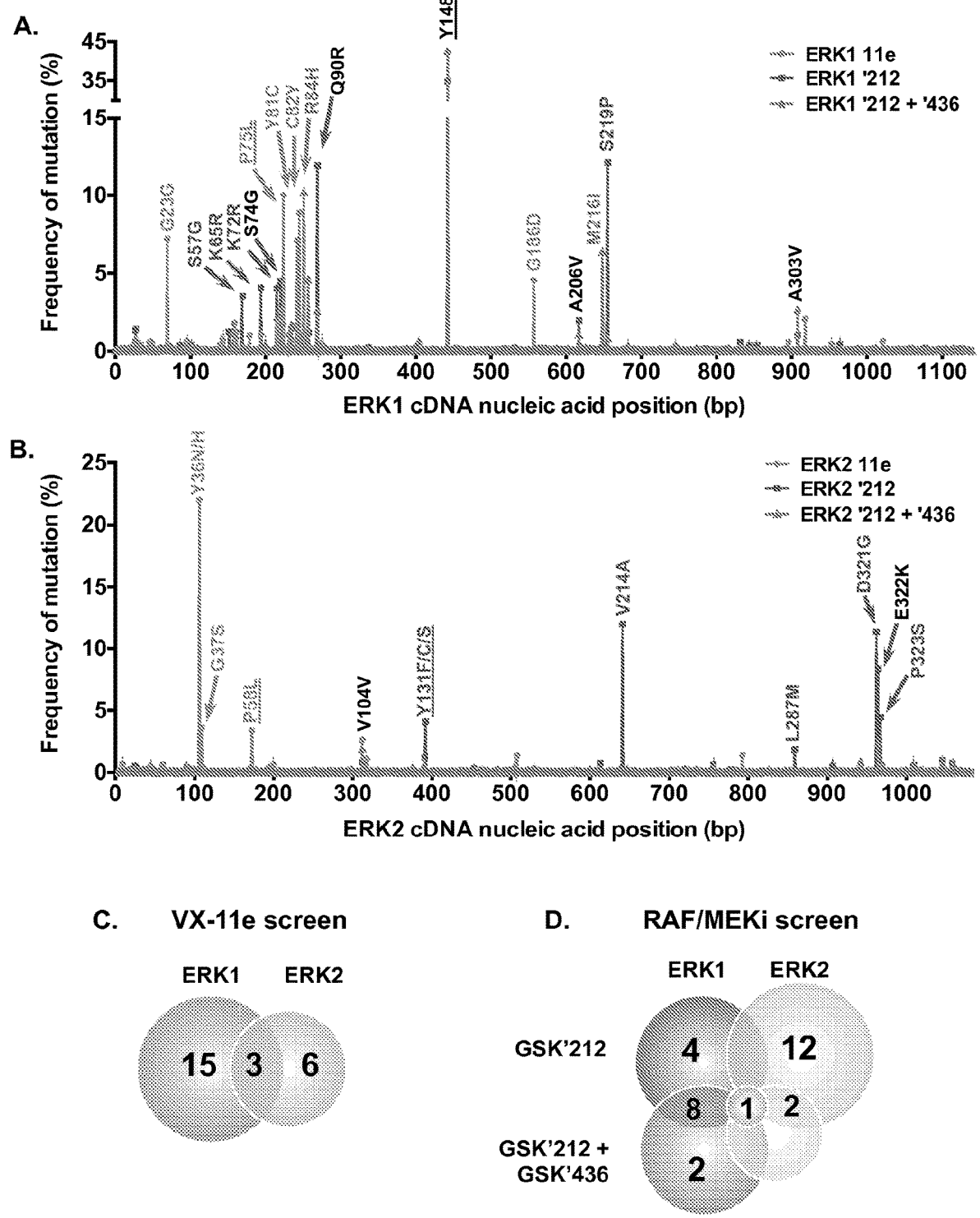
FIGS. 1A-1D illustrate the frequency of specific base pair changes in a random mutagenesis screen.

(A,B) Frequency (number of non-WT reads/total number of reads×100) of mutation at each base pair (bp) for ERK1 (A) and ERK2 (B). VX-11e is labeled in red, trametinib (GSK'212) is labeled in blue, and trametinib+dabrafenib ('212+'436) is labeled in green. Amino acid changes for high frequency nucleotide changes are highlighted. Alleles highlighted in red correspond to ERK inhibitor, alleles in blue to MEK inhibitor and alleles in green to RAF+MEK inhibitor. Alleles in black were found in more than one drug group. Underlined alleles are analogous alterations between ERK1 and ERK2. (C,D) Overlap of all significantly mutated nucleotides in ERK1/2 for ERK inhibitor (C) and RAF/MEK inhibitor (D).

FIGS. 2A-2D show that mutations in the ERK1/2 drug binding pocket confer resistance to ERK inhibitor.

(A) Single base pair mutations were introduced in tet-inducible ERK1 or ERK2 and infected into A375 cells. Cells were analyzed for growth by MTS assay with VX-11e and DOX. Raw values were converted to percent growth and normalized to DMSO. Percent growth values are depicted in a heat map, with alleles sorted by growth in VX-11e+DOX. GFP and kinase dead ERK1K71R/ERK2K54R serve as controls. A black * indicates the ERK2 allele was sequenced in isolated resistant colonies; a red * indicates it was sequenced in both the screen and resistant colonies. (B) Selected alleles from FIG. 2A were tested with SCH722984 (SCH'984) by MTS assay. Percent growth was depicted by heat map. Gray squares indicate the alleles were not tested. (C) A375 cells expressing validated alleles from FIG. 2A were treated with DOX with or without VX-11e and harvested for immunoblotting. Tubulin was used as a loading control. (D) Structural localization of validated ERK1 and ERK2 alleles (spheres) mapped onto ERK2 (cartoon) modeled with VX-9a (sticks). VX-9a is a paralogue to VX-11e [PDB ID:3I60]. ERK1 alleles are listed above analogous ERK2 alleles. Untested alleles are in gray. The glycine rich loop is colored in teal, the αC-helix in magenta, and the activation loop in blue.

FIGS. 3A-3B illustrate that kinase activity is maintained in mutant ERK alleles after VX-11e addition.

(A,B) IP kinase assays for ERK1 (A) and ERK2 (B). V5-tagged ERK1 or ERK2 was monitored for phosphorylation of recombinant ELK peptide with either DMSO or VX-11e added during the kinase assay. 2% of the lysate was run as input to confirm expression.

FIGS. 4A-4D illustrate that ERK activating mutations that confer resistance to RAF/MEK inhibitors.

(A) A375 cells expressing tet-inducible putative RAF/MEK inhibitor resistant alleles were analyzed by MTS assay for cell growth in the presence of trametinib (GSK'212), dabrafenib (GSK'436) or trametinib+dabrafenib (GSK'212+GSK'436) and DOX. Cell growth was normalized to DMSO controls and percent growth was depicted by heat map. Alleles are sorted by growth in GSK'212+DOX. GFP and kinase dead ERK1$^{K71R}$ and ERK2$^{K54R}$ serve as controls. (B) Localization of validated RAF/MEK inhibitor resistant alleles (spheres) on ERK2 crystal structure (cartoon). αC-helix is labeled in magenta and the activation loop in blue. ERK1 alleles are listed above analogous ERK2 alleles. Non-validating/un-tested alleles labeled in gray. PDB ID: 2ERK (C,D) Cells expressing ERK1 (C) or ERK2 (D) alleles from (A) were examined for ERK signaling after exposure to trametinib (GSK'212). All cells were exposed to DOX to induce ERK allele expression.

FIGS. 5A-5B illustrate that RAF/MEK inhibitor resistant alleles maintain kinase activity in the presence of MEK inhibitor.

(A,B) A375 cells were transfected with V5 tagged ERK1 (A) or ERK2 (B), treated with trametinib (GSK'212) and harvested for IP kinase assays. ERK activity was examined by phosphorylation of a recombinant ELK-1 peptide, and analyzed by immunoblotting. Input is 2% of the lysate added to each IP.

FIGS. 6A-6C illustrate that ERK inhibitor resistant alleles are sensitive to RAF/MEK inhibitor, and vice versa.

Figure 2:
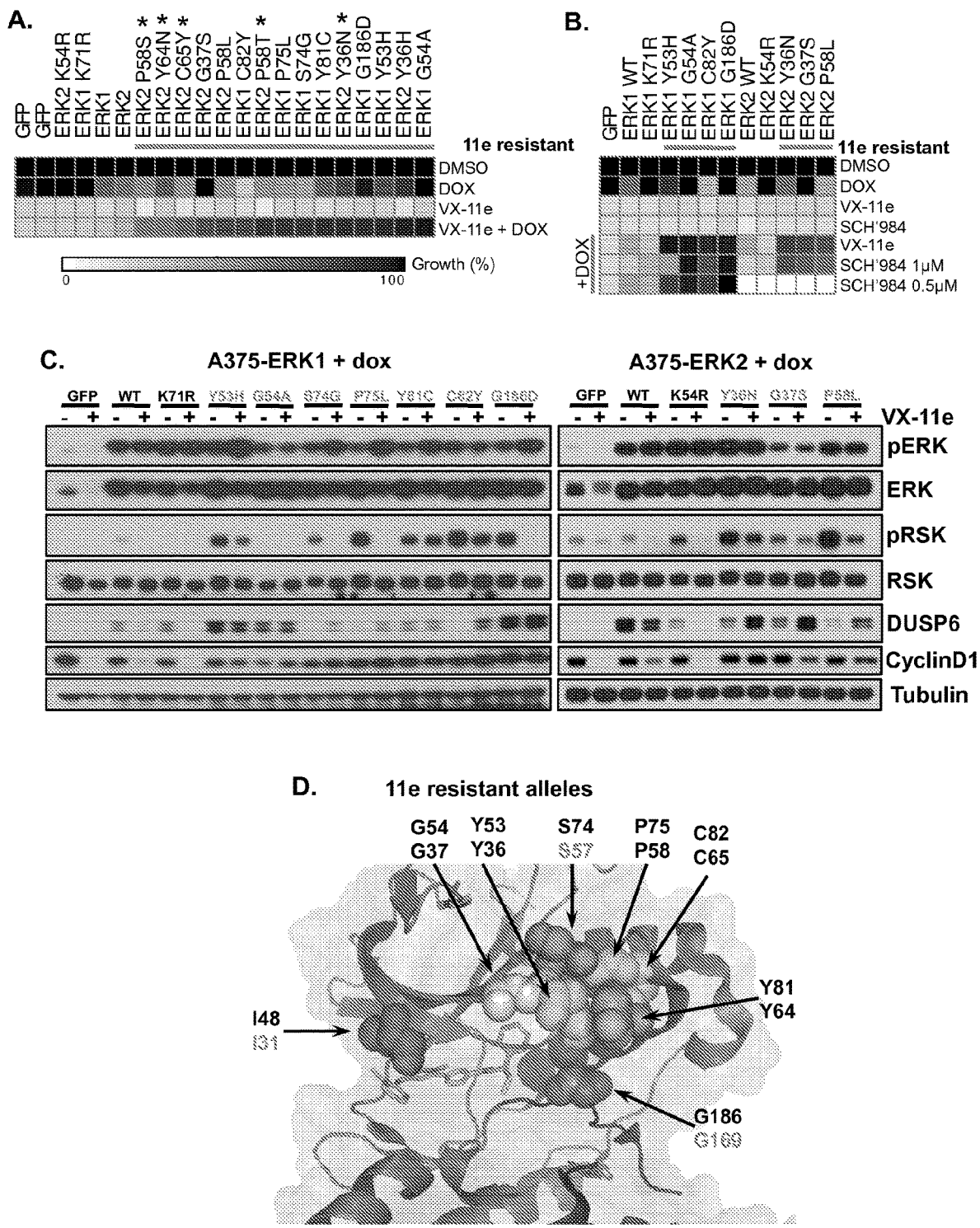
Figure 4:
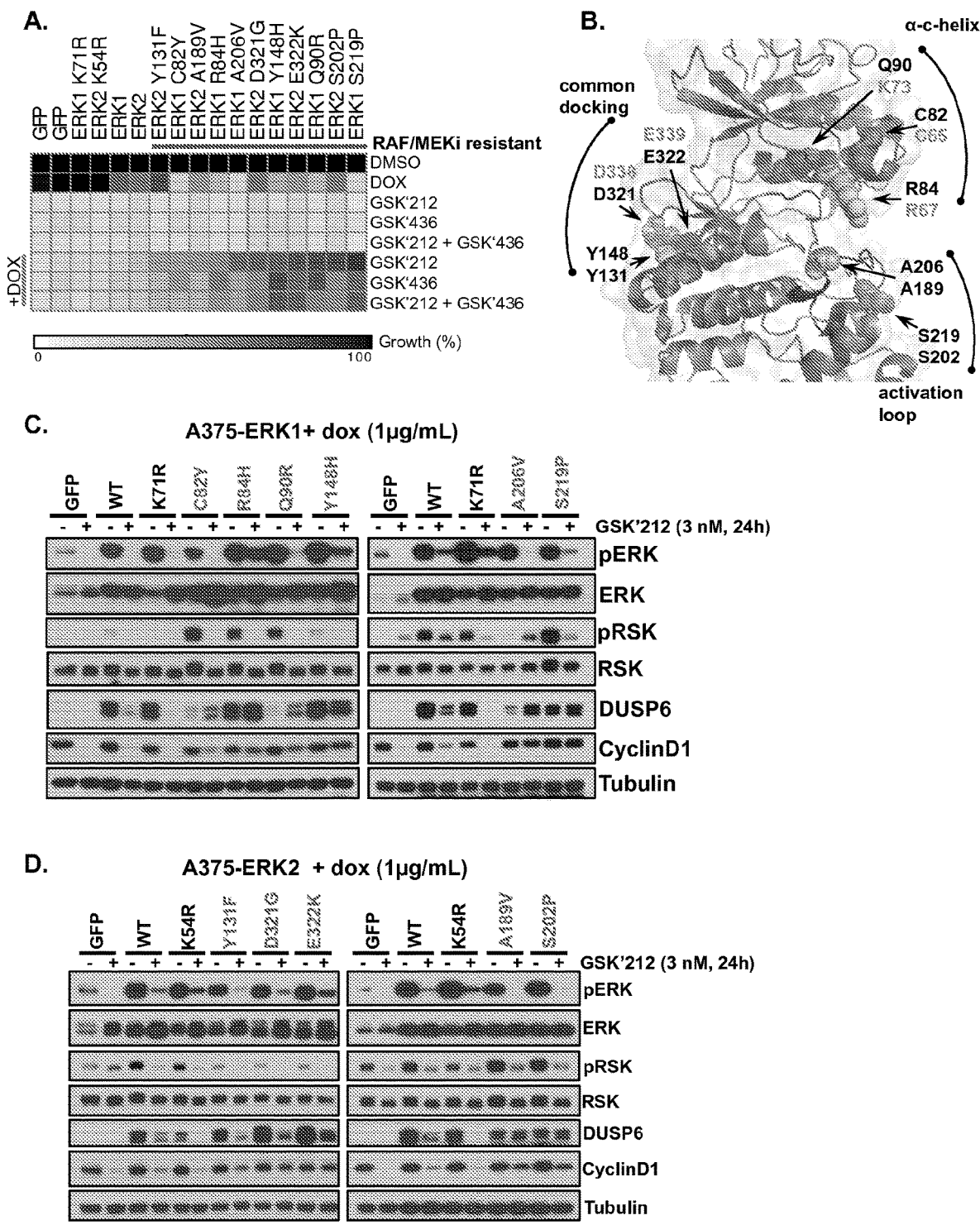

(A) A375 cells expressing tet-inducible ERK1/2 resistance alleles from FIG. 2 and FIG. 4 were exposed to VX-11e, trametinib (GSK'212), dabrafenib (GSK'436), and trametinib+dabrafenib (GSK'212+GSK'436). Proliferation was assayed by MTS assay after four days and normalized to DMSO to determine percent growth. Percent growth was depicted by heat map and sorted by sensitivity to VX-11e+DOX. (B,C) SKmel19 cells were infected with selected ERK1 (B) or ERK2 (C) alleles and analyzed for proliferation by MTS assay. VX-11e, SCH772984 (SCH'984), trametinib (GSK'212), and trametinib+dabrafenib (GSK'212+GSK'436) were added with DOX. VX-11e resistant alleles are in RED and RAF/MEK inhibitor resistant alleles in BLUE. Percent growth values are on the left, and heat map depiction of cell growth on the right.

FIGS. 7A-7C illustrate that expression of ERK1/2 is lethal in A375 cells.

(A) A375 cells infected with tet-inducible ERK1/2 alleles were analyzed for cell proliferation 72 h after induction of ERK expression by DOX using MTS assays. Alleles for controls, alleles that are resistant to ERK inhibitor, and alleles that are resistant to RAF/MEK inhibitors are labeled. ERK1C82Y is resistant to RAF, MEK and ERK inhibitors. (B) Phase contrast micrograph of A375 cells expressing tet-inducible constructs as indicated. Top panels are with DOX alone, bottom panels are with DOX+trametinib (GSK'212). (C) Summary of cDNA sequences corresponding to ERK1 and ERK2 colonies.

FIGS. 8A-8G illustrate the frequency of alteration at specific base pairs and sequencing coverage.

(A-F) Frequency of non-wild-type alterations at each base pair for ERK1 (A-C) and ERK2 (D-F) for ERK inhibitor (11e; A,D), MEK inhibitor ('212; B,E), and RAF+MEK inhibitors ('212+'436; C,F). Coverage is graphed on the right y-axis (total reads). The 5% false data rate is indicated on each graph as a dotted line. The false discovery rate for each screen is as follows, ERK1: VX-11e 0.7%, GSK'212 0.5%, GSK'212+GSK'436 0.6% and ERK2: VX-11e 0.5%, GSK'212 0.4%, GSK'212+GSK'436 1.0%. (G) Growth assay for A375 cell expressing dox-inducible GFP, WT ERK1/2, kinase dead ERK1/2, and ERK1 I48N or G186D with ERK inhibitor.

FIGS. 9A-9B show expression of ERK alleles induce ERK signaling.

(A-B) A375 cells stably expressing wild-type or mutant ERK1 (A) or ERK2 (B) alleles were exposed to vehicle or DOX for 24 hours, then analyzed for signaling by western blot. Alleles in red are resistant to ERK inhibitor, alleles in blue are resistant to RAF/MEKi, and the allele in purple is resistant to both.

FIGS. 10A-10B show that ERK inhibitor resistant alleles maintain signaling and ERK kinase activity with SCH722984.

(A) A375 cells stably expressing ERK inhibitor resistant ERK2 alleles were treated with DOX with or without SCH722984 (SCH'984) and analyzed for ERK signaling by western blotting. (B) A375 cells were transiently transfected with ERK2-V5 alleles then treated with SCH'984 for 24 h, then V5-tagged ERK1/2 were examined for kinase activity via IP kinase assays.

Figure 11:
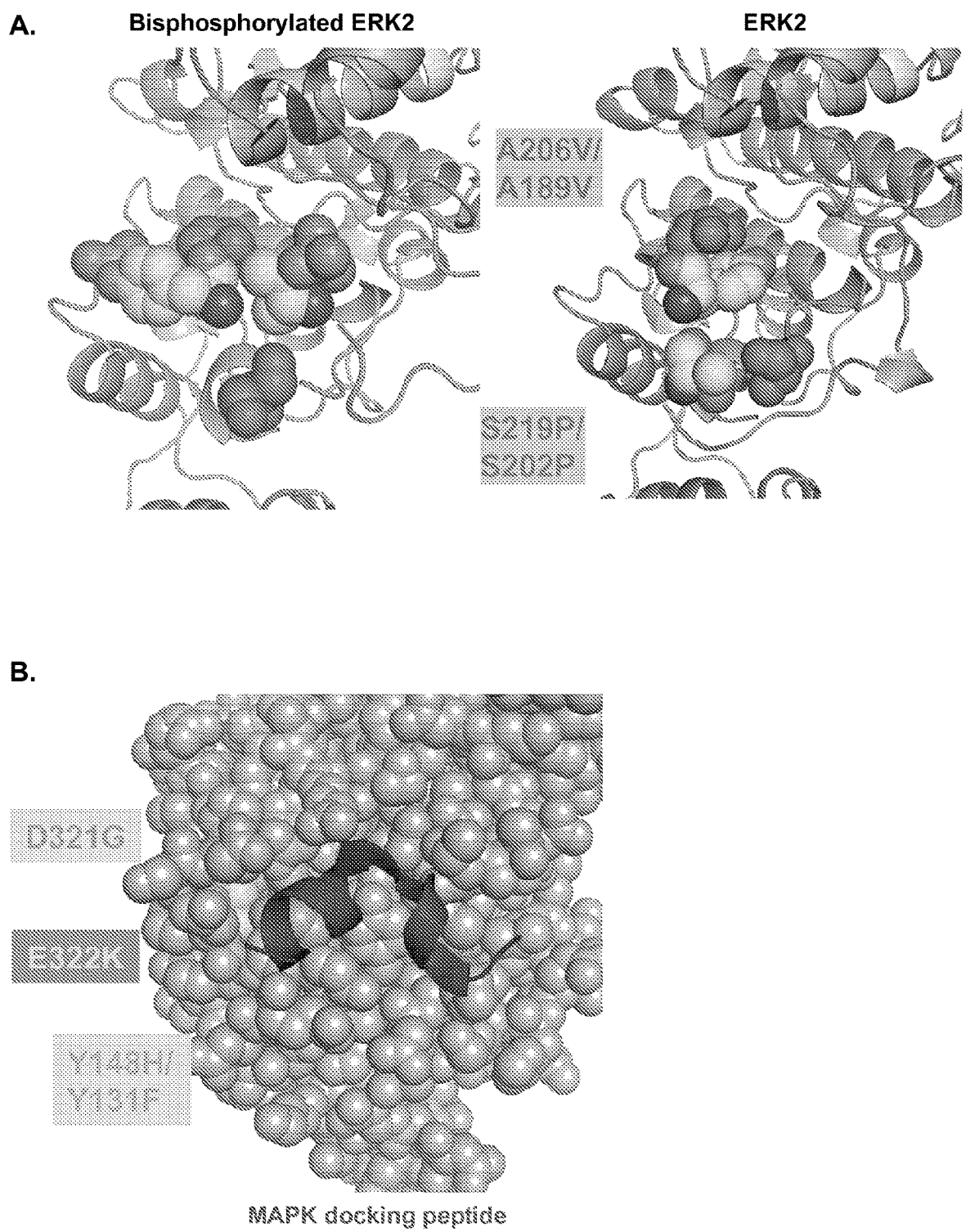

FIGS. 11A-11B illustrate localization of RAF/MEK inhibitor alleles (A) RAF/MEKi resistant alleles, ERK1$^{A206V}$/ERK2$^{A189V}$ (magenta spheres) and ERK1$^{S219P}$/ERK2$^{S202P}$ (red spheres) are mapped onto the 3-dimensional crystal structure of ERK2 (cartoon). The phospho residues threonine and tyrosine are labeled by element with carbon colored in green. PDB: 1ERK, 2ERK (bisphosphorylated) (B) Three common docking domain alleles resistant to RAF/MEK inhibitor are mapped on ERK2 crystal structure (gray spheres) with the MAPK docking peptide (blue cartoon). ERK2$^{D321G}$ (teal), ERK2$^{E322K}$ (green), and ERK1$^{Y148H}$/ERK2$^{Y131F}$ (orange) are indicated. PDB ID: 4FMQ.

FIGS. 12A-12E show non-validating alleles for ERK1 and ERK2.

(A-E) A375 cells expressing DOX-inducible ERK1 (A,B) or ERK2 (C,D) alleles were incubated with increasing doses of VX-11e (A,C) or GSK'212 (B,D). (E) A375 cells were infected with DOX-ERK1 or ERK2 alleles and exposed to VX-11e (2 μM), trametinib (GSK'212, 3 nM), dabrafenib (GSK'436, 50 nM), or trametinib+dabrafenib (GSK'212+GSK'436, 1 nM+10 nM) and analyzed for growth by MTS assay. Percent growth is depicted by heat map. Cells are sorted by sensitivity to VX-11e.

FIGS. 13A-13D illustrates co-occurring alleles.

(A,B,D) Frequency of co-mutated alleles. aa1 is the first co-occurring mutation and aa2 is the second co-occurring mutation. mut1 and mut2 are the base changes. Freq aa1 and Freq aa2 is the frequency of mutation of aa1 or aa2. Freq co-mut is the frequency of the co-occurring mutation for aa1 and aa2. Reads are the number of reads where both mutations were observed. (A) Co-mutated alleles for ERK1 VX-11e screen. (B) Top, frequency plot for ERK1+ GSK'212 screen by base pair. Bottom, table with co-mutated allele frequencies. (C) A375 cells expressing DOX-inducible ERK1 co-mutated alleles or single alleles were analyzed for growth by MTS assay. Percent growth is depicted by heatmap and sorted by sensitivity to GSK'212. (D) Left, frequency plot for ERK2+GSK'212+GSK'436 screen by base pair. Right, table with co-mutated allele frequencies.

Figure 14:
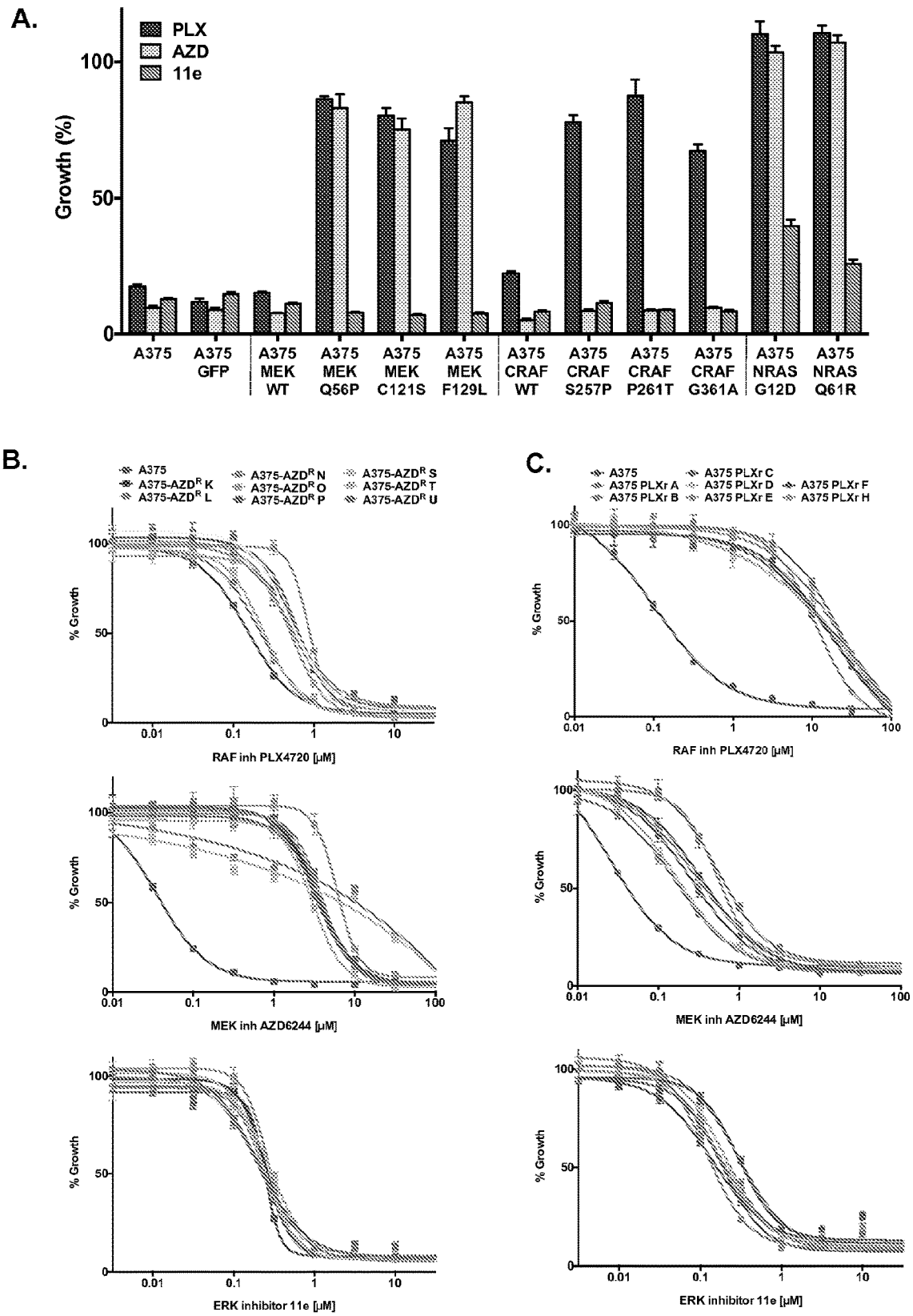

FIGS. 14A-14C illustrate that RAF/MEK inhibitor resistant cells are sensitive to ERK inhibitor.

(A) A375 cells were stably infected with DOX inducible GFP, MEK WT, and known resistance alleles in MEK and NRAS. CRAF WT and RAFi resistant mutants were stably expressed from constitutive promoters. Cells were exposed to RAF inhibitor (PLX4720; 1 μM), MEK inhibitor (AZD6244; 1 μM), and ERK inhibitor (VX-11e; 1 μM) and DOX (1 μg/mL). (B) ENU mutagenized A375 cells were continuously cultured in AZD6244 (B) or PLX4720 (C) for 2.5 weeks until resistant colonies appeared. Single colonies (A-U) were expanded and examined for sensitivity to PLX-4720, AZD6244, and VX-11e.

FIG. 15A illustrates that ERK1/2 alleles confer resistance in WM266.4 cells.

(A) Left, A375 cells expressing selected DOX-inducible ERK1/2 alleles were analyzed for growth by MTS assay with VX-11e (2 μM), GSK'212 (3 nM), or GSK'212+ GSK'436 (1 nM+10 nM). Right, heatmap of percent growth from left panel. ERKi resistant alleles are labeled red and RAF/MEKi resistant alleles are labeled blue.

FIG. 16 shows Table 4.

FIG. 17 shows Table 5.

Screen results and validation for ERK inhibitor (Table 4) or RAF and MEK inhibitors (Table 5). The altered codon for each significantly mutated base pair at each codon is listed Analogous mutations in ERK1 and ERK2 are in the same row. Alleles in gray were not identified in the screen and not tested. They are listed for reference, as the analogous allele was sequenced in the screen. In the "Screen Frequency" column, percents in bold fall above the 5% false discovery rate. In the "validation" columns, R is resistant (above a 3-fold increase in cell growth) and S is sensitive (Less than 3-fold increase in cell growth). Unlabelled cells were not tested.

DETAILED DESCRIPTION

The present invention relates to the development of resistance to therapeutic agents in the treatment of cancer and identification of targets that confer resistance to treatment of cancer. The present invention also relates to identification of parallel drug targets for facilitating an effective long-term treatment strategy and to identifying patients that would benefit from such treatment.

The practice of the present invention will employ, unless otherwise indicated, conventional techniques of molecular biology, immunology, microbiology, cell biology and recombinant DNA, which are within the skill of the art. See e.g., Sambrook, Fritsch and Maniatis, MOLECULAR CLONING: A LABORATORY MANUAL, (Current Edition); CURRENT PROTOCOLS IN MOLECULAR BIOLOGY (F. M. Ausubel et al. eds., (Current Edition)); the series METHODS IN ENZYMOLOGY (Academic Press, Inc.); PCR 2: A PRACTICAL APPROACH (Current Edition); ANTIBODIES, A LABORATORY MANUAL and ANIMAL CELL CULTURE (R. I. Freshney, ed. (1987)). DNA Cloning: A Practical Approach, vol. I & II (D. Glover, ed.); Oligonucleotide Synthesis (N. Gait, ed., Current Edition); Nucleic Acid Hybridization (B. Hames & S. Higgins, eds., Current Edition); Transcription and Translation (B. Hames & S. Higgins, eds., Current Edition); Fundamental Virology, 2nd Edition, vol. I & II (B. N. Fields and D. M. Knipe, eds.)

MAPK Pathway

The mitogen-activated protein kinase (MAPK) cascade is a critical intracellular signaling pathway that regulates signal transduction in response to diverse extracellular stimuli, including growth factors, cytokines, and proto-oncogenes. Activation of this pathway results in transcription factor activation and alterations in gene expression, which ultimately lead to changes in cellular functions including cell proliferation, cell cycle regulation, cell survival, angiogenesis and cell migration. Classical MAPK signaling is initiated by receptor tyrosine kinases at the cell surface, however many other cell surface molecules are capable of activating the MAPK cascade, including integrins, heterotrimeric G-proteins, and cytokine receptors.

Ligand binding to a cell surface receptor, e.g., a receptor tyrosine kinase, typically results in phosphorylation of the receptor. The adaptor protein Grb2 associates with the phosphorylated intracellular domain of the activated receptor, and this association recruits guanine nucleotide exchange factors including SOS-I and CDC25 to the cell membrane. These guanine nucleotide exchange factors interact with and activate the GTPase Ras. Common Ras isoforms include K-Ras, N-Ras, H-Ras and others. Following Ras activation, the serine/threonine kinase Raf (e.g., A-Raf, B-Raf, C-Raf or Raf-1) is recruited to the cell membrane through interaction with Ras or in a Ras independent manner in the cytosol where it undergoes conformational changes and binding to scaffold proteins such as 14-3-3 (King et al., *Nature* 396; 180-183 (1998); Chaudhary et al., *Curr Biol* 10: 551-554 (2000); Avruch et al., *Endo Rev* 56: 127-156 (2001), Wellbrock et al., *Nat Rev Mol Cell Biol* 5: 875-885 (2004). 14-3-3 binding and stabilization/activation of CRAF is governed by phosphorylation of activating residues such as S338, Y341 in the negative charge regulatory region (N-region) and S621 in the C-terminus, outside the kinase domain and dephosphorylation of negative regulatory residues such as S259 in the CR2 domain (FIG. 1C) and numerous other phosphorylation sites distributed throughout the protein which further reflects its complex regulation (Avruch et al., Id. (2001); Wellbrock et al., Id. (2004); Garnett et al., *Mol. Cell* 20: 963-969 (2005). CRAF activation is also induced by artificial homodimer formation (Avruch et al., Id. (2001); Wellbrock et al., Id., (2004).)

Raf is then phosphorylated. Raf directly activates MEK1 and MEK2 by phosphorylation of two serine residues at positions 217 and 221. Following activation, MEK1 and MEK2 phosphorylate tyrosine (Tyr-185) and threonine (Thr-183) residues in serine/threonine kinases Erk1 and Erk2, resulting in Erk activation. Activated Erk regulates many targets in the cytosol and also translocates to the nucleus, where it phosphorylates a number of transcription factors regulating gene expression. Erk kinase has numerous targets, including Elk-I, c-EtsI, c-Ets2, p90RSKI, MNK1, MNK2, MSKI, MSK2 and TOB. While the foregoing pathway is a classical representation of MAPK signaling, there is considerable cross talk between the MAPK pathway and other signaling cascades.

Aberrations in MAPK signaling have a significant role in cancer biology. Altered expression of Ras is common in many cancers, and activating mutations in Ras have also been identified. Such mutations are found in up to 30% of all cancers, and are especially common in pancreatic (90%) and colon (50%) carcinomas. In addition, activating B-Raf mutations have been identified in melanoma and ovarian cancer. The most common mutation, $BRAF^{V600E}$, results in constitutive activation of the downstream MAP kinase pathway and is required for melanoma cell proliferation, soft agar growth, and tumor xenograft formation. CRAF amplification have been implicated in prostate cancer and bladder cancer (Edwards et al., 2003; Simon et al., 2001), besides chromosomal translocations in stomach cancer and pilocytic astrocytomas (Shimizu et al., 1986; Jones et al., 2009). However, the occurrence rate of CRAF mutations in human cancers is 1% (COSMIC) which is attributable to its low basal kinase activity when compared to BRAF (Marais et al., *Science* 280: 109-112 (1997); Emuss et al., *Cancer Res* 65: 9719-9726 (2005); Garnett et al., *Mol. Cell* 20: 963-969 (2005)).

Based on the defined role of MAPK over-activation in human cancers, targeting components of the MAPK pathway with specific inhibitors is a promising approach to cancer therapy. MAPK pathway inhibitors include, but are not limited to, RAF inhibitors, MEK inhibitors and ERK inhibitors. However, patients may have innate resistance or acquire resistance to these promising therapies. Identification of resistance conferring mutations in target kinases, diagnostic and/or prognostic markers and treatment therapies for these patients with innate or acquired resistance are described below.

ERK Mutations

While treatment of cancer with RAF inhibitors or MEK inhibitors is a promising therapeutic approach, patients receiving such therapies frequently relapse or fail to respond, and as a result the patients' disease progresses. As described herein, the present invention relates to the discovery of mutations in ERK (ERK1, ERK2) that confer resistance to a first MAPK pathway inhibitor such as ERK inhibitors, RAF inhibitors, and/or MEK inhibitors, some of which are currently in clinical development. Acquisition of such a mutation in cancer cells makes cells of the patient resistant to treatment with certain MAPK pathway inhibitors. In exemplary embodiments, the invention regards development of resistance to RAF inhibitors, that may include but are not limited to RAF265, vemurafenib (PLX 4032), dabrafenib (Tufinlar®, GSK2118436), sorafenib, SB590885, LGX818, PLX8394, PLX4720, ARQ 736, BMS-908662 (XL218) GDC-0879, ZM 336372 and (S)-methyl 1-(4-(3-(5-chloro-2-fluoro-3-(methylsulfonamido)phenyl)-1-isopropyl-1H-pyrazol-4-yl)pyrimidin-2-ylamino)propan-2-ylcarbamate, Regorafenib (BAY 73-4506) and Tivozanib (AV-951). By way of non-limiting example, exemplary RAF inhibitors are shown in Table 1.

Non-limiting examples of MEK inhibitors include trametinib (Mekinist®, GSK1120212), MEK162 (arry-438162), Pimasertib (AS-703026, MSC1936369B), Refametinib (BAY 86-9766), TAK-733, cobimetinib (GDC-0973), GDC-0623, WX-554, selumetinib (AZD6244); CI-1040; PD184352; PD318088, PD98059, PD334581, PD0325901, RDEA119, 6-Methoxy-7-(3-morpholin-4-yl-propoxy)-4-(4-phenoxy-phenylamino)-quinoline-3-carbonitrile; 4-[3-Chloro-4-(1-methyl-1H-imidazol-2-ylsulfanyl)-phenylamino]-6-methoxy-7-(3-morpholin-4-yl-propoxy)-quinoline-3-carbonitrile, RO-4987655 (CH4987655), U0126 and E6201. Exemplary MEK inhibitors are shown in Table 2.

Exemplary ERK inhibitors include, but are not limited to, VX-11e, SCH-772984, GDC-0994, BVD-523 and FR180204 shown in Table 3.

The clinical emergence of mutations in RAF and MEK and reactivation of the MAPK pathway in response to the RAF and MEK inhibitors, suggests that prospectively determining mechanisms of resistance to MAPK pathway inhibitors, such as an ERK inhibitor, before clinical trial begin may inform which patients will respond to therapy, potential markers of resistance and/or best therapies. The failure of RAF inhibitors or MEK inhibitors to elicit durable tumor responses in many malignancies, including melanomas may indicate suboptimal drug potency or pharmacodynamics in the clinical setting. Based on the findings described herein, treatment modalities involving targeted agents in RAF- or MEK-driven tumors may benefit from more potent drugs, altered dosing of existing drugs, or combined ERK, RAF and/or MEK inhibition. These therapeutic innovations, together with robust tumor genomic profiling to stratify patients, should speed the advent of personalized cancer treatment in cancers with "druggable" oncogene mutations.

TABLE 1

| | | Exemplary RAF Inhibitors | |
|---|---|---|---|
| | Name | CAS No. | Structure |
| 1 | RAF265 | | 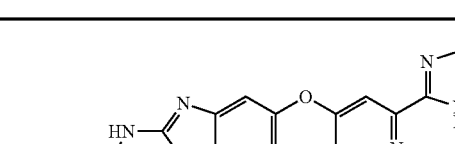 |

TABLE 1-continued
Exemplary RAF Inhibitors
| Name | CAS No. | Structure |
|---|---|---|
| 2 vemurafenib (PLX 4032) | 918504-65-1 | 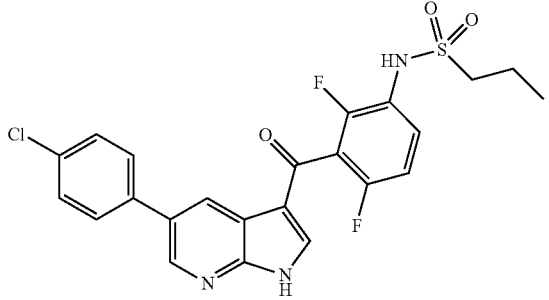 [SMILES: CCCS(=O)(=O)Nc1ccc(F)c(C(=O)c2c[nH]c3ncc(-c4ccc(Cl)cc4)cc23)c1F] |
| 3 dabrafenib (Tufinlar ®, GSK2118436) | | 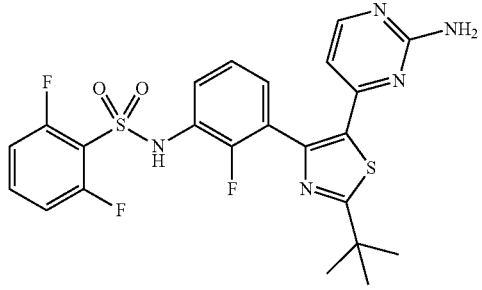 [SMILES: CC(C)(C)c1nc(-c2cccc(NS(=O)(=O)c3c(F)cccc3F)c2F)c(-c2ccnc(N)n2)s1] |
| 4 Sorafenib Tosylate Nexavar Bay 43-9006 | | 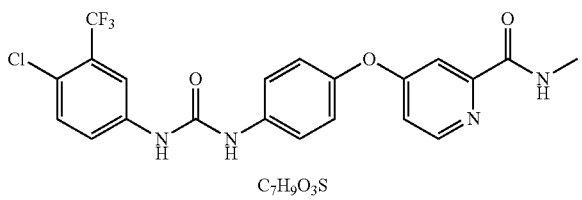 $C_7H_9O_3S$ |
| 5 Sorafenib 4-[4-[[4-chloro-3-(trifluoromethyl)phenyl] carbamoylamino] phenoxy]-N-methyl-pyridine-2-carboxamide | | 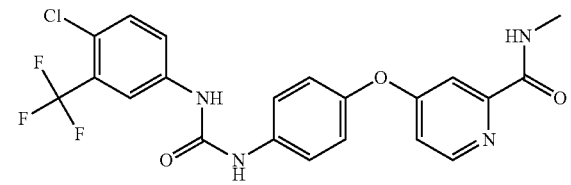 [SMILES: CNC(=O)c1cc(Oc2ccc(NC(=O)Nc3ccc(Cl)c(C(F)(F)F)c3)cc2)ccn1] |
| 6 SB590885 | | 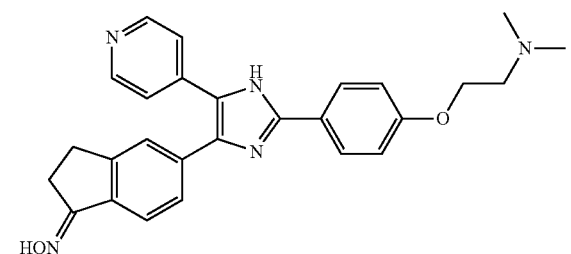 |

TABLE 1-continued

Exemplary RAF Inhibitors

| Name | CAS No. | Structure |
|---|---|---|
| 7 Encorafenib (LGX818) | | 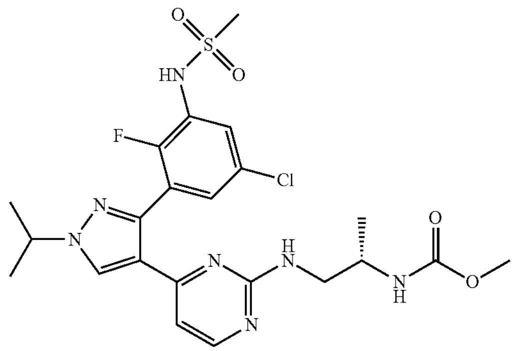 [SMILES: COC(=O)N[C@@H](C)CNc1nccc(-c2cn(C(C)C)nc2-c2cc(Cl)cc(NS(C)(=O)=O)c2F)n1] |
| 8 PLX8394 | | |
| 9 PLX4720 | | 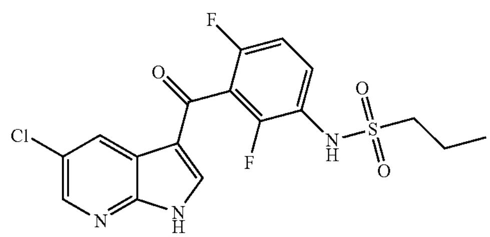 [SMILES: CCCS(=O)(=O)Nc1ccc(F)c(C(=O)c2c[nH]c3ncc(Cl)cc23)c1F] |
| 10 ARQ 736 | 1228237-57-7 | |
| 11 BMS-908662 (XL281) | | 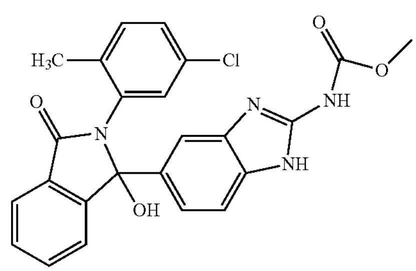 [SMILES: COC(=O)Nc1nc2cc(C3(O)c4ccccc4C(=O)N3c3cc(Cl)ccc3C)ccc2[nH]1] |
| 12 GDC-0879 | | 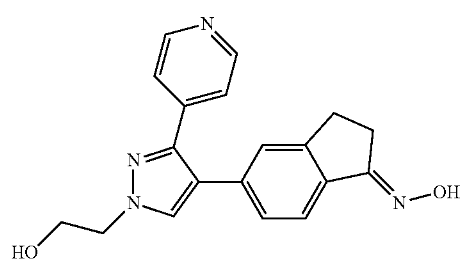 [SMILES: OCCn1cc(-c2ccc3c(c2)CC/C3=N\O)c(-c2ccncc2)n1] |
| 13 ZM 336372 | | 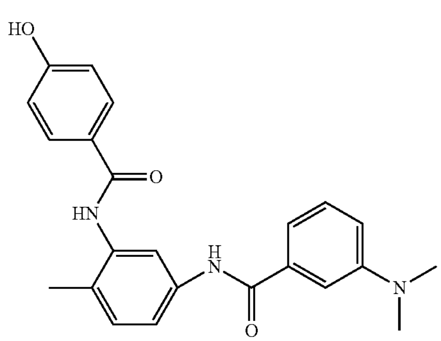 [SMILES: Cc1ccc(NC(=O)c2cccc(N(C)C)c2)cc1NC(=O)c1ccc(O)cc1] |

TABLE 1-continued

Exemplary RAF Inhibitors

| Name | CAS No. | Structure |
|---|---|---|
| 14 Regorafenib (BAY 73-4506) | | |
| 15 Tivozanib (AV-951) | | |

TABLE 2

Exemplary MEK Inhibitors

| Name | CAS No. | Structure |
|---|---|---|
| 1 trametinib | | |
| 2 trametinib dimethylsulfoxide (Mekinist ®, GSK1120212) | 1204531-25-80 | |

TABLE 2-continued

Exemplary MEK Inhibitors

| Name | CAS No. | Structure |
|---|---|---|
| 3 MEK162 (arry-438162) | | (structure) |
| 4 Pimasertib (AS-703026, MSC1936369B) | | (structure) |
| 5 Refametinib (BAY 86-9766) | 923032-37-5 | (structure) |
| 6 TAK-733 | 1035555-63-5 | (structure) |
| 7 cobimetinib (GDC-0973) | | (structure) |

TABLE 2-continued

Exemplary MEK Inhibitors

| Name | CAS No. | Structure |
|---|---|---|
| 8 GDC-0623 | | |
| 9 WX-554 | 1439985-04-2 | |
| 10 Selumetinib (AZD6244) | | |
| 11 CI-1040/PD184352 | | |
| 12 PD0325901 | | |

TABLE 2-continued

Exemplary MEK Inhibitors

| Name | CAS No. | Structure |
|---|---|---|
| 13 PD318088 | | |
| 14 PD98059 | | |
| 15 PD334581 | | |
| 16 N-[3,4-difluoro-2-[(2-fluoro-4-iodophenyl)amino]-6-methoxyphenyl]-1-[(2R)-2,3-dihydroxypropyl]-Cyclopropanesulfonamide | 923032-38-6 | |
| 17 6-Methoxy-7-(3-morpholin-4-yl-propoxy)-4-(4-phenoxy-phenylamino)-quinoline-3-carbonitrile | | |

TABLE 2-continued
Exemplary MEK Inhibitors
| Name | CAS No. | Structure |
|---|---|---|
| 18 4-[3-Chloro-4-(1-methyl-1H-imidazol-2-ylsulfanyl)-phenylamino]-6-methoxy-7-(3-morpholin-4-yl-propoxy)-quinoline-3-carbonitrile | | 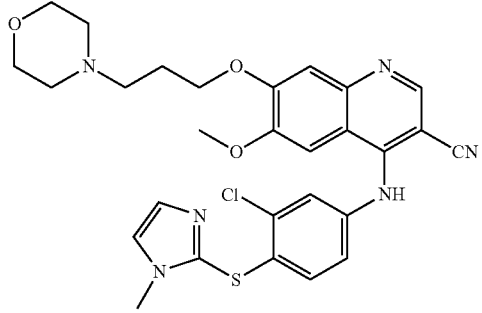 [SMILES: COc1cc2c(Nc3ccc(Sc4nccn4C)c(Cl)c3)c(C#N)cnc2cc1OCCCN1CCOCC1] |
| 19 RO-4987655 (CH4987655) | | 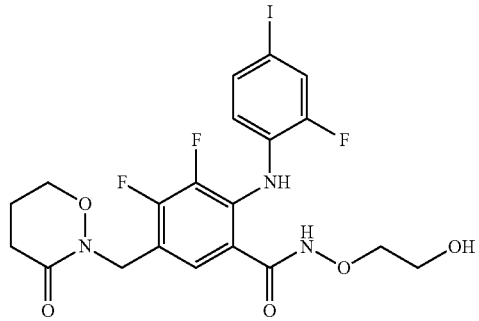 [SMILES: O=C(NOCCO)c1cc(CN2OCCCC2=O)c(F)c(F)c1Nc1ccc(I)cc1F] |
| 20 U0126 | | 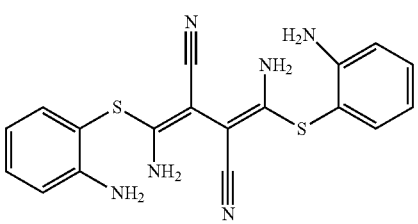 [SMILES: N#CC(=C(/N)Sc1ccccc1N)/C(C#N)=C(\N)Sc1ccccc1N] |
| 21 E6201 | | 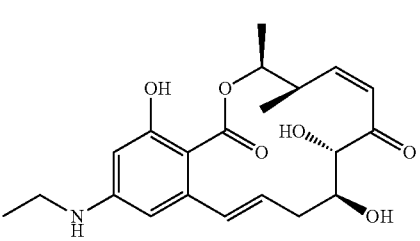 [SMILES: CCNc1cc(O)c2c(c1)/C=C/C[C@H](O)[C@H](O)C(=O)/C=C\[C@@H](C)[C@H](C)OC2=O] |

TABLE 3

Exemplary ERK Inhibitors

| Name | CAS No. | Structure |
|---|---|---|
| 1 VX-11e | | 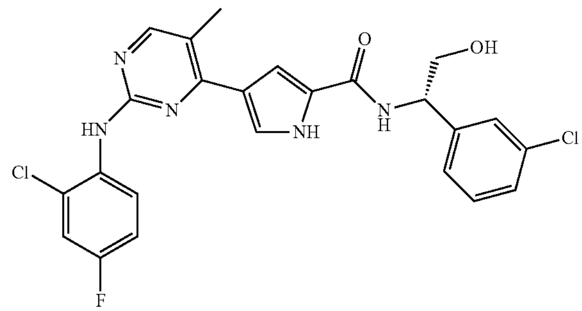 [SMILES: Cc1cnc(Nc2ccc(F)cc2Cl)nc1-c1c[nH]c(C(=O)N[C@H](CO)c2cccc(Cl)c2)c1] |
| 2 SCH-772984 | | 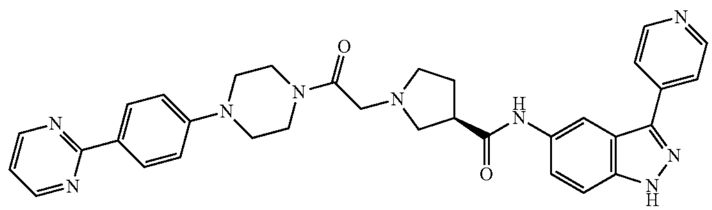 [SMILES: O=C(Nc1ccc2[nH]nc(-c3ccncc3)c2c1)[C@@H]1CCN(CC(=O)N2CCN(c3ccc(-c4ncccn4)cc3)CC2)C1] |
| 3 GDC-0994 | | |
| 4 BVD-523 | | |
| 5 FR180204 | | 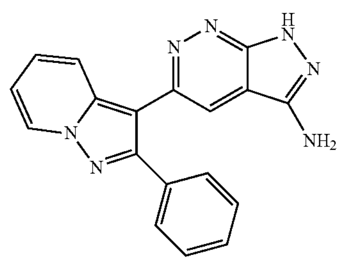 [SMILES: Nc1n[nH]c2nnc(-c3c(-c4ccccc4)nn4ccccc34)cc12] |

In various embodiments, the present invention relates to methods of identifying mutations in an ERK polypeptide, or mutations in a nucleic acid molecule encoding the ERK polypeptide, that confer resistance on cells expressing the ERK polypeptide to drugs that inhibit a MAPK pathway activity such as an ERK, RAF and/or MEK activity. A "mutant ERK polypeptide," as referenced herein, includes an ERK polypeptide including one or more mutations that confer resistance to one or more known MAPK pathway inhibitors. Likewise, a "mutant ERK nucleic acid molecule," as referenced herein, includes a nucleic acid molecule that encodes a mutant ERK polypeptide. Nucleic acid molecules encoding ERK polypeptides that include one or more mutations can be created using any suitable method known in the art, including, for example, random mutagenesis or site-directed mutagenesis of a wild-type ERK nucleic acid sequence, which can be conducted in E. coli. In exemplary embodiments, the wild-type ERK nucleic acid sequence is a human wild-type ERK1 or ERK2 nucleic acid sequence. In specific embodiments, the wild-type ERK1 nucleic acid sequence is wild-type human ERK1 (SEQ ID NO: 1) or ERK2 (SEQ ID NO: 2). The mutant ERK1/2 nucleic acid molecules can then be screened in cells otherwise sensitive to treatment with the first MAPK pathway inhibitor such as an ERK inhibitor, a RAF inhibitor and/or a MEK inhibitor to identify a nucleic acid that encodes a mutant ERK1/2 polypeptide compared to a wild-type ERK1/2 polypeptide that is resistant to treatment with the MAPK pathway inhibitor. In some embodiments, the ERK polypeptide is the wild-type human ERK1 (SEQ ID NO: 3) or ERK2 (SEQ ID NO: 4).

Any suitable method can be used to screen mutant ERK nucleic acids and mutant ERK polypeptides for resistance to treatment with a first MAPK pathway inhibitor. For example, a nucleic acid molecule encoding a mutant ERK polypeptide can be expressed in cells otherwise sensitive to treatment with a MAPK pathway inhibitor. An exemplary cell line useful for this purpose is the melanoma cell line A375. Following expression of the mutant ERK polypeptide, the cells can be treated with a MAPK pathway inhibitor, such as an ERK inhibitor, a RAF inhibitor and/or a MEK inhibitor. The activity of the mutant ERK polypeptide can then be measured and compared to the activity of a wild-type ERK polypeptide similarly expressed and treated with the same inhibitor(s). Activity of an ERK polypeptide can be determined by, for example, measuring proliferation or viability of cells following treatment with the MAPK pathway inhibitor, wherein proliferation or viability are positively correlated with ERK activity. Cell growth, proliferation, or viability can be determined using any suitable method known in the art. In one embodiment, cell growth can be determined using well-based cell proliferation/viability assays such as MTS or Cell Titer GLo, in which cell growth in the presence of a MAPK pathway inhibitor is expressed as a percentage of that observed in untreated cells cultured in the absence of the MAPK pathway inhibitor. In certain embodiments, resistance is defined as a shift in the GI50 value of at least 2 fold, more preferably at least 3 fold, most preferably at least 4-5 fold, with respect to a suitable control. In other embodiments, resistance is defined as a GI50 value of ~1 uM). Activity of an ERK polypeptide can also be measured by, for example, determining the relative amount of phosphorylated ERK1/2 present in the cell following treatment with the MAPK pathway inhibitor. Activity of a wild-type or mutant ERK polypeptide can also be determined using an in vitro phosphorylation assay. A mutant ERK polypeptide having greater activity than a wild-type ERK polypeptide following treatment with a MAPK pathway inhibitor is identified as containing a mutation that confers resistance to a MAPK pathway inhibitor. The mutation conferring resistance to a MAPK pathway inhibitor can then be identified by sequencing the nucleic acid encoding the mutant ERK polypeptide, or by sequencing the mutant ERK polypeptide directly.

In this manner, as well as using massively parallel sequence methods, as described in an example below, amino acid substitutions were identified in the ERK polypeptide that when mutated confer resistance to ERK inhibitors, RAF inhibitors and/or MEK inhibitors. In particular, substitutions at one or more of the following amino acids of the human ERK1 polypeptide confer resistance to ERK inhibitors including I48, Y53, G54, S74, P75, Y81, C82, and G186. In some embodiments, the one or more substitutions is selected from one resistance mutation in ERK1, one or more substitutions from any two of I48, Y53, G54, S74, P75, Y81, C82, and G186, one or more substitutions from any three of I48, Y53, G54, S74, P75, Y81, C82, and G186, one or more substitutions from any four of I48, Y53, G54, S74, P75, Y81, C82, and G186 or one or more substitutions from any five of I48, Y53, G54, S74, P75, Y81, C82, and G186. In some embodiments, the mutant ERK1 polypeptide includes one or more of the following resistance mutations: I48N, Y53H, G54A, S74G, P75L, Y81C, C82Y, and G186D. Substitutions at one or more of the following amino acids of the human ERK2 polypeptide confer resistance to ERK inhibitors including Y36, G37, P58, Y64, and C65. In some embodiments, the one or more substitutions is selected from on resistance mutation in ERK2, one or more substitutions from any two of Y36, G37, P58, Y64, and C65, one or more substitutions from any three of Y36, G37, P58, Y64, and C65, one or more substitutions from any four of Y36, G37, P58, Y64, and C65. In some embodiments, the mutant ERK2 polypeptide includes one or more of the following resistance mutations: Y36H, Y36N, G37S, P58L, P58S, Y64N, and C65Y. Substitutions at one or more of the following amino acids of the human ERK1 polypeptide confer resistance to RAF inhibitors, MEK inhibitors or RAF and MEK inhibitors including C82, R84, Q90, Y148, A206, and S219. In some embodiments, the one or more substitutions is selected from one resistance mutation in ERK1, one or more substitutions from any two of C82, R84, Q90, Y148, A206, and S219, one or more substitutions from any three of C82, R84, Q90, Y148, A206, and S219, one or more substitutions from any four of C82, R84, Q90, Y148, A206, and S219 or one or more substitutions from any five of C82, R84, Q90, Y148, A206, and S219. In some embodiments, the mutant ERK1 polypeptide includes one or more of the following resistance mutations: C82Y, R84H, Q90R, Y148H, A206V, and S219P. Substitutions at one or more of the following amino acids of the human ERK2 polypeptide confer resistance to RAF inhibitors, MEK inhibitors or RAF and MEK inhibitors including Y131, A189, S202, D321, and E322. In some embodiments, the one or more substitutions is selected from one resistance mutation in ERK2, one or more substitutions from any two of Y131, A189, S202, D321, and E322, one or more substitutions from any three of Y131, A189, S202, D321, and E322, and one or more substitutions from any four of Y131, A189, S202, D321, and E322. In some embodiments, the mutant ERK2 polypeptide includes one or more of the following resistance mutations: Y131F, A189V, S202P, D321G, D321N, and E322K.

Isolated Nucleic Acid Molecules

The present invention concerns polynucleotides or nucleic acid molecules relating to the ERK gene and its respective gene product. These polynucleotides or nucleic acid molecules are isolatable and purifiable from mammalian cells. In particular aspects of the invention, the isolated ERK nucleic acid molecules described herein comprise a mutation conferring resistance to one or more MAPK pathway inhibitors. A "mutant ERK nucleic acid molecule," as referenced herein, includes an ERK nucleic acid molecule that encodes a mutant ERK polypeptide, i.e., an ERK1 and/or ERK2 polypeptide including one or more mutations that confer resistance to one or more MAPK pathway inhibitors.

It is contemplated that an isolated and purified ERK nucleic acid molecule, e.g., a mutant ERK nucleic acid molecule, can take the form of RNA or DNA. As used herein, the term "RNA transcript" refers to an RNA molecule that is the product of transcription from a DNA nucleic acid molecule. Such a transcript can encode for one or more proteins.

As used in this application, the term "polynucleotide" refers to a nucleic acid molecule, RNA or DNA, that has been isolated, such as being free of total genomic nucleic acid. Therefore, a "polynucleotide encoding ERK" refers to a nucleic acid segment that includes ERK coding sequences, yet is isolated away from, or purified and free of, total genomic DNA and proteins. When the present application refers to the function or activity of an ERK-encoding polynucleotide or nucleic acid, it is meant that the polynucleotide encodes a molecule that is capable of performing an activity of a wild-type ERK polypeptide.

The term "cDNA" is intended to refer to DNA prepared using RNA as a template. It also is contemplated that a given ERK-encoding nucleic acid or ERK gene from a given cell may be represented by natural variants or strains that have slightly different nucleic acid sequences but, nonetheless, encode an active ERK polypeptide. In a particular embodiment, the active ERK polypeptide is an active human ERK polypeptide. In some embodiments, the active ERK polypeptide is a mutant C-RAF polypeptide that has an activity of a wild-type ERK polypeptide, but which is resistant to one or more known MAPK pathway inhibitors. Consequently, certain aspects of the present invention encompass derivatives of ERK nucleic acids or polypeptides with minimal nucleic acid or amino acid changes, but that possess the same biological function.

In some embodiments, the invention relates to recombinant vectors incorporating DNA sequences that encode mutant ERK polypeptides or peptides that include within its amino acid sequence a contiguous amino acid sequence in accordance with, or essentially corresponding to mutant ERK polypeptides. In exemplary embodiments, the invention relates to isolated DNA segments and recombinant vectors incorporating DNA sequences that encode an ERK polypeptide that includes within its amino acid sequence a contiguous amino acid sequence of an ERK polypeptide comprising one or more mutations that confer resistance to one or more MAPK pathway inhibitors.

The nucleic acid segments used in the present invention, regardless of the length of the coding sequence itself, can be combined with other DNA or RNA sequences, such as promoters, polyadenylation signals, additional restriction enzyme sites, multiple cloning sites, other coding segments, and the like, such that their overall length can vary considerably. It is therefore contemplated that a nucleic acid fragment of almost any length can be employed, with the total length preferably being limited by the ease of preparation and use in the intended recombinant DNA protocol. A "heterologous" sequence refers to a sequence that is foreign or exogenous to the remaining sequence. A heterologous gene refers to a gene that is not found in nature adjacent to the sequences with which it is now placed.

In some embodiments, the nucleic acid sequence may encode a mutant ERK polypeptide having ERK activity where at least one amino acid substitution occurs at one or more amino acid positions of ERK1 including the following: I48, Y53, G54, S74, P75, Y81, C82, R84, Q90, Y148, G186, A206 and S219. In some embodiments, the mutant ERK1 polypeptide includes one or more of the following resistance mutations: I48N, Y53H, G54A, S74G, P75L, Y81C, C82Y, R84H, Q90R, Y148H, G186D, A206V and S219P. In some embodiments, the nucleic acid sequence may encode a mutant ERK polypeptide having ERK activity where at least one amino acid substitution occurs at one or more amino acid positions of ERK2 including the following: Y36, G37, P58, Y64, C65, Y131, A189, S202, D321, and E322. In some embodiments, the mutant ERK2 polypeptide includes one or more of the following resistance mutations: Y36H, Y36N, G37S, P58L, P58S, Y64N, C65Y, Y131F, A189V, S202P, D321G, D321N, and E322K.

Expression Vectors and Host Cells

The present invention encompasses expression vector compositions and the use of such vectors to encode for an ERK polypeptide, e.g., a mutant ERK polypeptide, as well as host cell compositions into which such expression vectors have been introduced. The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques.

The term "expression vector" or "expression construct" refers to a vector containing a nucleic acid sequence coding for at least part of a gene product capable of being transcribed. In some cases, RNA molecules are then translated into a protein, protein, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors can contain nucleic acid sequences that serve other functions as well.

As used herein, the terms "cell," "cell line," and "cell culture" may be used interchangeably. A cell comprising an ERK polynucleotide, either mutated or wild-type, can be employed in the invention. All of these terms also include their progeny, which refers to any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organisms that is capable of replicating a vector and/or expressing a heterologous gene encoded by a vector. A host cell can, and has been, used as a recipient for vectors. A host cell may be "transfected" or "transformed," which refers to a process by which exogenous nucleic acid is transferred or introduced into the host cell. A transformed cell includes the primary subject cell and its progeny. A "recombinant host cell" refers to a host cell that carries a recombinant nucleic acid, i.e. a nucleic acid that has been manipulated in vitro or that is a replicated copy of a nucleic acid that has been so manipulated. A host cell can be derived from prokaryotes or eukaryotes, depending upon whether the desired result is replication of the vector, expression of part or all of the vector-encoded nucleic acid sequences, or production of infectious viral particles.

Isolated Polypeptide Molecules

Another aspect of the invention pertains to isolated and/or purified ERK polypeptides, and biologically active portions thereof. In particular aspects of the invention, the ERK polypeptides described herein comprise a mutation at one or more amino acids conferring resistance to one or more RAF inhibitors. A "mutant ERK polypeptide", as referenced herein, includes a ERK polypeptide including a mutation at one or more amino acids positions that confer resistance to one or more MAPK pathway inhibitors.

Biologically active portions of an ERK polypeptide include peptides comprising amino acid sequences derived from the amino acid sequence of an ERK polypeptide, e.g., the amino acid sequence shown in SEQ ID NO: 3 or SEQ ID NO:4, which include fewer amino acids than a full length ERK polypeptide, and exhibit at least one activity of an ERK polypeptide. Typically, biologically active portions (peptides, e.g., peptides which are, for example, 5, 10, 15, 20, 30, 35, 36, 37, 38, 39, 40, 50, 100 or more amino acids in length) comprise a domain or motif with at least one activity of an ERK polypeptide. Moreover, other biologically active portions, in which other regions of the protein are deleted, can be prepared by recombinant techniques and evaluated for one or more of the activities described herein. Preferably, the biologically active portions of an ERK polypeptide include one or more selected domains/motifs or portions thereof having biological activity.

ERK polypeptides may be produced by recombinant DNA techniques. For example, a nucleic acid molecule encoding the protein is cloned into an expression vector (as described above), the expression vector is introduced into a host cell (as described above) and the ERK polypeptide is expressed in the host cell. The ERK polypeptide can then be isolated from the cells by an appropriate purification scheme using standard protein purification techniques. Alternative to recombinant expression, an ERK polypeptide can be synthesized chemically using standard peptide synthesis techniques. Moreover, a native ERK polypeptide and/or a mutant ERK polypeptide can be isolated from cells (e.g., cancer cells), for example using an anti-ERK antibody, which can be produced by standard techniques utilizing a ERK polypeptide or fragment thereof of this invention.

ERK chimeric or fusion proteins may also be used. As used herein, an ERK "chimeric protein" or "fusion protein" comprises an ERK polypeptide operatively linked to a non-ERK polypeptide. An "ERK polypeptide" refers to a protein having an amino acid sequence corresponding to an ERK polypeptide, whereas a "non-ERK polypeptide" refers to a protein having an amino acid sequence corresponding to a protein which is not substantially homologous to the ERK polypeptide, e.g., a protein which is substantially different from the ERK polypeptide, which does not display an ERK activity and which is derived from the same or a different organism. Within the fusion protein, the term "operatively linked" is intended to indicate that the ERK polypeptide and the non-ERK polypeptide are fused in-frame to each other. The non-ERK polypeptide can be fused to the N-terminus or C-terminus of the ERK polypeptide. For example, in one embodiment the fusion protein is a GST-ERK fusion protein in which the ERK amino acids are fused to the C-terminus of the GST polypeptide. Such fusion proteins can facilitate the purification of recombinant ERK polypeptide. In another embodiment, the fusion protein is an ERK polypeptide containing a heterologous signal sequence at its N-terminus. In certain host cells (e.g., mammalian host cells), expression and/or secretion of an ERK protein can be increased through use of a heterologous signal sequence.

Mutant ERK polypeptide can be generated by mutagenesis of a wild-type ERK polypeptide, or of the nucleic acid molecule encoding a wild-type ERK polypeptide. Mutant ERK polypeptide can also be identified by screening combinatorial libraries of ERK mutants for a mutant ERK polypeptide having a desired activity, e.g., resistance to one or more MAPK pathway inhibitors. Several techniques are known in the art for screening gene products of combinatorial libraries made by point mutations or truncation, and for screening cDNA libraries for gene products having a selected property. Such techniques are adaptable for rapid screening of the gene libraries generated by combinatorial mutagenesis. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected.

Antibodies

The polypeptides expressed from the polynucleotides of the invention can be used for generating antibodies. In some embodiments, the antibodies can be used to detect and quantitate expression of the mutant ERK polypeptides. In some embodiments, the antibodies can be used to alter the activity of a mutant ERK polypeptide. Polypeptides expressed from the polynucleotides of the invention comprising at least six, eight, ten, twelve, fifteen, twenty or thirty consecutive amino acids can be used as immunogens. The polypeptides can be used to obtain a preparation of antibodies which specifically bind to a mutant ERK polypeptide of the invention having one or more amino acid substitutions at one or more of the following amino acids of the human ERK polypeptide that confer resistance to MAPK pathway inhibitors at least one amino acid substitution occurs at one or more amino acid positions of ERK1 including the following: I48, Y53, G54, S74, P75, Y81, C82, R84, Q90, Y148, G186, A206 and S219 and/or at least one amino acid substitution occurs at one or more amino acid positions of ERK2 including the following: Y36, G37, P58, Y64, C65, Y131, A189, S202, D321, and E322. In some embodiments, the mutant ERK1 polypeptide includes one or more of the following resistance mutations: I48N, Y53H, G54A, S74G, P75L, Y81C, C82Y, R84H, Q90R, Y148H, G186D, A206V and S219P. In some embodiments, the mutant ERK2 polypeptide includes one or more of the following resistance mutations: Y36H, Y36N, G37S, P58L, P58S, Y64N, C65Y, Y131F, A189V, S202P, D321G, D321N, and E322K.

The antibodies can be monoclonal and polyclonal antibodies, single chain antibodies, chimeric antibodies, bifunctional/bispecific antibodies, humanized antibodies, human antibodies, and complementary determining region (CDR)-grafted antibodies, that are specific for the target protein or fragments thereof; and also include antibody fragments, including Fab, Fab', F(ab')2, scFv, Fv, camelbodies, or microantibodies. An antibody can also refer to an anti-idiotype antibody, i.e., an antibody directed against the antigen specific part of the sequence of an antibody and thus recognizes the binding sites of other antibodies; or an anti-anti-idiotype antibody, i.e., an antibody with a combining site that mimics the epitope on the antigen that was used to generate the original antibody. Techniques for raising antibodies are well known in the art.

Single chain antibodies can also be constructed. Single chain antibodies which specifically bind to a polypeptide expressed from the polynucleotides of the invention can be isolated, for example, from single-chain immunoglobulin display libraries, as are known in the art. The library is "panned" against a polypeptide, and a number of single chain antibodies which bind different epitopes of the polypeptide with high-affinity can be isolated. Hayashi et al., 1995, *Gene* 160: 129-30. Such libraries are known and available to those in the art. The antibodies can also be constructed using the polymerase chain reaction (PCR), using hybridoma cDNA as a template. Thirion et al., 1996, *Eur. J. Cancer Prev.* 5: 507-11.

The single chain antibody can be mono- or bi-specific, and can be bivalent or tetravalent. Construction of tetravalent bispecific single chain antibodies is taught in Coloma and Morrison, 1997, *Nat. Biotechnol.* 15: 159-63 Construction of bivalent bispecific single chain antibodies is taught in Mallender and Voss, 1994, *J. Biol. Chem.* 269: 199-206.

A nucleotide sequence encoding the single chain antibody can then be constructed using manual or automated nucleotide synthesis, cloned into DNA expression vectors using standard recombinant DNA methodologies, and introduced into cells which express the selected gene, as described below. Alternatively, the antibodies can be produced directly using filamentous phage technology Verhaar et al., 1995, *Int. J. Cancer* 61:497-501; Nicholls et al., 1993. *J. Immunol. Meth.* 165:81-91.

The antibodies bind specifically to the epitopes of the polypeptides expressed from the polynucleotides of the invention. In a preferred embodiment, the epitopes are not present on other human proteins. Typically a minimum number of contiguous amino acids to encode an epitope is 6, 8, or 10. However, more can be used, for example, at least 15, 25, or 50, especially to form epitopes which involve non-contiguous residues or particular conformations.

Antibodies that bind specifically to the polypeptides include those that bind to full-length polypeptides. Specific binding antibodies do not detect other proteins on Western blots of human cells, or provide a signal at least ten-fold lower than the signal provided by the target protein of the invention. Antibodies which have such specificity can be obtained by routine screening. In a preferred embodiment of the invention, the antibodies immunoprecipitate the polypeptides expressed from the polynucleotides of the invention from cell extracts or solution. Additionally, the antibodies can react with polypeptides expressed from the polynucleotides of the invention in tissue sections or on Western blots of polyacrylamide gels. Preferably the antibodies do not exhibit nonspecific cross-reactivity with other human proteins on Western blots or in immunocytochemical assays.

Techniques for purifying antibodies to the polypeptides expressed from the polynucleotides of the invention are available in the art. In a preferred embodiment, the antibodies are passed over a column to which a particular protein or polypeptide expressed from the polynucleotides of the invention is bound. The bound antibodies are then eluted, for example, with a buffer having a high salt concentration.

Detection of Mutations

In another aspect, the invention pertains to methods of detecting the presence of a mutant ERK polypeptide in a sample (e.g., a biological sample from a cancer patient). A variety of screening methods can be used to detect the presence of a mutant ERK polypeptide of the invention in a sample, e.g., a nucleic acid and/or a protein sample. In specific embodiments, the sample includes a cell or cell extract. In exemplary embodiments, the sample is obtained from a subject, e.g., a subject having cancer.

Methods for detecting the presence of resistance mutations in genomic DNA, cDNA, and RNA (i.e., mRNA) containing a sequence encoding an ERK polypeptide, or biologically active portion thereof, can be used within the scope of the present invention. Likewise, methods for detecting the presence of resistance mutations in the ERK polypeptide, or biologically active portions thereof, can be used within the scope of the present invention. In particular embodiments, methods including, but not limited to, the following can be used to detect the presence of an ERK polypeptide, or a nucleic acid molecule encoding an ERK polypeptide, having a mutation at one or more amino acid positions as compared to the wild-type ERK1 polypeptide (SEQ ID NO: 3) and/or ERK2 polypeptide (SEQ ID NO: 4). In some embodiments, antibodies directed to a mutant ERK polypeptide may be used to detect the presence of the mutant polypeptide.

Point mutations can be detected using any suitable method known in the art, including, for example, denaturing gradient gel electrophoresis ("DGGE"), restriction fragment length polymorphism analysis ("RFLP"), chemical or enzymatic cleavage methods, direct sequencing of target regions amplified by PCR (see above), single-strand conformation polymorphism analysis ("SSCP"), polymerase chain reaction, sequencing, hybridization, or "hybrid capture" followed by pyrosequencing or single-molecule sequencing. Other methods for detecting mutations known to one skilled in the art may also be used.

Screening methods can be performed to screen an individual for the occurrence of the mutations identified above. For example, in one embodiment, a sample (such as blood or other bodily fluid or cell or tissue sample) is taken from a patient for analysis. In an exemplary embodiment, the patient is a cancer patient. Methods suitable for processing such samples for detection of a mutation in an ERK nucleic acid or an ERK polypeptide are known in the art, and the skilled artisan may adapt the processing of such samples in accordance with the chosen method of detection.

The presence or absence of one or more mutations described herein determines the likelihood of the screened individuals to resist therapy with a MAPK pathway inhibitor. According to methods provided by the invention, these results will be used to adjust and/or alter the dose of the MAPK pathway inhibitor, or to select a course of treatment using a second inhibitor. In some embodiments, the second inhibitor may be a MAPK pathway inhibitor that is different than the first MAPK pathway inhibitor to which resistance developed. In some embodiments, the second MAPK pathway inhibitor may be an ERK inhibitor, a RAF inhibitor and/or a MEK inhibitor. In some embodiments, the first MAPK pathway inhibitor may be stopped and the endogenous expression of ERK in the cancer may be effective treatment for the cancer. Effective treatment of a subject having cancer can comprise the eradication of a cancer cell, the cessation or reduction of cancer (such as solid tumor) growth rate, or the amelioration of at least one cancer symptom.

The resistance mutations in an ERK polypeptide, or in nucleic acid molecules encoding an ERK polypeptide, can be detected using any suitable methods known in the art, or modifications thereof, including the methods described below. Such methods include the use of allele-specific polymerase chain reaction, direct or indirect sequencing of the site, the use of restriction enzymes where the respective alleles of the site create or destroy a restriction site, the use of allele-specific hybridization probes, the use of antibodies that are specific for the mutant ERK polypeptide, or any other biochemical interpretation.

Diagnostic/Prognostic Markers for Resistance to Targeted Therapies

In some aspects, the present invention relates to methods of detecting the presence of one or more diagnostic or prognostic markers in a sample (e.g. a biological sample from a cancer patient). A variety of screening methods known to one of skill in the art may be used to detect the presence of the marker in the sample including DNA, RNA and protein detection. The techniques can be used to determine the presence or absence of a mutation in a sample obtained from a patient. In some embodiments, the patient may have innate or acquired resistance to kinase targeted therapies, including MAPK pathway inhibitors. For example, the patient may have an innate or acquired resistance to a RAF inhibitor or a MEK inhibitor (such as the inhibitors shown in Tables 1 and 2). In one embodiment, identification of an ERK nucleic acid or polypeptide including one or more mutations described herein in a cancer-cell containing sample obtained from a patient indicates that the patient is at a relatively high risk of relapse or lack of response to treatment with a MAPK pathway inhibitor. Identification of one or more ERK mutations described above in a patient assists the physician in determining and implementing a treatment protocol for the patient. For example, in a patient having one or more mutations in the ERK polypeptide identified above, the physician may treat the patient with a specific inhibitor based on the mutated amino acid or a combination therapy as described in more detail below.

Identification of resistance mutations in the ERK polypeptide also allows for the screening of patients having a cancer in order to determine the presence or absence of an ERK resistance mutation at one or more amino acid positions in the cancer. Determining the presence or absence of one or more ERK resistance mutations in a cancer allows for alteration of the treatment strategy of a cancer patient. Such alterations can include, for example, starting or stopping treatment with an ERK inhibitor, a RAF inhibitor and/or a MEK inhibitor, giving a combination therapy, providing sequential dosing of a first MAPK pathway inhibitor and a second MAPK pathway inhibitor and the like.

In some embodiments, the ERK resistance mutations may be identified in a nucleic acid encoding a mutant ERK polypeptide having ERK activity, where the mutant ERK polypeptide includes at least one amino acid substitution as compared to a wild type ERK1 polypeptide shown in SEQ ID NO: 3 and/or the ERK2 polypeptide shown in SEQ ID NO: 4 and where the at least one amino acid substitution confers resistance to one or more MAPK pathway inhibitors on a cell expressing the mutant ERK polypeptide. In some embodiments, the at least one amino acid substitution that confers resistance occurs at one or more amino acid positions of ERK1 including the following: I48, Y53, G54, S74, P75, Y81, C82, R84, Q90, Y148, G186, A206 and S219 and/or the at least one amino acid substitution that confers resistance occurs at one or more amino acid positions of ERK2 including the following: Y36, G37, P58, Y64, C65, Y131, A189, S202, D321, and E322. In some embodiments, the mutant ERK1 polypeptide includes one or more of the following resistance mutations: I48N, Y53H, G54A, S74G, P75L, Y81C, C82Y, R84H, Q90R, Y148H, G186D, A206V and S219P. In some embodiments, the mutant ERK2 polypeptide includes one or more of the following resistance mutations: Y36H, Y36N, G37S, P58L, P58S, Y64N, C65Y, Y131F, A189V, S202P, D321G, D321N, and E322K.

Methods of Treatment

In various embodiments, the invention provides methods for treatment of a patient having cancer. The methods generally comprise administration of a first inhibitor and a second inhibitor. One inhibitor may be an ERK inhibitor, a RAF inhibitor and or a MEK inhibitor. Exemplary ERK, RAF and MEK inhibitors are shown in Tables 1-3 above. In some embodiments, a combination therapy for cancer is provided, comprising an effective amount of a first MAPK pathway inhibitor and an effective amount of a second MAPK pathway inhibitor.

In exemplary embodiments of the foregoing aspects, the RAF inhibitor provided herein can be RAF265, vemurafenib (PLX 4032), dabrafenib (Tufinlar®, GSK2118436), sorafenib, SB590885, LGX818, PLX8394, PLX4720, ARQ 736, BMS-908662 (XL218) GDC-0879, ZM 336372 and (S)-methyl 1-(4-(3-(5-chloro-2-fluoro-3-(methylsulfonamido)phenyl)-1-isopropyl-1H-pyrazol-4-yl)pyrimidin-2-ylamino)propan-2-ylcarbamate, Regorafenib (BAY 73-4506) and Tivozanib (AV-951) or combinations thereof. Additional RAF inhibitors known in the art may also be used.

As a non-limiting example, the MEK inhibitor provided herein can be trametinib (Mekinist®, GSK1120212), MEK162 (arry-438162), Pimasertib (AS-703026, MSC1936369B), Refametinib (BAY 86-9766), TAK-733, cobimetinib (GDC-0973), GDC-0623, WX-554, selumetinib (AZD6244); CI-1040; PD184352; PD318088, PD98059, PD334581, PD0325901, RDEA119, 6-Methoxy-7-(3-morpholin-4-yl-propoxy)-4-(4-phenoxy-phenylamino)-quinoline-3-carbonitrile; 4-[3-Chloro-4-(1-methyl-1H-imidazol-2-ylsulfanyl)-phenylamino]-6-methoxy-7-(3-morpholin-4-yl-propoxy)-quinoline-3-carbonitrile, RO-4987655 (CH4987655), U0126 and E6201, or combinations thereof. Additional MEK inhibitors known in the art may also be used.

By way of non-limiting example, the ERK inhibitor provided herein can be VX-11e, SCH-772984, GDC-0994, BVD-523 and FR180204. Additional ERK inhibitors known in the art may also be used. Exemplary ERK inhibitors are shown in Table 3.

Administration of the combination includes administration of the combination in a single formulation or unit dosage form, administration of the individual agents of the combination concurrently but separately, or administration of the individual agents of the combination sequentially by any suitable route. The dosage of the individual agents of the combination may require more frequent administration of one of the agents as compared to the other agent in the combination. Therefore, to permit appropriate dosing, packaged pharmaceutical products may contain one or more dosage forms that contain the combination of agents, and one or more dosage forms that contain one of the combinations of agents, but not the other agent(s) of the combination.

Agents may contain one or more asymmetric elements such as stereogenic centers or stereogenic axes, e.g., asymmetric carbon atoms, so that the compounds can exist in different stereoisomeric forms. These compounds can be, for example, racemates or optically active forms. For compounds with two or more asymmetric elements, these compounds can additionally be mixtures of diastereomers. For compounds having asymmetric centers, it should be understood that all of the optical isomers and mixtures thereof are encompassed. In addition, compounds with carbon-carbon double bonds may occur in Z- and E-forms; all isomeric forms of the compounds are included in the present invention. In these situations, the single enantiomers (optically active forms) can be obtained by asymmetric synthesis, synthesis from optically pure precursors, or by resolution of the racemates. Resolution of the racemates can also be accomplished, for example, by conventional methods such as crystallization in the presence of a resolving agent, or chromatography, using, for example a chiral HPLC column.

Unless otherwise specified, or clearly indicated by the text, reference to compounds useful in the combination therapy of the invention includes both the free base of the compounds, and all pharmaceutically acceptable salts of the compounds. A preferred salt is the hydrochloride salt.

The term "pharmaceutically acceptable salts" includes derivatives of the disclosed compounds, wherein the parent compound is modified by making non-toxic acid or base addition salts thereof, and further refers to pharmaceutically acceptable solvates, including hydrates, of such compounds and such salts. Examples of pharmaceutically acceptable salts include, but are not limited to, mineral or organic acid addition salts of basic residues such as amines; alkali or organic addition salts of acidic residues such as carboxylic acids; and the like, and combinations comprising one or more of the foregoing salts. The pharmaceutically acceptable salts include non-toxic salts and the quaternary ammonium salts of the parent compound formed, for example, from non-toxic inorganic or organic acids. For example, non-toxic acid salts include those derived from inorganic acids such as hydrochloric, hydrobromic, sulfuric, sulfamic, phosphoric, and nitric; other acceptable inorganic salts include metal salts such as sodium salt, potassium salt, and cesium salt; and alkaline earth metal salts, such as calcium salt and magnesium salt; and combinations comprising one or more of the foregoing salts.

Pharmaceutically acceptable organic salts include salts prepared from organic acids such as acetic, trifluoroacetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, $HOOC(CH_2)_nCOOH$ where n is 0-4; organic amine salts such as triethylamine salt, pyridine salt, picoline salt, ethanolamine salt, triethanolamine salt, dicyclohexylamine salt, N,N'-dibenzylethylenediamine salt; and amino acid salts such as arginate, asparginate, and glutamate, and combinations comprising one or more of the foregoing salts.

An "effective amount" of a combination of agents is an amount sufficient to provide an observable improvement over the baseline clinically observable signs and symptoms of the disorder treated with the combination.

The pharmaceutical products can be administered by oral or other forms, e.g., rectally or by parenteral injection. "Oral dosage form" is meant to include a unit dosage form prescribed or intended for oral administration. An oral dosage form may or may not comprise a plurality of subunits such as, for example, microcapsules or microtablets, packaged for administration in a single dose.

The pharmaceutical products can be released in various forms. "Releasable form" is meant to include instant release, immediate-release, controlled-release, and sustained-release forms.

"Instant-release" is meant to include a dosage form designed to ensure rapid dissolution of the active agent by modifying the normal crystal form of the active agent to obtain a more rapid dissolution.

"Immediate-release" is meant to include a conventional or non-modified release form in which greater than or equal to about 50% or more preferably about 75% of the active agents is released within two hours of administration, preferably within one hour of administration.

"Sustained-release" or "extended-release" includes the release of active agents at such a rate that blood (e.g., plasma) levels are maintained within a therapeutic range but below toxic levels for at least about 8 hours, preferably at least about 12 hours, more preferably about 24 hours after administration at steady-state. The term "steady-state" means that a plasma level for a given active agent or combination of active agents, has been achieved and which is maintained with subsequent doses of the active agent(s) at a level which is at or above the minimum effective therapeutic level and is below the minimum toxic plasma level for a given active agent(s).

The term "treat", "treated," "treating" or "treatment" is used herein to mean to relieve, reduce or alleviate at least one symptom of a disease in a subject. For example, treatment can be diminishment of one or several symptoms of a disorder or complete eradication of a disorder, such as cancer. Within the meaning of the present invention, the term "treat" also denote to arrest, delay the onset (i.e., the period prior to clinical manifestation of a disease) and/or reduce the risk of developing or worsening a disease. The term "protect" is used herein to mean prevent delay or treat, or all, as appropriate, development or continuance or aggravation of a disease in a subject. Within the meaning of the present invention, the disease is associated with a cancer.

The term "subject" or "patient" is intended to include animals, which are capable of suffering from or afflicted with a cancer or any disorder involving, directly or indirectly, a cancer. Examples of subjects include mammals, e.g., humans, dogs, cows, horses, pigs, sheep, goats, cats, mice, rabbits, rats, and transgenic non-human animals. In certain embodiments, the subject is a human, e.g., a human suffering from, at risk of suffering from, or potentially capable of suffering from cancers.

The term "about" or "approximately" usually means within 20%, more preferably within 10%, and most preferably still within 5% of a given value or range. Alternatively, especially in biological systems, the term "about" means within about a log (i.e., an order of magnitude) preferably within a factor of two of a given value.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising, "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein.

As specified above, in one aspect, the instant invention provides a drug useful for treating, preventing, arresting, delaying the onset of and/or reducing the risk of developing, or reversing at least one symptom of cancer. In some embodiments a drug combination is provided by administering to the subject a combination therapy, including an effective amount of a first MAPK pathway inhibitor and a second MAPK pathway inhibitor. In some embodiments, the first MAPK inhibitor is an ERK inhibitor, a RAF inhibitor and/or a MEK inhibitor and the second MAPK pathway inhibitor is an ERK inhibitor, a RAF inhibitor and/or a MEK inhibitor that is different than the first MAPK inhibitor. Preferably, these inhibitors are administered at therapeutically effective dosages which, when combined, provide a beneficial effect. The administration may be simultaneous or sequential. In some embodiments, the treatment may be optimized by withdrawing the administration of the first MAPK pathway inhibitor, temporarily or permanently.

The term "cancer" is used herein to mean a broad spectrum of tumors, including all solid tumors and hematological malignancies. Examples of such tumors include but are not limited to leukemias, lymphomas, myelomas, carcinomas, metastatic carcinomas, sarcomas, adenomas, nervous system cancers and geritourinary cancers. In exemplary embodiments, the foregoing methods are useful in treating adult and pediatric acute lymphoblastic leukemia, acute myeloid leukemia, adrenocortical carcinoma, AIDS-related cancers, anal cancer, cancer of the appendix, astrocytoma, basal cell carcinoma, bile duct cancer, bladder cancer, bone cancer, osteosarcoma, fibrous histiocytoma, brain cancer, brain stem glioma, cerebellar astrocytoma, malignant glioma, ependymoma, medulloblastoma, supratentorial primitive neuroectodermal tumors, hypothalamic glioma, breast cancer, male breast cancer, bronchial adenomas, Burkitt lymphoma, carcinoid tumor, carcinoma of unknown origin, central nervous system lymphoma, cerebellar astrocytoma, malignant glioma, cervical cancer, childhood cancers, chronic lymphocytic leukemia, chronic myelogenous leukemia, chronic myeloproliferative disorders, colorectal cancer, cutaneous T-cell lymphoma, endometrial cancer, ependymoma, esophageal cancer, Ewing family tumors, extracranial germ cell tumor, extragonadal germ cell tumor, extrahepatic bile duct cancer, intraocular melanoma, retinoblastoma, gallbladder cancer, gastric cancer, gastrointestinal stromal tumor, extracranial germ cell tumor, extragonadal germ cell tumor, ovarian germ cell tumor, gestational trophoblastic tumor, glioma, hairy cell leukemia, head and neck cancer, hepatocellular cancer, Hodgkin lymphoma, non-Hodgkin lymphoma, hypopharyngeal cancer, hypothalamic and visual pathway glioma, intraocular melanoma, islet cell tumors, Kaposi sarcoma, kidney cancer, renal cell cancer, laryngeal cancer, lip and oral cavity cancer, small cell lung cancer, non-small cell lung cancer, primary central nervous system lymphoma, Waldenstrom macroglobulinema, malignant fibrous histiocytoma, medulloblastoma, melanoma, Merkel cell carcinoma, malignant mesothelioma, squamous neck cancer, multiple endocrine neoplasia syndrome, multiple myeloma, mycosis fungoides, myelodysplastic syndromes, myeloproliferative disorders, chronic myeloproliferative disorders, nasal cavity and paranasal sinus cancer, nasopharyngeal cancer, neuroblastoma, oropharyngeal cancer, ovarian cancer, pancreatic cancer, parathyroid cancer, penile cancer, pharyngeal cancer, pheochromocytoma, pineoblastoma and supratentorial primitive neuroectodermal tumors, pituitary cancer, plasma cell neoplasms, pleuropulmonary blastoma, prostate cancer, rectal cancer, rhabdomyosarcoma, salivary gland cancer, soft tissue sarcoma, uterine sarcoma, Sezary syndrome, non-melanoma skin cancer, small intestine cancer, squamous cell carcinoma, squamous neck cancer, supratentorial primitive neuroectodermal tumors, testicular cancer, throat cancer, thymoma and thymic carcinoma, thyroid cancer, transitional cell cancer, trophoblastic tumors, urethral cancer, uterine cancer, uterine sarcoma, vaginal cancer, vulvar cancer, and Wilms tumor.

In particular, the cancer may be associated with a mutation in the B-RAF gene. In some embodiments, the cancer may be a RAF or a MEK dependent cancer. These cancers include but are not limited to melanoma, breast cancer, colorectal cancers, glioma, lung cancer, ovarian cancer, sarcoma and thyroid cancer.

In a particular embodiment, the therapeutic combination provided herein is effective for the treatment of moderate to severe cancer in a subject.

Dosages

The optimal dose of the combination of agents for treatment of cancer can be determined empirically for each subject using known methods and will depend upon a variety of factors, including the activity of the agents; the age, body weight, general health, gender and diet of the subject; the time and route of administration; and other medications the subject is taking. Optimal dosages may be established using routine testing and procedures that are well known in the art.

The amount of combination of agents that may be combined with the carrier materials to produce a single dosage form will vary depending upon the individual treated and the particular mode of administration. In some embodiments the unit dosage forms containing the combination of agents as described herein will contain the amounts of each agent of the combination that are typically administered when the agents are administered alone.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound that is the lowest dose effective to produce a therapeutic effect. Such an effective dose will generally depend upon the factors described above and is readily determined by one having skill in the art.

Generally, therapeutically effective doses of the compounds of this invention for a patient, when used for the indicated analgesic effects, will range from about 0.0001 to about 1000 mg per kilogram of body weight per day, more preferably from about 0.01 to about 50 mg per kg per day.

If desired, the effective daily dose of the active compound may be administered as two, three, four, five, six or more sub-doses administered separately at appropriate intervals, optionally, in unit dosage forms.

Pharmaceutical Formulations and Routes of Administration

Provided herein are pharmaceutical formulations comprising a combination of agents for the treatment of cancer, e.g., melanoma. The pharmaceutical formulations may additionally comprise a carrier or excipient, stabilizer, flavoring agent, and/or coloring agent.

Provided herein are pharmaceutical formulations comprising combination of agents which can be, for example, a combination of two types of agents: (1) an ERK inhibitor and/or pharmacologically active metabolites, salts, solvates and racemates of the inhibitor and (2) a RAF inhibitor or a MEK inhibitor or both a RAF inhibitor and a MEK inhibitor and/or pharmacologically active metabolites, salts, solvates and racemates of the RAF and/or MEK inhibitor.

The combination of agents may be administered using a variety of routes of administration known to those skilled in the art. The combination of agents may be administered to humans and other animals orally, parenterally, sublingually, by aerosolization or inhalation spray, rectally, intracisternally, intravaginally, intraperitoneally, bucally, or topically in dosage unit formulations containing conventional nontoxic pharmaceutically acceptable carriers, adjuvants, and vehicles as desired. Topical administration may also involve the use of transdermal administration such as transdermal patches or ionophoresis devices. The term parenteral as used herein includes subcutaneous injections, intravenous, intramuscular, intrasternal injection, or infusion techniques.

Methods of formulation are well known in the art and are disclosed, for example, in Remington: The Science and Practice of Pharmacy, Mack Publishing Company, Easton, Pa., 19th Edition (1995). Pharmaceutical compositions for use in the present invention can be in the form of sterile, non-pyrogenic liquid solutions or suspensions, coated capsules, suppositories, lyophilized powders, transdermal patches or other forms known in the art.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3 propanediol or 1,3 butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil may be employed including synthetic mono or di glycerides. In addition, fatty acids such as oleic acid find use in the preparation of injectables. The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form may be accomplished by dissolving or suspending the drug in an oil vehicle. Injectable depot forms are made by forming microencapsule matrices of the drug in biodegradable polymers such as polylactide polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations may also be prepared by entrapping the drug in liposomes or microemulsions, which are compatible with body tissues.

Compositions for rectal or vaginal administration are preferably suppositories which can be prepared by mixing the compounds of this invention with suitable non irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, acetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, EtOAc, benzyl alcohol, benzyl benzoate, propylene glycol, 1,3 butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulations, ear drops, and the like are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Compositions of the invention may also be formulated for delivery as a liquid aerosol or inhalable dry powder. Liquid aerosol formulations may be nebulized predominantly into particle sizes that can be delivered to the terminal and respiratory bronchioles.

Aerosolized formulations of the invention may be delivered using an aerosol forming device, such as a jet, vibrating porous plate or ultrasonic nebulizer, preferably selected to allow the formation of an aerosol particles having with a mass medium average diameter predominantly between 1 to 5 μm. Further, the formulation preferably has balanced osmolarity ionic strength and chloride concentration, and the smallest aerosolizable volume able to deliver effective dose of the compounds of the invention to the site of the infection. Additionally, the aerosolized formulation preferably does not impair negatively the functionality of the airways and does not cause undesirable side effects.

Aerosolization devices suitable for administration of aerosol formulations of the invention include, for example, jet, vibrating porous plate, ultrasonic nebulizers and energized dry powder inhalers, that are able to nebulize the formulation of the invention into aerosol particle size predominantly in the size range from 1 to 5 μm. Predominantly in this application means that at least 70% but preferably more than 90% of all generated aerosol particles are within 1 to 5 μm range. A jet nebulizer works by air pressure to break a liquid solution into aerosol droplets. Vibrating porous plate nebulizers work by using a sonic vacuum produced by a rapidly vibrating porous plate to extrude a solvent droplet through a porous plate. An ultrasonic nebulizer works by a piezoelectric crystal that shears a liquid into small aerosol droplets. A variety of suitable devices are available, including, for example, AERONEB and AERODOSE vibrating porous plate nebulizers (AeroGen, Inc., Sunnyvale, Calif.), SIDESTREAM nebulizers (Medic Aid Ltd., West Sussex, England), PARI LC and PARI LC STAR jet nebulizers (Pan Respiratory Equipment, Inc., Richmond, Va.), and AEROSONIC (DeVilbiss Medizinische Produkte (Deutschland) GmbH, Heiden, Germany) and ULTRAAIRE (Omron Healthcare, Inc., Vernon Hills, Ill.) ultrasonic nebulizers.

Compounds of the invention may also be formulated for use as topical powders and sprays that can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel. The compounds of the present invention can also be administered in the form of liposomes. As is known in the art, liposomes are generally derived from phospholipids or other lipid substances. Liposomes are formed by mono or multi lamellar hydrated liquid crystals that are dispersed in an aqueous medium. Any nontoxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and phosphatidyl cholines (lecithins), both natural and synthetic. Methods to form liposomes are known in the art. See, for example, Prescott (ed.), "Methods in Cell Biology," Volume XIV, Academic Press, New York, 1976, p. 33 et seq.

Examples

ERK1/ERK2 Random Mutagenesis

To discover mutations in ERK1 or ERK2 that may confer resistance to MAPK inhibitors, a six-part random mutagenesis screen was performed. Here, we mutagenized ERK1 and ERK2 within the pDONR223 vector using a mutator strain of E. coli (22). The resulting mutagenized cDNA library was transferred into a doxycyline (DOX) inducible vector (pCW57.1), which was infected into A375 (BRAF-mutant) melanoma cells that are sensitive to MAP kinase pathway inhibitors. These cells were cultured in the presence of either the ERK inhibitor VX-11e (23), the MEK inhibitor trametinib (GSK1120212), or the combination of trametinib and the RAF inhibitor, dabrafenib (GSK2118436), in the presence of DOX. In all cases, drug-resistant A375 daughter populations emerged within 2-4 weeks. Genomic DNA was isolated and ERK1 or ERK2 cDNA was amplified by the polymerase chain reaction followed by massively parallel sequencing (see Methods). In parallel experiments, a series of VX-11e-resistant ERK2 colonies were isolated and ERK2 cDNA was analyzed by Sanger sequencing.

Overall, we identified 33 putative resistance variants spanning 28 amino acids in ERK1, and 24 substitutions affecting 20 amino acids in ERK2 (above a 5% massively parallel sequencing false discovery rate; see Methods) (FIG. 1, FIG. 8A-F, and Table 4). Sanger sequencing of 23 VX-11e-resistant colonies identified 7 ERK2 mutations in 5 amino acids, two of which were also identified in the mutagenesis screens. We have no evidence that these mutagenesis screens were saturating; therefore, additional candidate ERK1/2 resistance mutations may remain to be identified. Nonetheless, our screening results suggested that a diverse range of ERK mutations might be associated with resistance to these inhibitors.

We observed 5 analogous resistance alleles between ERK1 and ERK2 in cells resistant to the ERK inhibitor in both the screen and in isolated colonies (ERK1Y53H/ERK2Y36H/N, ERK1G54A/ERK2G37S, ERK1P75L/ERK2P58L, ERK1Y81C/ERK2Y64N, and ERK1C82Y/ERK2C65Y; FIG. 1C), and one analogous residue in MEK inhibitor resistant cells (ERK1Y148H and ERK2Y131N/H/F/C/S; FIG. 1D), suggesting convergent resistance mechanisms between the ERK isoforms. There was relatively little overlap between the ERK inhibitor screens and the RAF/MEK inhibitor screens (3 overlapping alleles out of 67 total significant nucleotide alterations) raising the possibility that mutations identified through RAF/MEK inhibitor treatment might be resistant to one or both of these agents, but not to ERK inhibitors (and vice versa). Several ERK codons had multiple distinct amino acid substitutions (these include ERK1Y53C/H, ERK1G54A/S, ERK2Y36N/H, ERK2P58L/S/T, and ERK2 Y131C/F/H/N/S), suggesting the importance of these residues for inhibition by ATP-competitive ERK inhibitors.

In general, candidate ERK resistance mutations arising in the ERK inhibitor resistance screen clustered within the ATP/drug binding pocket, suggesting that these variants might interfere with drug binding. In contrast, the RAF/MEK inhibitor resistance alleles were distributed throughout the ERK proteins, although some mutations clustered in the αC-helix and the common docking domain. The ERK αC-helix undergoes a conformational change when phosphorylated that is necessary for kinase activation, while the common docking domain represents one of the ERK substrate binding domains. These observations suggested that ERK resistance alleles that emerged under RAF/MEK inhibition might facilitate kinase activation. In addition, several of these alterations have been previously identified through DNA sequencing efforts. Alterations at ERK1R84, ERK1G186, ERK2D321, and ERK2E322 are listed in the COSMIC database (Available on the World Wide Web at cancer.sanger.ac.uk/cancergenome/projects/cosmic/); however, none of these variants have been linked to drug resistance.

Figure 8:
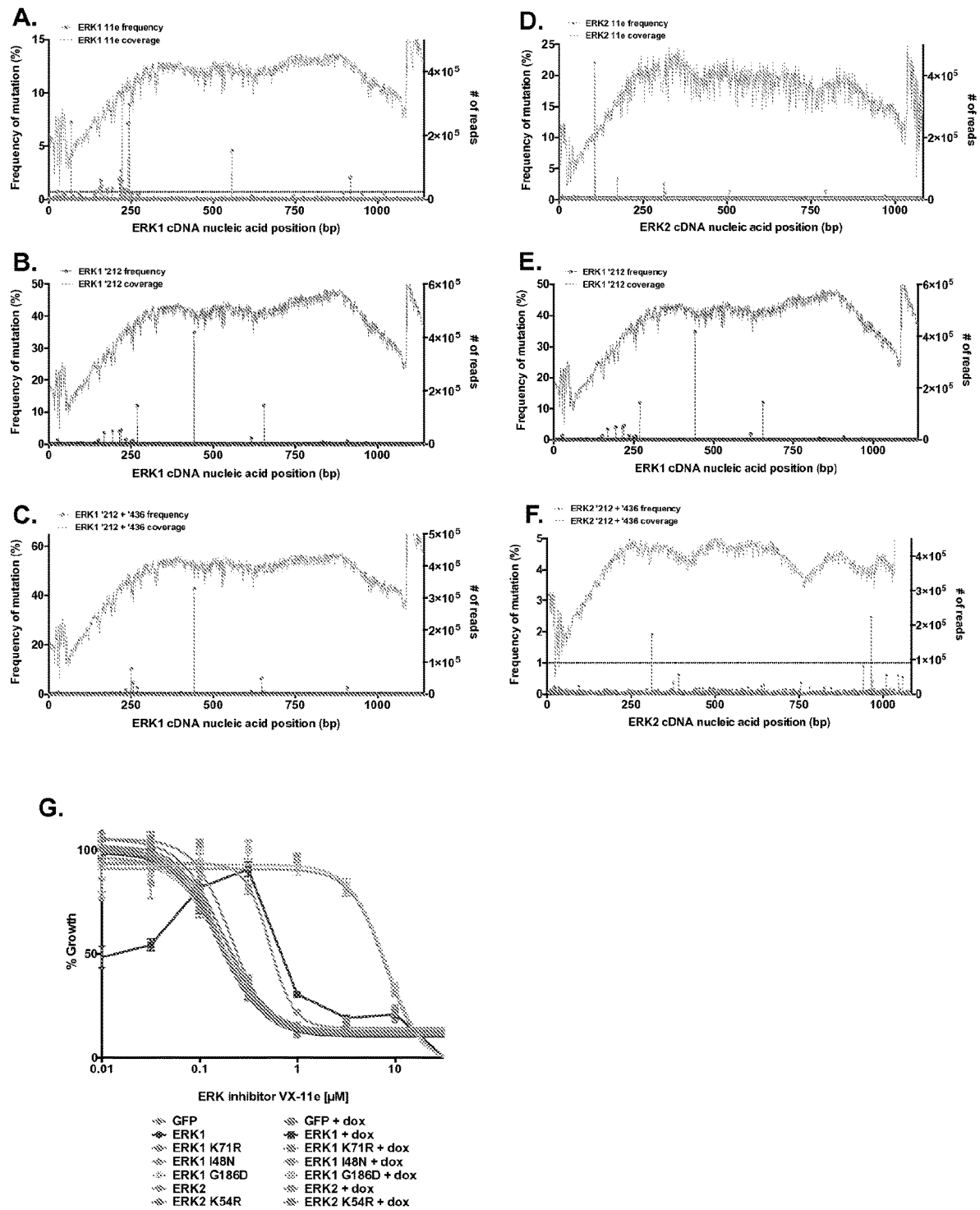

ERK1 and ERK2 mutations confer resistance to ERK inhibitors by interfering with drug binding We first focused on characterizing selected ERK1/2 mutations that arose in the setting of ERK inhibition. To verify their resistance effects, we engineered the relevant mutations for highly mutated alleles or for low frequency alleles that were analogous between ERK1 and ERK2 within the coding sequence of ERK1 or ERK2 by site directed mutagenesis in the doxycycline-inducible vector. The resulting constructs were stably introduced into A375 cells and evaluated for growth in the presence of VX-11e. In total, we tested 20 candidate ERK1/2 resistance alleles in cell growth inhibition assays, of which 16 were deemed "validated" in vitro. Here, we defined validation as a >4-fold increase in cell growth conferred by DOX-induced mutant ERK expression compared to control cells cultured without DOX (FIG. 2A, Table 4, FIG. 8G). In these experiments, wild-type ERK1 and ERK2 conferred a minor growth advantage (1.5-fold) in the presence of the ERK inhibitor, whereas kinase-dead ERK1 and ERK2 (24) and GFP had no effect (FIG. 2A).

To determine whether these ERK1 and ERK2 resistance alleles might confer cross-resistance to other ERK inhibitors, we also performed cell growth inhibition assays using the ERK inhibitor SCH772984. For ERK1, we chose three alleles that conferred the highest growth and the allele that conferred the least highest growth in the presence of the VX-11e, and all three ERK2 alleles identified in the screen for analysis. These alleles, deemed resistant to VX-11e, were also resistant to SCH772984, as measured by over 4-fold increases in cell growth with allele expression. One allele, ERK1$^{Y53H}$, showed only a 2.5-fold increase in cell growth at 1 µM SCH772984, but conferred a 5-fold growth advantage at 0.5 µM SCH772984, similar to the other ERK1 alleles (FIG. 2B). Conceivably, this difference may relate to compound-specific differences in ERK binding associated with this particular residue.

Figure 9:
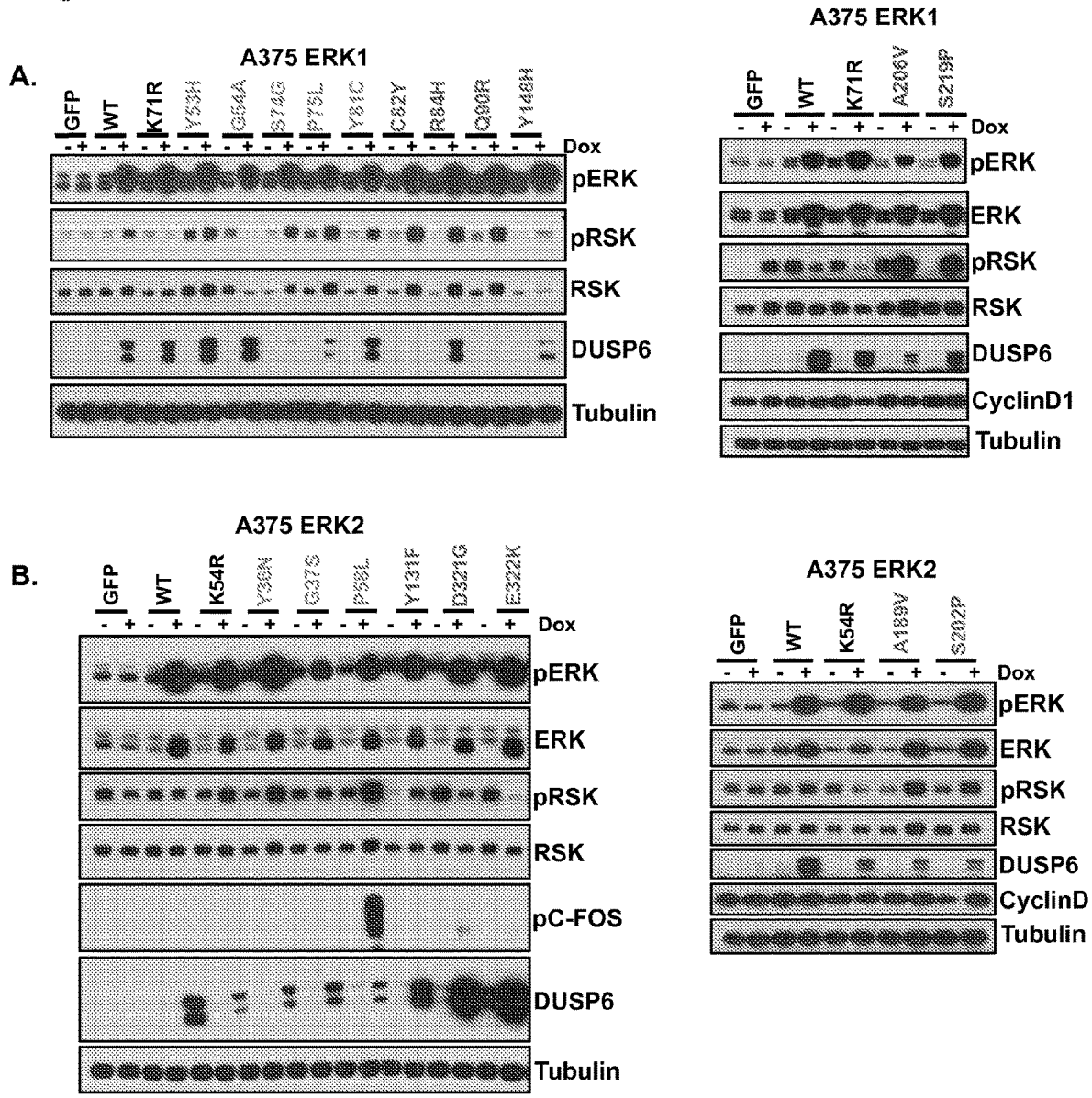

Next, we measured the effects of ERK resistance alleles on ERK substrate phosphorylation. First, we examined ERK signaling from a representative set of ten validated alleles upon DOX induction. As a control, we included wild type ERK1 and ERK2, both of which produced robust RSK phosphorylation and elevated DUSP6 expression in this setting (FIG. 9). In contrast, kinase-dead ERK1 and ERK2 showed no increased RSK phosphorylation, but did induce DUSP6 expression, suggesting a possible kinase-independent function (FIG. 9). In the absence of ERK inhibitor, all validated ERK resistance alleles examined augmented either RSK phosphorylation, DUSP6 expression, or both.

Some alleles had discordant effects on ERK signaling. For example, both ERK1$^{G54A}$ and its analogous variant ERK2$^{G37S}$ had minimal effects on RSK phosphorylation following DOX induction, but produced elevated DUSP6 expression (similar to the kinase-dead ERK variants). In contrast, ERK1$^{S74G}$, ERK1$^{P75L}$ and the orthologous allele ERK2$^{P58L}$ had modest effects on DUSP6 expression but robust up-regulation of RSK phosphorylation. Thus, although ERK resistance alleles may partially alter downstream signaling, they may still confer a growth advantage in the setting of ERK inhibition.

Next, we analyzed ERK signaling with the ERK variants upon addition of VX-11e. All ten ERK inhibitor resistance alleles enabled sustained ERK signaling based on RSK phosphorylation or accumulation of DUSP6 (or both; FIG. 2C). Expression of another downstream effector of ERK signaling, cyclin D1, was also maintained in the presence of drug compared to controls. ERK signaling was also maintained in the presence of the SCH772984 compound (FIG. S3A). SCH772984 decreased phosphorylation of wild type ERK1/2, however, this compound had no effect on phosphorylation of ERK2-resistant alleles (FIG. 10A). In contrast, VX-11e had no effect on ERK phosphorylation in any context examined (FIG. 3). Thus, the identified resistant alleles can maintain ERK signaling in the presence of an ERK inhibitor.

To determine whether the intrinsic kinase activity the ERK1/2 alleles was maintained with VX-11e, we examined the kinase activity of the ERK resistance alleles (together with wild-type and kinase-dead controls) using an immunoprecipitation (IP)-based kinase assay (see Methods). Here, V5-tagged ERK1 or ERK2 were immnoprecipitated following transfection into A375 cells and incubated together with a recombinant ELK-1 peptide (an ERK substrate) in the absence or presence of VX-11e. Phosphorylation of ELK-1 (at serine 383) was measured by Western blotting. As expected, VX-11e completely blocked the ELK-1 phosphorylation induced by wild type ERK1 and ERK2. However, all ERK resistance alleles examined maintained ERK kinase activity, even in the presence of VX-11e (FIG. 3A-B) or SCH772984 (FIG. 10B). As expected, kinase-dead ERK1/2 did not phosphorylate the ELK-1 peptide (FIG. 3A-B). Thus, the validated resistance alleles maintained kinase activity even with ERK inhibitor exposure.

Finally, we mapped the validated ERK1 and ERK2 alleles within the three-dimensional crystal structure of ERK2 bound to a structurally similar ERK inhibitor (VX-9a; (23), PDB:3I60). The resistance alleles occur in close proximity to the ATP/drug binding pocket, albeit within distinct functional domains (FIG. 2D). In particular, they reside within the glycine rich loop (ERK1$^{I48N}$, ERK1$^{Y53H}$, ERK1$^{G54A}$, ERK2$^{Y36N/H}$, and ERK2$^{G37S}$), between the β3-strand and αC-helix (ERK1$^{S74G}$, ERK1$^{P75L}$, and ERK2$^{P58L}$), within the αC-helix (ERK1$^{Y81C}$, ERK1$^{C82Y}$, ERK2$^{Y64N}$, and ERK2$^{C65Y}$), and in the activating loop)(ERK1G$^{186D}$). Together, these efforts have identified several distinct ERK mutations that presumably interfere with engagement of the ATP binding cleft by ERK inhibitors.

ERK Mutations that Confer Resistance to RAF/MEK Inhibition Preserve ERK Activity Despite MEK Inhibition Next, we validated either high frequency (>4%) candidate ERK1/2 resistance alleles or low frequency alleles observed in both MEK inhibitor alone or RAF+MEK inhibitor screens. After cloning and expressing these mutations as described above, we performed cell growth inhibition assays using the MEK inhibitor trametinib and RAF inhibitor dabrafenib, either alone or in combination. Of 17 mutated alleles examined, 10 were confirmed as resistant to each agent and the combination, conferring over a 2.5 fold growth advantage in the presence of the inhibitor compared to controls (FIG. 4A, Table 5). The fact that ERK1$^{A206V}$ and ERK1$^{S219P}$ conferred robust resistance to RAF and MEK inhibitors prompted us to engineer the analogous mutations within ERK2 (since these were not observed in the primary screen). Indeed, the resulting alleles (ERK2$^{A189V}$ and ERK2$^{S202P}$) also conferred robust resistance to RAF/MEK inhibition (FIG. 4A). Of the 7 alleles that failed validation, at least two may have been passenger mutations that co-occurred with bona fide resistance alleles during the mutagenesis procedure (FIG. 13).

The observation that validated ERK1/2 alleles conferred cross resistance to all RAF/MEK inhibitor conditions raised the possibility that in contrast to the ERK inhibitor resistance mutations, these might represent activating ERK1/2 events. This notion was buttressed by the observation that the ERK2$^{E322K}$ mutation—a known activating allele that occurs in cervical cancers—arose in this context. Moreover, ERK1/2$^{A206V/A189V}$ and ERK1/2$^{S219P/S202P}$ occur in the activation lip of ERK1/2 and in close proximity to the two phosphorylation residues that confer full ERK kinase activity when phosphorylated (ERK1$^{T202/Y204}$ and ERK2$^{T185/Y187}$; FIG. 4B, FIG. 11A). Other validated RAF/MEK inhibitor resistance alleles map to the αC-helix (ERK1$^{C82Y}$, ERK1$^{R84H}$, and ERK1$^{Q90R}$), and common docking domain (ERK1$^{Y148H}$, ERK2$^{Y131F}$, ERK2$^{D321G}$, and ERK2$^{E322K}$). Mutations in the common docking domains at ERK2$^{D321N}$ and ERK2$^{E322K}$ confer elevated activity in vivo due to reduced DUSP binding (19). Alterations at ERK1/2$^{Y148/Y131}$ have not been described, but may in principle impair phosphatase and substrate binding considering their three-dimensional localization near the common docking domain (FIG. 11B).

Figure 12:
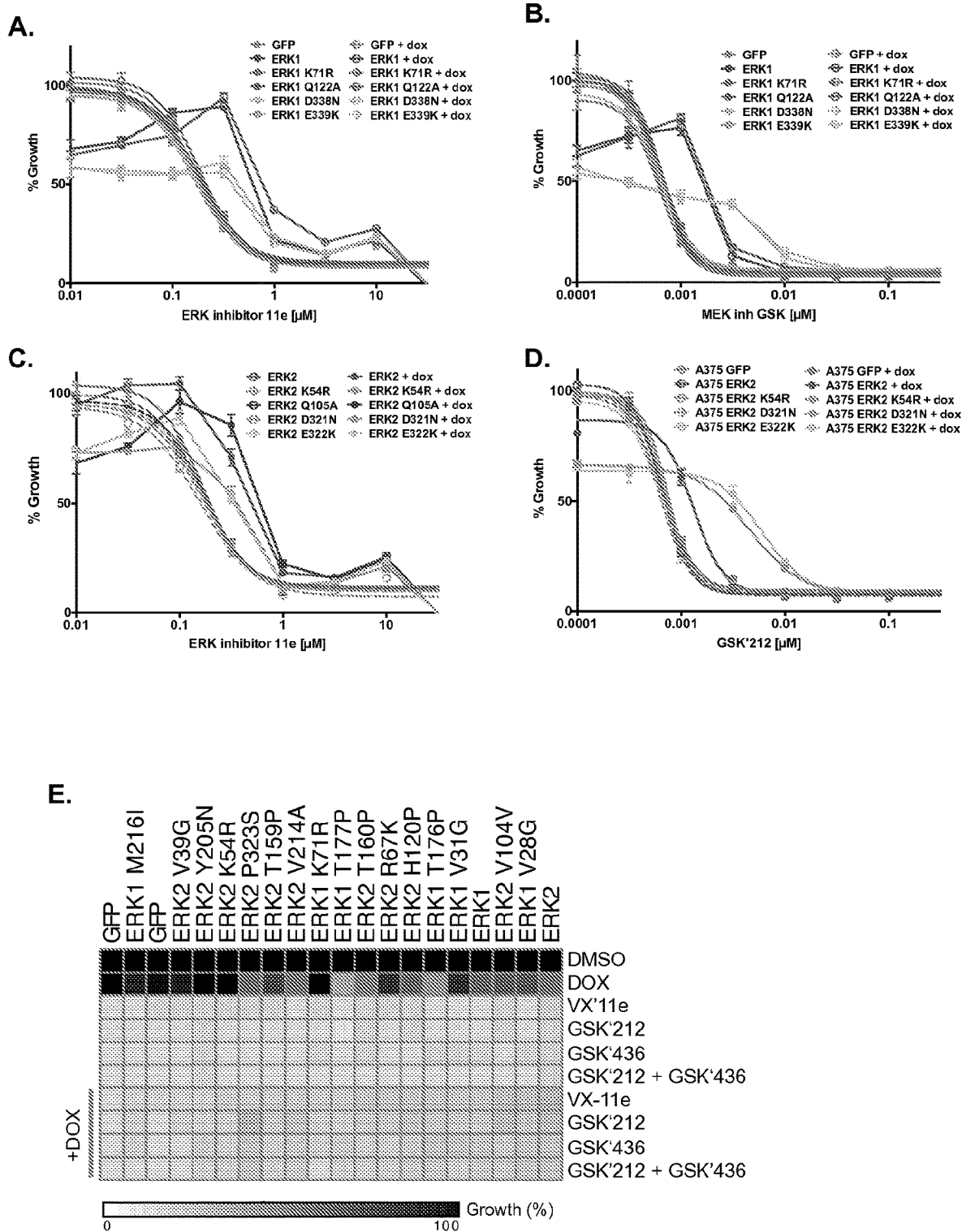

Although our mutagenesis screens were unlikely to be saturating, we only observed αC-helix resistance mutations in ERK1, whereas common docking domain alterations (ERK2$^{D321G}$ and ERK2$^{E322K}$) were only found in ERK2 (FIG. 4B). Interestingly, the analogous common docking domain mutations in ERK1 (ERK1$^{D338N}$ and ERK1$^{E339K}$) did not confer resistance to RAF/MEK inhibition in our hands (FIG. 12). This suggests that while ERK1 and ERK2 are highly homologous, "activating" variants of ERK1 and ERK2 may contain distinctive functional attributes, thus allowing dissection of isoform-specific functions in the future.

Next, we analyzed ERK signaling after expression of the validated alleles. As with the ERK inhibitor resistance mutations, DOX-induced expression of RAF/MEK inhibitor resistance alleles in both ERK1 and ERK2 activated ERK signaling, as evidenced by RSK or DUSP6 expression (FIG. 9). Common docking domain mutations, (e.g., ERK2$^{D321G}$ and ERK2$^{E322K}$), did not induce RSK phosphorylation, consistent with published observations that such alterations may disrupt RSK binding (25). When these same ERK1/2 mutations were expressed in the presence of the MEK inhibitor, both DUSP6 and Cyclin D1 expression were robustly maintained in the RAF/MEK inhibitor resistant alleles in the presence of inhibitor; RSK phosphorylation was more variable (FIG. 4C,D). These results suggested that ERK1/2 mutations arising in the setting of RAF/MEK inhibition could maintain ERK signaling, even in the presence of upstream pathway inhibition.

To determine whether the intrinsic kinase activity of the RAF/MEK inhibitor resistant ERK alleles was maintained after MEK inhibitor exposure, we analyzed ERK kinase activity by IP kinase assays. Here again, all ERK resistance alleles examined maintained ERK kinase activity (as measured by ELK-1 peptide phosphorylation) in the presence of MEK inhibitor, even though MEK-dependent (and activating) ERK phosphorylation was decreased (FIG. 5, input). ELK-1 binds to both the F-site recruitment site and the common docking domain within ERK. Therefore, mutations confined to the common docking domain (ERK1$^{Y148}$/ERK2$^{Y131}$, ERK2$^{D321G}$, ERK2$^{E322K}$) might not be sufficient to abolish ERK-ELK-1 interactions (25, 26). However, we observed diminished residual kinase activity in the setting of trametinib exposure with the common docking domain mutants compared to other alleles (FIG. 5). Altogether, these results suggest that ERK resistance alleles arising in the setting of RAF/MEK inhibition maintain sufficient kinase activity to rescue BRAF-mutant melanoma cell growth—even in the presence of upstream pathway inhibition.

RAF/MEK Inhibitor-Derived ERK Resistance Alleles are Sensitive to ERK Inhibition, and Vice Versa Several clinically validated genetic mechanisms of resistance to RAF and MEK inhibitors remain sensitive to ERK inhibition in preclinical studies (FIG. 14A) (7, 8, 27). In our hands, RAF or MEK inhibitor-resistant BRAF-mutant melanoma cell populations generated by continuous exposure to tool compound inhibitors (PLX-4720 and AZD6244, respectively) following ENU mutagenesis were also sensitive to ERK inhibition (FIG. 14B). Since ERK resistance mutants arising in the presence of an ERK inhibitor were largely distinct from those that emerged following RAF/MEK inhibition, we wished to determine whether either category of ERK mutations might confer cross-resistance to the alternative MAP kinase pathway inhibitor(s).

To investigate this possibility, we performed cell growth inhibition assays in all of our validated ERK resistance alleles in the presence of RAF, MEK, and ERK inhibitors. In general, we observed that ERK resistance mutations that arose under RAF/MEK inhibitor selection were sensitive to ERK inhibition, and conversely that ERK mutations arising under ERK inhibitor selection remained sensitive to RAF and/or MEK inhibition (FIG. 6A). The same was true in two additional cell lines SKMEL19 (FIG. 6B-C) and WM266.4 (FIG. 15A), however, the overall magnitude of resistance was lower. Interestingly, one ERK mutation, ERK1$^{C82Y}$, conferred resistance to all of these compounds—though the magnitude of the resistance phenotype was relatively modest (proliferation of 45% (RAF/MEK inhibitors) and 75% (ERK inhibitor) compared to untreated controls. Overall, ERK resistance mutations arising from ERK inhibition remained vulnerable to combined RAF/MEK inhibition, and the converse was also true.

ERK1/2 Overexpression Reduces the Viability of Some BRAF-Mutant Melanoma Cells

While performing these studies, we noticed that overexpression of ERK1/2 was lethal to A375 cells in the absence of MAP kinase pathway inhibition. Although this effect could certainly result from nonspecific toxicities associated with ectopic protein expression, it was also possible that "too much" MAP kinase pathway activation might be deleterious to BRAF-mutant melanoma cells—particularly in light of the "drug holiday" effect that has occasionally been observed after RAF inhibition in melanoma models. To test this possibility, we assessed the cell proliferation of a panel of ERK1/ERK2 mutations that emerged from our mutagenesis screens.

Figure 15:
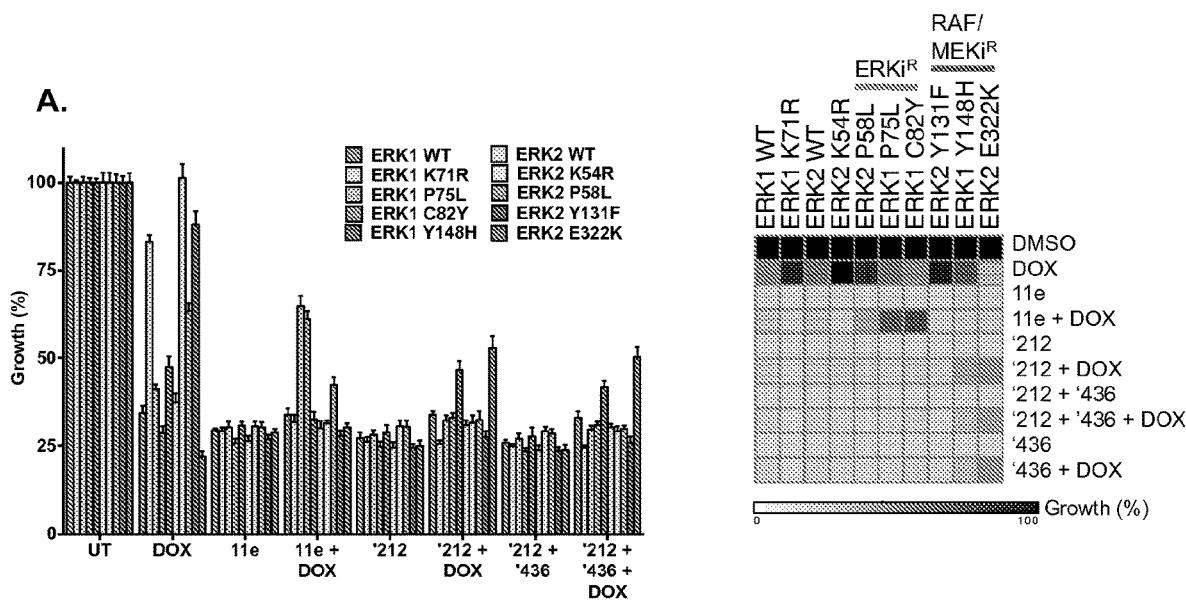

As noted above, overexpression of wild-type ERK1 and ERK2 decreased viability of A375 cells (FIG. 7A, FIG. 9). Moreover, the growth suppressive effect of ERK overexpression was generally linked to kinase activity, as kinase dead ERK1/2 (ERK1$^{K71R}$/ERK2$^{K54R}$) had no effect. Overexpression of ERK1$^{G54A}$ and ERK2$^{G37S}$, which exhibit reduced basal kinase activity compared to wild-type ERK (FIG. 3), also had no effect on cell growth (FIG. 7A). In contrast, ERK mutations arising in the setting of RAF/MEK inhibition produced the greatest reductions in cell growth (alleles highlighted in blue, FIG. 7B), consistent with the above observations that these mutations enhance intrinsic ERK kinase activity. We observed similar cell growth defects in a second BRAF-mutant melanoma cell line (WM266.4 cells; FIG. 15). However, in a third line (SK-MEL-19 cells), only the subset of ERK1 resistance alleles predicted to have augmented kinase activity reduced cell viability (e.g., ERK1$^{Q90R}$, ERK1$^{Y148H}$, and ERK1$^{S219P}$) (FIG. 6B, C). These data suggest that lethality of ERK1/2 alleles in A375 cells may be a surrogate for ERK kinase activity and/or ERK signaling.

Discussion

In melanoma, clinical resistance to RAF/MEK inhibition is often involves reactivation of the MAPK pathway. Although a variety of distinct mechanisms to achieve this effect have been described (e.g., activating mutations in NRAS or MEK pathway, alternative splicing or amplification of BRAF, COT, and receptor tyrosine kinases), ERK activation stands as their chief point of convergence. Thus ERK represents an attractive downstream target in MAPK dysregulated cancers, and several ERK inhibitors have entered clinical trials.

However, even if ERK inhibitors are successful, it seems likely that resistance to these agents could emerge, as has been seen with most other kinase-based anticancer therapeutics. Toward this end secondary mutations within the kinase target represent a common resistance mechanism for this class of therapeutics. The present study used random mutagenesis screens to identify mutations in ERK1 and ERK2 that confer resistance to tool compounds that bear structural similarity to ERK inhibitors in clinical trials. Multiple resistance mutations were identified in both ERK isoforms, and it seems likely that additional mutations could be identified in the future if such screens were carried out to saturation. Moreover, the mutations we identified using the VX-11e compound were cross-resistant to SCH772984 compound, suggesting that these resistance alleles could represent generalizable genetic resistance mechanisms to other ATP-competitive ERK inhibitors.

ERK kinases were discovered over 20 years ago (28), yet it has proved surprisingly difficult to generate constitutively active ERK1/2 alleles that exhibit enzymatic activity similar to that of wild type ERK following activating phosphorylation. Unlike MEK, where phosphomimetic mutations of two serine residues (e.g., glutamic acid substitutions at residues 218 and 222) is sufficient to produce robust activation of this kinase, analogous mutations in ERK (e.g. ERK1$^{T202/Y204}$ and ERK2$^{T185/Y187}$) do not lead to constitutive ERK activation (29). In addition, relatively little is known about possible functional differences between ERK isoforms. Toward this end, murine knockout studies have raised the possibility of distinct functions, but some of these effects might also have resulted from changes in total ERK1/2 levels (30, 31).

In this study, we identified several mutations in both ERK1 and ERK2 that retain robust ERK signaling despite pharmacologic RAF/MEK inhibition. While we have not formally proved that these represent bona fide constitutive active ERK isoforms, these mutations may nonetheless prove useful for future biochemical studies of the two ERK isoforms. Interestingly, 'activating' ERK1 mutations lie in the αC-helix, while 'activating' ERK2 mutants lie in the common docking domain. This distinction suggests that subtle yet meaningful biochemical differences between ERK1 and ERK2 may underpin MAP kinase signaling in both normal and malignant cells.

Furthermore, this work implies that BRAF-mutant melanoma cells must maintain tight control over ERK signaling to enable optimal growth. On the one hand, if flux through the MAPK pathway diminishes too much, growth arrest or apoptosis ensues. On the other hand, our results suggest that excessive MAPK signaling (over and above that conferred by BRAF$^{V600E}$) can also reduce cell viability, at least in some cases. This result is concordant with recent observations that 'acute' withdrawal of vemurafenib from a patient-derived xenograft tumor model that had progressed to drug resistance produced a temporary tumor regression (32). This has also been termed the "drug holiday" effect (33). Presumably, a flare of MAP kinase signaling ensued upon drug discontinuation proved deleterious to the tumor cells (of note, BRAF amplification was a resistance mechanism in this study).

If this general phenomenon (e.g., lethality of acute drug withdrawal) were broadly relevant at some point during the treatment course, one could envision an intermittent therapeutic strategy for RAF/MEK inhibition in melanoma. Indeed, intermittent vemurafenib allowed for disease stabilization in the aforementioned study by Das Thakur, Stuart and colleagues. There have also been reports of successful re-challenge with vemurafenib in patients that initially relapsed on the drug (34-36). Moreover, recent clinical trial results in which vemurafenib was administered chronically, while the MEK inhibitor was given intermittently suggest that intermittent MEK inhibition was no worse than chronic administration of both drugs, but MEK inhibitor toxicity may have been reduced by intermittent dosing (ASCO 2014 oral presentation). The ERK resistance alleles identified herein may provide a useful set of tools for detailed preclinical evaluation of intermittent ERK inhibition alternating with "acute" ERK hyperactivation as a novel therapeutic approach.

In summary, this study has identified a set of mutations in ERK1 and ERK2 that confer resistance to MAP kinase pathway inhibition at the level of RAF/MEK and ERK. These findings may anticipate future resistance mechanisms, enable new biochemical studies of ERK isoforms, and support preclinical studies of novel therapeutic strategies. They could also inform the development of "next-generation" ERK inhibitors that could be developed for melanoma and many other MAP kinase driven cancers.

Methods

Cell Lines and Reagents:

A375, 293T, SKMEL19, and WM266.4 were grown in DMEM with 10% FBS. A375 and 293T cells were acquired from ATCC. WM266.4 cells was acquired through the Cancer Cell Line Encyclopedia (Available on the World Wide Web at broadinstitute.org/ccle/home). SKMEL19 was a gift from N. Rosen (MSKCC). GSK1120212, GSK2118436, VX-11e and AZD6244 were from Chemietek. PLX4720 was from Selleck. SCH772984 was synthesized through the Broad Institute.

Random Mutagenesis:

Random mutagenesis was performed described previously (21) with the following modifications. Briefly, pDONR ERK1 and ERK2 (Addgene) constructs were transformed into mutagenic competent cells, XL-1 Red (Agilent) and grown to introduce approximately one mutation per kb. The pDONR constructs were transferred into the tet-inducible vector pCW57.1 (Addgene) using LR clonase II (Invitrogen).

Lentiviral Preparation:

The inducible constructs were transiently transfected with Δ8.91 and VSVG into 293T cells using X-tremeGENE 9 (Roche). Viral supernant was collected, filtered, and transferred to cells with polybrene (4 μg/mL).

Screen:

Tet-inducible GFP, WT ERK1/ERK2, and mutant library ERK1/ERK2 constructs were infected into A375 cells. 24 hours later, cells were selected in puromycin for two days. Cells were split one time, and then plated for the screens. DOX and drug were added at the same time. Cells were grown in VX-11e (2 μM), trametinib (3 nM), or trametinib+ dabrafenib (1 nM+10 nMf) for 2-4 weeks until resistant cells emerged. At that time, genomic DNA (gDNA) was collected using DNA Easy blood and tissue kit (Qiagen). Exogenous ERK1/2 was amplified by PCR with vector specific primers (Supplemental methods) and AccuPrime PFX supermix (Life Technologies). When single colonies were isolated, each colony was transferred to a 96 well plate and then further amplified. Then, genomic DNA was isolated and PCR was performed as above. Samples were then sent for Sanger sequencing.

Library Generation and Massively Parallel Sequencing:

Sequencing was performed as described previously (21). Briefly, sequencing libraries were created by shearing 250 ng of ERK1/2 amplified cDNA on a Covaris sonicator (Duty Cycle 10%, Intensity 5%, Cycles per Burst 200 for 305 seconds) using standard protocols and Illumina TruSeq kits. Libraries were cleaned up following shearing and final PCR reactions using AMPure XP Beads (Agencourt). Illumina barcodes were added at the adaptor ligation step and the six samples were pooled into one v1 MiSeq lane for paired-end sequencing resulting in 100 base pair reads.

Analysis:

The short reads to ERK1/2 cDNA sequences were aligned using Bowtie2 algorithm (37). Then we called the mutations using Samtools mpileup (38) with option-Q 20 for using only bases with high sequencing quality. To assign a P-Value to the observed mutation rates, we estimated the null distribution of mutation rates by fitting a normal curve to the distribution of the log transformed observed mutation rates for all the positions along the CDNA sequence. We excluded 50 bases from both ends of the CDNA sequence. We also excluded positions with observed mutation rate exceeding 0.01 or less than 1E-10. We then assigned a P-Value to each observed mutation rate using this null distribution and used Holm-Bonferroni correction method to calculate the FDR values. We used mutation rate corresponding to FDR=5% as the cut-off.

Growth Assays:

A375, WM266.4, or SKmel19 cells were plated in 96-well plates, with six replicates for each drug. Drugs were added the next day with or without DOX. Cell growth was analyzed 72-96 hours later by MTS assay (Promega). The inhibitor concentrations were the same as the screen. The alleles were also tested with dabrafenib (GSK'436) at a dose that elicited similar cell growth arrest as the other drugs (50 nM). Growth was normalized to DMSO, NO-DOX controls, and graphed as percent growth. Heatmaps were created from growth assays using GENE-E (Available on the World Wide Web at broadinstitute.org/cancer/software/GENE-E/download.html). For some growth assays, a half-log dose response curve was generated to determine sensitivity. The concentration of DMSO was 0.1%.

Western Blotting:

Cells were exposed to DOX with or without MAPK inhibitor at the same doses used in the screen for 24 h, then harvested in RIPA buffer, and run on SDS-PAGE. Proteins were transferred to PVDF membranes and analyzed using the following antibodies phosphoERK1/2, ERK1/2, phosphoELK-1 S383 (Santa Cruz), phosphoRSK (S380), RSK, tubulin, DUSP6 (Cell Signaling), cyclin D1 (Thermo Scientific), and V5 (Abcam). Relative expression was calculated by comparing densities of bands of phoshoELK-1 to total ERK (or V5). Values were normalized to untreated WT, which was set at 1.

IP Kinase Assays:

ERK1 and ERK2 open constructs were transferred into DEST40 (C-terminal V5 tag) vector (Invitrogen) using LR clonase II. A375 cells were transiently transfected with V5-tagged ERK1 or ERK2 constructs using X-tremeGENE HP (Roche). Cells were harvested the next day using 1× cell lysis buffer (Cell Signaling 200 µL of each lysate was added to 20 µL of V5-agarose beads (Sigma) and rotated at 4 degrees overnight. The next day, beads were wash 2× in lysis buffer and 2× in 1× kinase assay buffer (Cell Signaling). The beads were then incubated in 50 µL kinase buffer with 0.25 mg ELK-1 fusion protein (Cell Signaling) and 100 µM ATP (Cell Signaling) for 30 min at 30 deg C. with shaking. For ERK inhibitor studies, DMSO or VX-11e (0.1 µM) was added as indicated at 1:1000 dilution. For MEK inhibitor studies, trametnib was added to cells prior to harvest (3 nM, 4 h). Reactions were stopped with the addition on 3× SDS loading buffer. Samples were boiled and supernatant was run on SDS-PAGE gel for western blotting.

Site-Directed Mutagenesis:

Primers were designed using QuickChange Site-Directed Mutagenesis Protocol (Agilent) and are listed in the supplemental methods. PCR was performed using iProof DNA polymerase and GC buffer using primers specific for each mutation. Mutations were confirmed by Sanger sequencing.

Except the screen, all experiments were repeated at least three times, with representative graphs or blots shown. Error bars represent standard deviation.

Co-Occurring Mutations

To calculate the co-mutation rates, a tool in Java was developed using some of the Picard libraries (Available on the World Wide Web at picard.sourceforge.net). For each pair of mutations, the number of paired-end reads that spanned both of the mutations was counted and calculated the fraction with both of the mutations co-occurring.

Even though this screen nominated over 20 validated alleles resistant to RAF/MEK and ERK inhibitors, several of the alleles from the screen did not validate, despite some having a high frequency of alteration (Tables 4 and 5, FIG. 12E). For some alleles, it was understandable why they might not confer resistance. For example, we found two silent mutations that were significantly altered in the ERK inhibitor resistant screen, ERK1$^{G23G}$ and ERK2$^{V104V}$. Given recent evidence that silent mutations might play a role in regulation of protein translation, resulting in altered protein folding (39), we decided to test these alterations, given the high frequency of mutation (ERK1$^{G23G}$ was mutated at 7.2%). However, these silent mutations in ERK were indistinguishable from WT ERK (FIG. 12).

Given the method of mutagenesis, mutations that occurred early during mutagenesis could be carried to subsequent generations. Therefore, we analyzed the sequencing data to determine if there were co-occuring alterations. Since paired end reads were approximately 100 base pairs long, we could examine co-occuring alterations on the same reads (Methods). Even though we didn't find co-occuring alterations with the silent mutations, another allele that did not validate, ERK1$^{Y60C}$, was found to exclusively co-occur with ERK1$^{Y81C}$ and ERK1$^{Y53C}$ (FIG. 13A). ERK1$^{Y81C}$ was validated to confer resistance to VX-11e, and while ERK1$^{Y53C}$ was not tested, mutation of tyrosine 53 to another amino acid, ERK1$^{Y53H}$, did confer resistance (FIG. 2A). Since the read lengths restrict our detection of co-occuring events to within ~200 bp, we cannot detect all co-occuring alterations.

Co-occurring mutations were also identified in the RAF/MEKi screens and were able to find the non-validating mutant, ERK1$^{S74G}$, was almost exclusively co-mutated with the validated RAF/MEKi allele ERK1$^{Q90R}$ (FIG. 4A) as well as three other untested alleles (ERK1$^{K72R}$, ERK1$^{S57G}$, ERK1$^{K65R}$) (FIG. 13B). In the ERK2+MEKi and RAF+MEKi screens, there were also strings of mutations, including ERK2$^{E322K}$, ERK2$^{D337N}$, ERK2$^{E349K}$, and ERK2$^{R353K}$ (FIG. S6C). In all these strings of mutations, the mutations are GA to AA transition mutations, suggesting bias with random mutagenesis using XL-1 Red. Indeed, in a comparison of random mutagenesis methods, XL-1 Red is biased toward transition mutations (40). This suggests that this screen may not be completely saturating, and there could still be other alterations in ERK1/2 that could confer resistance. Still, using this method, we were able to identify and validate mutations in ERK1/2 that could confer resistance to RAF/MEK or ERK inhibitors.

Additionally, the co-occuring mutations of potential ERK1/2 double mutants that might be more active than single mutations were analyzed. There were two co-occurring mutations in the ERK1 MEKi screen with already validated alleles (FIG. 13B), so we made double mutants and compared them to the single mutations. However, these double mutants, ERK1$^{Q90R/Y148H}$ and ERK1$^{Y148H/S219P}$, were indistinguishable from the single mutations ERK1$^{Q90R}$ and ERK1$^{S219P}$ (FIG. 13D).

ENU Mutagenesis:

A375 cells were grown overnight in 50 µg/mL ethylnitrosourea (ENU). The next day cells were washed 3×, then let recover for 24 hours. Cells were then incubated with the RAF inhibitor, PLX-4720 (2 µM; a tool compound related to vemurafenib) or the MEK inhibitor, AZD6244 (1.5 µM). Colonies started appearing after 2.5 weeks in PLX-4720 or AZD6244 only in the ENU mutagenized cells. A375 cells that were not mutagenized did not have colonies. Colonies were picked and expanded for further analysis.

TABLE 6

Primer sequences

| FOR primers: | | SEQ ID NO |
|---|---|---|
| pCW57.1 FWD | TGG AGA ATT GGC TAG CAT CA | 5 |
| pCW57.1 REV | TGG TGG ACC GGT TCA TTA CT | 6 |
| 5' pWZL (long#2) | CGA TCC TCC CTT TAT CCA GCC CTC ACT CCT TCT CTA GG | 7 |
| 3'pWZL -20 | GGT GGA AAA TAA CCG GAA TTG GTC GAG ACA AGT TTG | 8 |
| Site directed mutagenesis primers: | | |
| ERK1 'open' | GTG CTG GAG GCC CCC TTG CCA ACT TTC TT | 9 |
| GC-ERK1 'open' | AAG AAA GTT GGC AAG GGG GCC TCC AGC AC | 10 |
| ERK1 G23G | GTC GGC CCG GGA GTC CGG GGG | 11 |
| GC-ERK1 G23G | CCC CGG GAC TCC CGG GCC GAC | 12 |
| ERK1 V28G | GTC CCG GGG GAG GGG GAG ATG GTG AAG | 13 |
| GC-ERK1 V28G | CTT CAC CAT CTC CCC CTC CCC CGG GAC | 14 |
| ERK1 V31G | GAG GTG GAG ATG GGG AAG GGG CAG CCG TTC | 15 |
| GC-ERK1 V31G | GAA CGG CTG CCC CTT CCC CAT CTC CAC CTC | 16 |
| ERK1 I48N | GCA GTT GCA GTA CAA CGG CGA GGG CG | 17 |
| GC-ERK1 I48N | CGC OCT CGC CGT TGT ACT GCA ACT GC | 18 |
| ERK1 Y53H | CGA GGG CGC GCA CGG CAT GGT CAG C | 19 |
| GC-ERK1 Y53H | GCT GAC CAT GCC GTG CGC GCC CTC G | 20 |
| ERK1 G54A | GGG CGC GTA CGC CAT GGT CAG CTC G | 21 |
| GC-ERK1 G54A | CGA GCT GAC CAT GGC GTA CGC GCC C | 22 |
| ERK1 Y60O | GCT CGG CCT GTG ACC ACG TGC GCA AG | 23 |
| GC-ERK1 Y60O | CTT GCG CAC GTG GTC ACA GGC CGA GC | 24 |
| ERK1 V63G | CTA TGA CCA CGG CGC AAG GAC TCG CGT G | 25 |
| GC-ERK1 V63G | CAC GCG AGT CTT GCG CCC GTG GTC ATA G | 26 |
| ERK1 K71R | CGC GTG GCC ATC AGG AAG ATC AGC CCC | 27 |
| GC-ERK1 K71R | GGG GCT GAT CTT CCT GAT GGC CAC GCG | 28 |
| ERK1 S74G | CAT CAA GAA GAT CGG CCC CTT CGA ACA TCA GAC C | 29 |
| GC-ERK1 S74G | GGT CTG ATG TTC GAA GGG GCC GAT CTT CTT GAT G | 30 |
| ERK1 P75L | CCA TCA AGA AGA TCA GCC TCT TCG AAC ATC AGA CC | 31 |
| GC-ERK1 P75L | GGT CTG ATG TTC GAA GAG GCT GAT CTT CTT GAT GG | 32 |

TABLE 6-continued

| Primer sequences | | |
|---|---|---|
| ERK1 Y810 | CTT CGA ACA TCA GAC CTG CTG CCA GCG CAC | 33 |
| GC-ERK1 Y810 | GTG CGC TGG CAG CAG GTC TGA TGT TCG AAG | 34 |
| ERK1 C82Y | CGA ACA TCA GAC CTA CTA CCA GCG CAC GCT CC | 35 |
| GC-ERK1 C82Y | GGA GCG TGC GCT GGT AGT AGG TCT GAT GTT CG | 36 |
| ERK1 R84H | CAG ACC TAC TGC CAG CAC ACG CTC CGG | 37 |
| GC-ERK1 R84H | CCG GAG CGT GTG CTG CCA GTA GGT CTG | 38 |
| ERK1 Q90R | CAC GCT CCG GGA GAT CCG GAT CCT GCT G | 39 |
| GC-ERK1 Q90R | CAG CAG GAT CCG GAT CTC CCG GAG CGT G | 40 |
| ERK1 Y148H | CCA TAT CTG CTA CTT CCT CCA CCA GAT CCT GCG | 41 |
| GC-ERK1 Y148H | CGC AGG ATC TGG TGG AGG AAG TAG CAG ATA TGG | 42 |
| ERK1 T176P | OCT GCT CAT CAA CCC CAC CTG CGA CCT TAA G | 43 |
| GC-ERK1 T176P | CTT AAG GTC GCA GGT GGG GTT GAT GAG CAG G | 44 |
| ERK1 T177P | CCT GCT CAT CAA CAC CCC CTG CGA CCT TAA G | 45 |
| GC-ERK1 T177P | CTT AAG GTC GCA GGG GGT GTT GAT GAG CAG G | 46 |
| ERK1 G186D | GAT TTG TGA TTT CGA CCT GGC CCG GAT TGC CG | 47 |
| GC-ERK1 G186D | CGG CAA TCC GGG CCA GGT CGA AAT CAC AAA TC | 48 |
| ERK1 A206V | GAC GGG AGT ATG TGG TTA CGC GCT GGT AC | 49 |
| GC-ERK1 A206V | GTA CCA GCG CGT AAC CAC ATA CTC CCG TC | 50 |
| ERK1 M216I | CCC AGA GAT CAT TCT GAA CTC CAA GGG CTA TAC C | 51 |
| GC-ERK1 M216I | GGT ATA GCC CTT GGA GTT CAG AAT GAT CTC TGG G | 52 |
| ERK1 S219P | CAG AGA TCA TGC TGA ACC CCA GGG CTA TAC C | 53 |
| GC-ERK1 S219P | GGT ATA GCC CTT GGG GTT CAG CAT GAT CTC TG | 54 |
| ERK1 A303V | GTC AGA CTC CAA AGT CCT TGA CCT GCT GGA C | 55 |
| GC-ERK1 A303V | GTC CAG CAG GTC AAG GAC TTT GGA GTC TGA C | 56 |
| ERK1 Y329C | GCT CAC CCC TGC CTG GAG CAG TAC TAT G | 57 |
| GC-ERK1 Y329C | CAT AGT ACT GCT CCA GGC AGG GGT GAG C | 58 |
| ERK1 D338N | ACT ATG ACC CGA CGA ATG AGC CAG TGG CC | 59 |
| GC-ERK1 D338N | GGC CAC TGG CTC ATT CGT CGG GTC ATA GT | 60 |
| ERK1 E339K | GAC CCG ACG GAT AAG CCA GTG GCC GAG G | 61 |
| GC-ERK1 E339K | CCT CGG CCA CTG GCT TAT CCG TCG GGT C | 62 |
| ERK1 T347A | GAG CCC TTC GCC TTC GCC ATG GAG CTG | 63 |
| GC-ERK1 T347A | CAG CTC CAT GGC GAA GGC GAA GGG CTC | 64 |
| ERK2 'open' | TTC CAG CCA GGA TAC AGA TCT TTG CCA ACT TTC TTG | 65 |
| GC-ERK2 'open' | CAA GAA AGT TGG CAA AGA TCT GTA TCC TGG CTG GAA | 66 |
| ERK2 Y36N | CGA GGG CGC CAA CGG CAT GGT GTG C | 67 |
| GC-ERK2 Y36N | GCA CAC CAT GCC GTT GGC GCC CTC G | 68 |
| ERK2 Y36H | CGA GGG CGC CCA CGG CAT GGT GTG C | 69 |
| GC-ERK2 Y36H | GCA CAC CAT GCC GTG GGC GCC CTC G | 70 |

TABLE 6-continued

| Primer sequences | | |
|---|---|---|
| ERK2 G37S | GAG GGC GCC TAC AGC ATG GTG TGC TCT G | 71 |
| GC-ERK2 G37S | CAG AGC ACA CCA TGC TGT AGG CGC CCT C | 72 |
| ERK2 K54R | AAA GTT CGA GTA GCT ATC AGG AAA ATC AGC CCC TTT GAG | 73 |
| GC-ERK2 K54R | CTC AAA GGG CTG ATT TTC CTG ATA GCT ACT CGA ACT TT | 74 |
| ERK2 P58T | GCT ATC AAG AAA ATC AGC ACC TTT GAG CAC CAG ACC | 75 |
| GC-ERK2 P58T | GGT CTG GTG CTC AAA GGT GCT GAT TTT CTT GAT AGC | 76 |
| ERK2 P58S | GCT ATC AAG AAA ATC AGC TCC TTT GAG CAC CAG ACC | 77 |
| GC-ERK2 P58S | GGT CTG GTG CTC AAA GGA GCT GAT TTT CTT GAT AGC | 78 |
| ERK2 Y64N | GCA CCA GAC CAA CTG CCA GAG AAC CCT G | 79 |
| GC-ERK2 Y64N | CAG GGT TCT CTG GCA GTT GGT CTG GTG C | 80 |
| ERK2 C65Y | GAG CAC CAG ACC TAC TAC CAG AGA ACC CTG AG | 81 |
| GC-ERK2 C65Y | CTC AGG GTT CTC TGG TAG TAG GTC TGG TGC TC | 82 |
| ERK2 V39G | CGC CTA CGG CAT GGG GTG CTC TGC TTA TG | 83 |
| GC-ERK2 V39G | CAT AAG CAG AGC ACC CCA TGC CGT AGG CG | 84 |
| ERK2 P58L | GCT ATC AAG AAA ATC AGC CTC TTT GAG CAC CAG ACC | 85 |
| GC-ERK2 P58L | GGT CTG GTG CTC AAA GAG GCT GAT TTT CTT GAT AGC | 86 |
| ERK2 R67K | CCA GAC CTA CTG CCA GAA AAO CCT GAG GGA G | 87 |
| GC-ERK2 R67K | CTC CCT CAG GGT TTT CTG GCA GTA GGT CTG G | 88 |
| ERK2 Q105A | CCA TCG AGC AAA TGA AGG ATG TAT ATA TAG TAG CGG ACC TCA TGG | 89 |
| GC-ERK2 Q105A | CCA TGA GGT CCG CTA CTA TAT ATA CAT CTT TCA TTT GCT CGA TGG | 90 |
| ERK2 H120P | GCT CTT GAA GAC ACA ACC CCT CAG CAA TGA CC | 91 |
| GC - ERK2 H120P | GGT CAT TGC TGA GGG GTT GTG TCT TCA AGA GC | 92 |
| ERK2 Y131F | GAC CAT ATC TGC TAT TTT CTC TTC CAG ATC CTC AGA GGG | 93 |
| GC-ERK2 Y131F | CCC TCT GAG GAT CTG GAA GAG AAA ATA GCA GAT ATG GTC | 94 |
| ERK2 T159P | CCT GCT GCT CAA CCC CAC CTG TGA TCT CAA G | 95 |
| GC-ERK2 T159P | CTT GAG ATC ACA GGT GGG GTT GAG CAG CAG G | 96 |
| ERK2 T160P | GCT GCT CAA CAC CCC CTG TGA TCT CAA GAT C | 97 |
| GC-ERK2 T160P | GAT CTT GAG ATC ACA GGG GGT GTT GAG CAG C | 98 |
| ERK2 V214A | CCA TTG ATA TTT GGT CTG CAG GCT GCA TTC TGG CAG | 99 |
| GC-ERK2 V214A | CTG CCA GAA TGC AGC CTG CAG ACC AAA TAT CAA TGG | 100 |
| ERK2 D321G | GTA TTA CGA CCC GAG TGG CGA GCC CAT CG | 101 |
| GC-ERK2 D321G | CGA TGG GCT CGC CAC TCG GGT CGT AAT AC | 102 |

TABLE 6-continued

Primer sequences

| | | |
|---|---|---|
| ERK2 D321N | GAG CAG TAT TAC GAC CCG AGT AAO GAG CCC ATC | 103 |
| GC-ERK2 D321N | GAT GGG CTC GTT ACT CGG GTC GTA ATA CTG CTC | 104 |
| ERK2 E322K | CGA CCC GAG TGA CAA GCC CAT CGC CGA AGC | 105 |
| GC-ERK2 E322K | GCT TCG GCG ATG GGC TTG TCA CTC GGG TCG | 106 |
| ERK2 P323S | CGA GTG ACG AGT CCA TCG CCG AAG CAC C | 107 |
| GC-ERK2 P323S | GGT GCT TCG GCG ATG GAC TCG TCA CTC G | 108 |
| ERK2 V104V | GCA AAT GAA AGA TGT ATA TAT AGT GCA GGA CCT CAT GGA AAC | 109 |
| GC-ERK2 V104V | GTT CCA TGA GGT CCT GCA CTA TAT ACA TCT TTC ATT TGC | 110 |
| ERK2 A189V | GAC AGA ATA TGT GGT CAC ACG TTG GTA CAG GGC | 111 |
| GC-ERK2 A189V | GCC CTG TAC CAA CGT GTG ACC ACA TAT TCT GTC | 112 |
| ERK2 S202P | CCA GAA ATT ATG TTG AAT CCC AAG GGC TAC ACC AAG | 113 |
| GC-ERK2 S202P | CTT GGT GTA GCC CTT GGG ATT CAA CAT AAT TTC TGG | 114 |
| ERK2 Y205N | GTT GAA TTC AAA GGG CAA CAC CAA GTC CAT TGA TAT TTG | 115 |
| GC-ERK2 Y205N | CAA ATA TCA ATG GAC TTG GTG TTG CCC TTG GAA TTC AAC | 116 |

The definitions and disclosures provided herein govern and supersede all others incorporated by reference. Although the invention herein has been described in connection with preferred embodiments thereof, it will be appreciated by those skilled in the art that additions, modifications, substitutions, and deletions not specifically described may be made without departing from the spirit and scope of the invention as defined in the appended claims. It is therefore intended that the foregoing detailed description be regarded as illustrative rather than limiting, and that it be understood that it is the following claims, including all equivalents, that are intended to define the spirit and scope of this invention.

REFERENCES

1. Davies H, Bignell G R, Cox C, Stephens P, Edkins S, Clegg S, et al. Mutations of the BRAF gene in human cancer. Nature. 2002; 417:949-54.
2. Flaherty K T, Infante J R, Daud A, Gonzalez R, Kefford R F, Sosman J, et al. Combined BRAF and MEK inhibition in melanoma with BRAF V600 mutations. The New England journal of medicine. 2012; 367:1694-703.
3. Chapman P B, Hauschild A, Robert C, Haanen J B, Ascierto P, Larkin J, et al. Improved survival with vemurafenib in melanoma with BRAF V600E mutation. The New England journal of medicine. 2011; 364:2507-16.
4. Flaherty K T, Puzanov I, Kim K B, Ribas A, McArthur G A, Sosman J A, et al. Inhibition of mutated, activated BRAF in metastatic melanoma. The New England journal of medicine. 2010; 363:809-19.
5. Flaherty K T, Robert C, Hersey P, Nathan P, Garbe C, Milhem M, et al. Improved survival with MEK inhibition in BRAF-mutated melanoma. The New England journal of medicine. 2012; 367:107-14.
6. Trunzer K, Pavlick A C, Schuchter L, Gonzalez R, McArthur G A, Hutson T E, et al. Pharmacodynamic effects and mechanisms of resistance to vemurafenib in patients with metastatic melanoma. Journal of clinical oncology: official journal of the American Society of Clinical Oncology. 2013; 31:1767-74.
7. Van Allen E M, Wagle N, Sucker A, Treacy D J, Johannessen C M, Goetz E M, et al. The genetic landscape of clinical resistance to RAF inhibition in metastatic melanoma. Cancer discovery. 2014; 4:94-109.
8. Wagle N, Van Allen E M, Treacy D J, Frederick D T, Cooper Z A, Taylor-Weiner A, et al. MAP kinase pathway alterations in BRAF-mutant melanoma patients with acquired resistance to combined RAF/MEK inhibition. Cancer discovery. 2014; 4:61-8.
9. Nazarian R, Shi H, Wang Q, Kong X, Koya R C, Lee H, et al. Melanomas acquire resistance to B-RAF(V600E) inhibition by RTK or N-RAS upregulation. Nature. 2010; 468:973-7.
10. Poulikakos P I, Persaud Y, Janakiraman M, Kong X, Ng C, Moriceau G, et al. RAF inhibitor resistance is mediated by dimerization of aberrantly spliced BRAF(V600E). Nature. 2011; 480:387-90.
11. Johannessen C M, Boehm J S, Kim S Y, Thomas S R, Wardwell L, Johnson L A, et al. COT drives resistance to RAF inhibition through MAP kinase pathway reactivation. Nature. 2010; 468:968-72.
12. Mandl M, Slack D N, Keyse S M. Specific inactivation and nuclear anchoring of extracellular signal-regulated kinase 2 by the inducible dual-specificity protein phosphatase DUSP5. Molecular and cellular biology. 2005; 25:1830-45.
13. Muda M, Theodosiou A, Rodrigues N, Boschert U, Camps M, Gillieron C, et al. The dual specificity phosphatases M3/6 and MKP-3 are highly selective for inactivation of distinct mitogen-activated protein kinases. The Journal of biological chemistry. 1996; 271:27205-8.
14. Zhang Z, Kobayashi S, Borczuk A C, Leidner R S, Laframboise T, Levine A D, et al. Dual specificity phosphatase 6 (DUSP6) is an ETS-regulated negative feedback mediator of oncogenic ERK signaling in lung cancer cells. Carcinogenesis. 2010; 31:577-86.
15. Roskoski R, Jr. ERK1/2 MAP kinases: structure, function, and regulation. Pharmacological research: the official journal of the Italian Pharmacological Society. 2012; 66:105-43.
16. Fritsche-Guenther R, Witzel F, Sieber A, Herr R, Schmidt N, Braun S, et al. Strong negative feedback from Erk to Raf confers robustness to MAPK signalling. Molecular systems biology. 2011; 7:489.
17. Ojesina A I, Lichtenstein L, Freeman S S, Pedamallu C S, Imaz-Rosshandler I, Pugh T J, et al. Landscape of genomic alterations in cervical carcinomas. Nature. 2014; 506:371-5.
18. Arvind R, Shimamoto H, Momose F, Amagasa T, Omura K, Tsuchida N. A mutation in the common docking domain of ERK2 in a human cancer cell line, which was associated with its constitutive phosphorylation. International journal of oncology. 2005; 27:1499-504.
19. Bott C M, Thorneycroft S G, Marshall C J. The sevenmaker gain-of-function mutation in p42 MAP kinase leads to enhanced signalling and reduced sensitivity to dual specificity phosphatase action. FEBS letters. 1994; 352:201-5.
20. Ray A, Cowan-Jacob S W, Manley P W, Mestan J, Griffin J D. Identification of BCR-ABL point mutations conferring resistance to the Abl kinase inhibitor AMN107 (nilotinib) by a random mutagenesis study. Blood. 2007; 109:5011-5.
21. Emery C M, Vijayendran K G, Zipser M C, Sawyer A M, Niu L, Kim J J, et al. MEK1 mutations confer resistance to MEK and B-RAF inhibition. Proceedings of the National Academy of Sciences of the United States of America. 2009; 106:20411-6.
22. Muteeb G, Sen R. Random mutagenesis using a mutator strain. Methods in molecular biology. 2010; 634:411-9.
23. Aronov A M, Tang Q, Martinez-Botella G, Bemis G W, Cao J, Chen G, et al. Structure-guided design of potent and selective pyrimidylpyrrole inhibitors of extracellular signal-regulated kinase (ERK) using conformational control. Journal of medicinal chemistry. 2009; 52:6362-8.
24. Robinson M J, Harkins P C, Zhang J, Baer R, Haycock J W, Cobb M H, et al. Mutation of position 52 in ERK2 creates a nonproductive binding mode for adenosine 5'-triphosphate. Biochemistry. 1996; 35:5641-6.
25. Burkhard K A, Chen F, Shapiro P. Quantitative analysis of ERK2 interactions with substrate proteins: roles for kinase docking domains and activity in determining binding affinity. The Journal of biological chemistry. 2011; 286:2477-85.
26. Lee T, Hoofnagle A N, Kabuyama Y, Stroud J, Min X, Goldsmith E J, et al. Docking motif interactions in MAP kinases revealed by hydrogen exchange mass spectrometry. Molecular cell. 2004; 14:43-55.
27. Hatzivassiliou G, Liu B, O'Brien C, Spoerke J M, Hoeflich K P, Haverty P M, et al. ERK inhibition overcomes acquired resistance to MEK inhibitors. Molecular cancer therapeutics. 2012; 11:1143-54.
28. Boulton T G, Gregory J S, Cobb M H. Purification and properties of extracellular signal-regulated kinase 1, an insulin-stimulated microtubule-associated protein 2 kinase. Biochemistry. 1991; 30:278-86.
29. Robbins D J, Zhen E, Owaki H, Vanderbilt C A, Ebert D, Geppert T D, et al. Regulation and properties of extracellular signal-regulated protein kinases 1 and 2 in vitro. The Journal of biological chemistry. 1993; 268: 5097-106.
30. Lefloch R, Pouyssegur J, Lenormand P. Total ERK1/2 activity regulates cell proliferation. Cell cycle. 2009; 8:705-11.
31. Yao Y, Li W, Wu J, Germann U A, Su M S, Kuida K, et al. Extracellular signal-regulated kinase 2 is necessary for mesoderm differentiation. Proceedings of the National Academy of Sciences of the United States of America. 2003; 100:12759-64.
32. Das Thakur M, Salangsang F, Landman A S, Sellers W R, Pryer N K, Levesque M P, et al. Modelling vemurafenib resistance in melanoma reveals a strategy to forestall drug resistance. Nature. 2013; 494:251-5.
33. Sun C, Wang L, Huang S, Heynen G J, Prahallad A, Robert C, et al. Reversible and adaptive resistance to BRAF(V600E) inhibition in melanoma. Nature. 2014; 508:118-22.
34. Guerreschi P, Scalbert C, Qassemyar A, Kluza J, Ravasi L, Huglo D, et al. Patient-derived tumor xenograft model to guide the use of BRAF inhibitors in metastatic melanoma. Melanoma research. 2013.
35. Romano E, Pradervand S, Paillusson A, Weber J, Harshman K, Muehlethaler K, et al. Identification of multiple mechanisms of resistance to vemurafenib in a patient with BRAFV600E-mutated cutaneous melanoma successfully rechallenged after progression. Clinical cancer research: an official journal of the American Association for Cancer Research. 2013; 19:5749-57.
36. Seghers A C, Wilgenhof S, Lebbe C, Neyns B. Successful rechallenge in two patients with BRAF-V600-mutant melanoma who experienced previous progression during treatment with a selective BRAF inhibitor. Melanoma research. 2012; 22:466-72.
37. Langmead B, Salzberg S L. Fast gapped-read alignment with Bowtie 2. Nature methods. 2012; 9:357-9.
38. Li H, Handsaker B, Wysoker A, Fennell T, Ruan J, Homer N, et al. The Sequence Alignment/Map format and SAMtools. Bioinformatics. 2009; 25:2078-9.
39. Kimchi-Sarfaty C, Oh J M, Kim I W, Sauna Z E, Calcagno A M, Ambudkar S V, et al. A "silent" polymorphism in the MDR1 gene changes substrate specificity. Science. 2007; 315:525-8.
40. Rasila T S, Pajunen M I, Savilahti H. Critical evaluation of random mutagenesis by error-prone polymerase chain reaction protocols, *Escherichia coli* mutator strain, and hydroxylamine treatment. Analytical biochemistry. 2009; 388:71-80.

The invention claimed is:

1. A method of treating a subject having a cancer, the method comprising:
   detecting in cancer cells obtained from the subject a C82Y mutation in a nucleic acid molecule encoding an ERK1 polypeptide;
   wherein the presence of the mutation in the ERK1 polypeptide identifies the subject as being resistant to treatment with an ERK small molecule inhibitor; and
   administering to the subject a MAPK pathway inhibitor that is not an ERK inhibitor.

2. The method according to claim 1, wherein the presence of the C82Y mutation in the ERK1 polypeptide identifies the subject as being nonresponsive to treatment with the ERK inhibitor.

3. The method according to claim 1, wherein the presence of the C82Y mutation in the ERK1 polypeptide:
   a) identifies the subject for selection for treatment with a second MAPK pathway inhibitor that is not an ERK inhibitor, wherein the MAPK pathway inhibitor that is not an ERK inhibitor is a MEK or RAF inhibitor; or
   b) indicates that the subject should stop receiving treatment with the ERK inhibitor.

4. The method according to claim 1, wherein the ERK inhibitor comprises VX-11e or SCH-772984.

5. An in vitro method of screening a cancer cell-containing sample for an ERK mutation, the method comprising:
   detecting in the sample a C82Y mutation in a nucleic acid molecule encoding an ERK by sequencing at least the portion of the nucleic molecule encoding residue 82 of the ERK polypeptide and detecting the C82Y mutation.

6. The method according to claim 1, wherein the cancer is selected from the group consisting of leukemias, lymphomas, myelomas, carcinomas, metastatic carcinomas, sarcomas, adenomas, nervous system cancers and genitourinary cancers.

7. The method of claim 1, wherein the cancer is melanoma.

8. The method according to claim 5, wherein the cancer is selected from the group consisting of leukemias, lymphomas, myelomas, carcinomas, metastatic carcinomas, sarcomas, adenomas, nervous system cancers and genitourinary cancers.

9. The method of claim 5, wherein the cancer is melanoma.

* * * * *

SEQUENCE LISTING

<160> NUMBER OF SEQ ID NOS: 116

<210> SEQ ID NO 1

<211> LENGTH: 1140
<212> TYPE: DNA
<213> ORGANISM: Homo sapiens

<400> SEQUENCE: 1

```
atggcggcgg cggcggctca ggggggcggg ggcggggagc cccgtagaac cgaggggggtc      60
ggcccggggg tcccggggga ggtggagatg gtgaaggggc agccgttcga cgtgggcccg     120
cgctacacgc agttgcagta catcggcgag ggcgcgtacg gcatggtcag ctcggcctat     180
gaccacgtgc gcaagactcg cgtggccatc aagaagatca gccccttcga acatcagacc     240
tactgccagc gcacgctccg ggagatccag atcctgctgc gcttccgcca tgagaatgtc     300
atcggcatcc gagacattct gcgggcgtcc accctggaag ccatgagaga tgtctacatt     360
gtgcaggacc tgatggagac tgacctgtac aagttgctga aaagccagca gctgagcaat     420
gaccatatct gctacttcct ctaccagatc ctgcggggcc tcaagtacat ccactccgcc     480
aacgtgctcc accgagatct aaagccctcc aacctgctca tcaacaccac ctgcgacctt     540
aagatttgtg atttcggcct ggcccggatt gccgatcctg agcatgacca caccggcttc     600
ctgacggagt atgtggctac gcgctggtac cgggccccag agatcatgct gaactccaag     660
ggctatacca agtccatcga catctggtct gtgggctgca ttctggctga gatgctctct     720
aaccggccca tcttccctgg caagcactac ctggatcagc tcaaccacat tctgggcatc     780
ctgggctccc catcccagga ggacctgaat tgtatcatca acatgaaggc ccgaaactac     840
ctacagtctc tgccctccaa gaccaaggtg gcttgggcca gcttttccc caagtcagac     900
tccaaagccc ttgacctgct ggaccggatg ttaaccttta accccaataa acggatcaca     960
gtggaggaag cgctggctca cccctacctg gagcagtact atgacccgac ggatgagcca    1020
gtggccgaga gcccttcac cttcgccatg gagctggatg acctacctaa ggagcggctg    1080
aaggagctca tcttccagga gacagcacgc ttccagcccg gagtgctgga ggccccctag    1140
```

<210> SEQ ID NO 2
<211> LENGTH: 1083
<212> TYPE: DNA
<213> ORGANISM: Homo sapiens

<400> SEQUENCE: 2

```
atggcggcgg cggcggcggc gggcgcgggc ccggagatgg tccgcgggca ggtgttcgac      60
gtggggccgc gctacaccaa cctctcgtac atcggcgagg gcgcctacgg catggtgtgc     120
tctgcttatg ataatgtcaa caaagttcga gtagctatca gaaaaatcag ccccttgag     180
caccagacct actgccagag aaccctgagg gagataaaaa tcttactgcg cttcagacat     240
gagaacatca ttggaatcaa tgacattatt cgagcaccaa ccatcgagca atgaaaagat     300
gtatatatag tacaggacct catggaaaca gatctttaca agctcttgaa gacacaacac     360
ctcagcaatg accatatctg ctatttctc taccagatcc tcagagggtt aaaatatatc     420
cattcagcta acgttctgca ccgtgacctc aagccttcca acctgctgct caacaccacc     480
tgtgatctca agatctgtga ctttggcctg gcccgtgttg cagatccaga ccatgatcac     540
acagggttcc tgacagaata tgtggccaca cgttggtaca gggctccaga aattatgttg     600
aattccaagg gctacaccaa gtccattgat atttggtctg taggctgcat tctggcagaa     660
atgcttttcta acaggcccat cttccaaggg aagcattatc ttgaccagct gaaccacatt     720
ttgggtattc ttgatccccc atcacaagaa gacctgaatt gtataataaa tttaaaagct     780
aggaactatt tgcttttctct tccacacaaa aataaggtgc catggaacag gctgttccca     840
```

```
aatgctgact ccaaagctct ggacttattg acaaaatgt tgacattcaa cccacacaag        900
aggattgaag tagaacaggc tctggcccac ccatatctgg agcagtatta cgacccgagt        960
gacgagccca tcgccgaagc accattcaag ttcgacatgg aattggatga cttgcctaag       1020
gaaaagctca agaactaat ttttgaagag actgctagat tccagccagg atacagatct       1080
taa                                                                     1083
```

```
<210> SEQ ID NO 3
<211> LENGTH: 379
<212> TYPE: PRT
<213> ORGANISM: Homo sapiens

<400> SEQUENCE: 3
```

```
Met Ala Ala Ala Ala Gln Gly Gly Gly Gly Glu Pro Arg Arg
1               5                   10                  15

Thr Glu Gly Val Gly Pro Gly Val Pro Gly Glu Val Glu Met Val Lys
            20                  25                  30

Gly Gln Pro Phe Asp Val Gly Pro Arg Tyr Thr Gln Leu Gln Tyr Ile
        35                  40                  45

Gly Glu Gly Ala Tyr Gly Met Val Ser Ser Ala Tyr Asp His Val Arg
    50                  55                  60

Lys Thr Arg Val Ala Ile Lys Lys Ile Ser Pro Phe Glu His Gln Thr
65                  70                  75                  80

Tyr Cys Gln Arg Thr Leu Arg Glu Ile Gln Ile Leu Leu Arg Phe Arg
                85                  90                  95

His Glu Asn Val Ile Gly Ile Arg Asp Ile Leu Arg Ala Ser Thr Leu
            100                 105                 110

Glu Ala Met Arg Asp Val Tyr Ile Val Gln Asp Leu Met Glu Thr Asp
        115                 120                 125

Leu Tyr Lys Leu Leu Lys Ser Gln Gln Leu Ser Asn Asp His Ile Cys
    130                 135                 140

Tyr Phe Leu Tyr Gln Ile Leu Arg Gly Leu Lys Tyr Ile His Ser Ala
145                 150                 155                 160

Asn Val Leu His Arg Asp Leu Lys Pro Ser Asn Leu Leu Ile Asn Thr
                165                 170                 175

Thr Cys Asp Leu Lys Ile Cys Asp Phe Gly Leu Ala Arg Ile Ala Asp
            180                 185                 190

Pro Glu His Asp His Thr Gly Phe Leu Thr Glu Tyr Val Ala Thr Arg
        195                 200                 205

Trp Tyr Arg Ala Pro Glu Ile Met Leu Asn Ser Lys Gly Tyr Thr Lys
    210                 215                 220

Ser Ile Asp Ile Trp Ser Val Gly Cys Ile Leu Ala Glu Met Leu Ser
225                 230                 235                 240

Asn Arg Pro Ile Phe Pro Gly Lys His Tyr Leu Asp Gln Leu Asn His
                245                 250                 255

Ile Leu Gly Ile Leu Gly Ser Pro Ser Gln Glu Asp Leu Asn Cys Ile
            260                 265                 270

Ile Asn Met Lys Ala Arg Asn Tyr Leu Gln Ser Leu Pro Ser Lys Thr
        275                 280                 285

Lys Val Ala Trp Ala Lys Leu Phe Pro Lys Ser Asp Ser Lys Ala Leu
    290                 295                 300

Asp Leu Leu Asp Arg Met Leu Thr Phe Asn Pro Asn Lys Arg Ile Thr
305                 310                 315                 320
```

```
Val Glu Glu Ala Leu Ala His Pro Tyr Leu Glu Gln Tyr Tyr Asp Pro
            325                 330                 335

Thr Asp Glu Pro Val Ala Glu Pro Phe Thr Phe Ala Met Glu Leu
        340                 345                 350

Asp Asp Leu Pro Lys Glu Arg Leu Lys Glu Leu Ile Phe Gln Glu Thr
            355                 360                 365

Ala Arg Phe Gln Pro Gly Val Leu Glu Ala Pro
        370                 375

<210> SEQ ID NO 4
<211> LENGTH: 360
<212> TYPE: PRT
<213> ORGANISM: Homo sapiens

<400> SEQUENCE: 4

Met Ala Ala Ala Ala Ala Gly Ala Gly Pro Glu Met Val Arg Gly
1               5                  10                  15

Gln Val Phe Asp Val Gly Pro Arg Tyr Thr Asn Leu Ser Tyr Ile Gly
            20                  25                  30

Glu Gly Ala Tyr Gly Met Val Cys Ser Ala Tyr Asp Asn Val Asn Lys
        35                  40                  45

Val Arg Val Ala Ile Lys Lys Ile Ser Pro Phe Glu His Gln Thr Tyr
    50                  55                  60

Cys Gln Arg Thr Leu Arg Glu Ile Lys Ile Leu Leu Arg Phe Arg His
65                  70                  75                  80

Glu Asn Ile Ile Gly Ile Asn Asp Ile Ile Arg Ala Pro Thr Ile Glu
                85                  90                  95

Gln Met Lys Asp Val Tyr Ile Val Gln Asp Leu Met Glu Thr Asp Leu
            100                 105                 110

Tyr Lys Leu Leu Lys Thr Gln His Leu Ser Asn Asp His Ile Cys Tyr
        115                 120                 125

Phe Leu Tyr Gln Ile Leu Arg Gly Leu Lys Tyr Ile His Ser Ala Asn
    130                 135                 140

Val Leu His Arg Asp Leu Lys Pro Ser Asn Leu Leu Leu Asn Thr Thr
145                 150                 155                 160

Cys Asp Leu Lys Ile Cys Asp Phe Gly Leu Ala Arg Val Ala Asp Pro
                165                 170                 175

Asp His Asp His Thr Gly Phe Leu Thr Glu Tyr Val Ala Thr Arg Trp
            180                 185                 190

Tyr Arg Ala Pro Glu Ile Met Leu Asn Ser Lys Gly Tyr Thr Lys Ser
        195                 200                 205

Ile Asp Ile Trp Ser Val Gly Cys Ile Leu Ala Glu Met Leu Ser Asn
    210                 215                 220

Arg Pro Ile Phe Pro Gly Lys His Tyr Leu Asp Gln Leu Asn His Ile
225                 230                 235                 240

Leu Gly Ile Leu Gly Ser Pro Ser Gln Glu Asp Leu Asn Cys Ile Ile
                245                 250                 255

Asn Leu Lys Ala Arg Asn Tyr Leu Leu Ser Leu Pro His Lys Asn Lys
            260                 265                 270

Val Pro Trp Asn Arg Leu Phe Pro Asn Ala Asp Ser Lys Ala Leu Asp
        275                 280                 285

Leu Leu Asp Lys Met Leu Thr Phe Asn Pro His Lys Arg Ile Glu Val
    290                 295                 300

Glu Gln Ala Leu Ala His Pro Tyr Leu Glu Gln Tyr Tyr Asp Pro Ser
305                 310                 315                 320
```

```
Asp Glu Pro Ile Ala Glu Ala Pro Phe Lys Phe Asp Met Glu Leu Asp
            325                 330                 335

Asp Leu Pro Lys Glu Lys Leu Lys Glu Leu Ile Phe Glu Glu Thr Ala
        340                 345                 350

Arg Phe Gln Pro Gly Tyr Arg Ser
        355                 360
```

<210> SEQ ID NO 5
<211> LENGTH: 20
<212> TYPE: DNA
<213> ORGANISM: Artificial Sequence
<220> FEATURE:
<223> OTHER INFORMATION: pCW57.1 FWD primer

<400> SEQUENCE: 5
tggagaattg gctagcatca                                              20

<210> SEQ ID NO 6
<211> LENGTH: 20
<212> TYPE: DNA
<213> ORGANISM: Artificial Sequence
<220> FEATURE:
<223> OTHER INFORMATION: pCW57.1 REV

<400> SEQUENCE: 6
tggtggaccg gttcattact                                              20

<210> SEQ ID NO 7
<211> LENGTH: 38
<212> TYPE: DNA
<213> ORGANISM: Artificial Sequence
<220> FEATURE:
<223> OTHER INFORMATION: 5' pWZL (long#2)

<400> SEQUENCE: 7
cgatcctccc tttatccagc cctcactcct tctctagg                          38

<210> SEQ ID NO 8
<211> LENGTH: 36
<212> TYPE: DNA
<213> ORGANISM: Artificial Sequence
<220> FEATURE:
<223> OTHER INFORMATION: 3'pWZL -20

<400> SEQUENCE: 8
ggtggaaaat aaccggaatt ggtcgagaca agtttg                            36

<210> SEQ ID NO 9
<211> LENGTH: 29
<212> TYPE: DNA
<213> ORGANISM: Artificial Sequence
<220> FEATURE:
<223> OTHER INFORMATION: ERK1 'open'

<400> SEQUENCE: 9
gtgctggagg cccccttgcc aactttctt                                    29

<210> SEQ ID NO 10
<211> LENGTH: 29
<212> TYPE: DNA
<213> ORGANISM: Artificial Sequence
<220> FEATURE:
<223> OTHER INFORMATION: GC - ERK1 'open'

<400> SEQUENCE: 10

| | |
|---|---|
| aagaaagttg gcaaggggc ctccagcac | 29 |

<210> SEQ ID NO 11
<211> LENGTH: 21
<212> TYPE: DNA
<213> ORGANISM: Artificial Sequence
<220> FEATURE:
<223> OTHER INFORMATION: ERK1 G23G

<400> SEQUENCE: 11

| | |
|---|---|
| gtcggcccgg gagtcccggg g | 21 |

<210> SEQ ID NO 12
<211> LENGTH: 21
<212> TYPE: DNA
<213> ORGANISM: Artificial Sequence
<220> FEATURE:
<223> OTHER INFORMATION: GC - ERK1 G23G

<400> SEQUENCE: 12

| | |
|---|---|
| ccccgggact cccgggccga c | 21 |

<210> SEQ ID NO 13
<211> LENGTH: 27
<212> TYPE: DNA
<213> ORGANISM: Artificial Sequence
<220> FEATURE:
<223> OTHER INFORMATION: ERK1 V28G

<400> SEQUENCE: 13

| | |
|---|---|
| gtcccggggg aggggagat ggtgaag | 27 |

<210> SEQ ID NO 14
<211> LENGTH: 27
<212> TYPE: DNA
<213> ORGANISM: Artificial Sequence
<220> FEATURE:
<223> OTHER INFORMATION: GC - ERK1 V28G

<400> SEQUENCE: 14

| | |
|---|---|
| cttcaccatc tcccctccc ccgggac | 27 |

<210> SEQ ID NO 15
<211> LENGTH: 30
<212> TYPE: DNA
<213> ORGANISM: Artificial Sequence
<220> FEATURE:
<223> OTHER INFORMATION: ERK1 V31G

<400> SEQUENCE: 15

| | |
|---|---|
| gaggtggaga tggggaaggg gcagccgttc | 30 |

<210> SEQ ID NO 16
<211> LENGTH: 30
<212> TYPE: DNA
<213> ORGANISM: Artificial Sequence
<220> FEATURE:
<223> OTHER INFORMATION: GC - ERK1 V31G

<400> SEQUENCE: 16

| | |
|---|---|
| gaacggctgc cccttcccca tctccacctc | 30 |

<210> SEQ ID NO 17
<211> LENGTH: 26
<212> TYPE: DNA

```
<213> ORGANISM: Artificial Sequence
<220> FEATURE:
<223> OTHER INFORMATION: ERK1 I48N

<400> SEQUENCE: 17
gcagttgcag tacaacggcg agggcg                                          26

<210> SEQ ID NO 18
<211> LENGTH: 26
<212> TYPE: DNA
<213> ORGANISM: Artificial Sequence
<220> FEATURE:
<223> OTHER INFORMATION: GC - ERK1 I48N

<400> SEQUENCE: 18
cgccctcgcc gttgtactgc aactgc                                          26

<210> SEQ ID NO 19
<211> LENGTH: 25
<212> TYPE: DNA
<213> ORGANISM: Artificial Sequence
<220> FEATURE:
<223> OTHER INFORMATION: ERK1 Y53H

<400> SEQUENCE: 19
cgagggcgcg cacggcatgg tcagc                                           25

<210> SEQ ID NO 20
<211> LENGTH: 25
<212> TYPE: DNA
<213> ORGANISM: Artificial Sequence
<220> FEATURE:
<223> OTHER INFORMATION: GC - ERK1 Y53H

<400> SEQUENCE: 20
gctgaccatg ccgtgcgcgc cctcg                                           25

<210> SEQ ID NO 21
<211> LENGTH: 25
<212> TYPE: DNA
<213> ORGANISM: Artificial Sequence
<220> FEATURE:
<223> OTHER INFORMATION: ERK1 G54A

<400> SEQUENCE: 21
gggcgcgtac gccatggtca gctcg                                           25

<210> SEQ ID NO 22
<211> LENGTH: 25
<212> TYPE: DNA
<213> ORGANISM: Artificial Sequence
<220> FEATURE:
<223> OTHER INFORMATION: GC - ERK1 G54A

<400> SEQUENCE: 22
cgagctgacc atggcgtacg cgccc                                           25

<210> SEQ ID NO 23
<211> LENGTH: 26
<212> TYPE: DNA
<213> ORGANISM: Artificial Sequence
<220> FEATURE:
<223> OTHER INFORMATION: ERK1 Y60C

<400> SEQUENCE: 23
gctcggcctg tgaccacgtg cgcaag                                          26
```

<210> SEQ ID NO 24
<211> LENGTH: 26
<212> TYPE: DNA
<213> ORGANISM: Artificial Sequence
<220> FEATURE:
<223> OTHER INFORMATION: GC - ERK1 Y60C

<400> SEQUENCE: 24
cttgcgcacg tggtcacagg ccgagc                                26

<210> SEQ ID NO 25
<211> LENGTH: 28
<212> TYPE: DNA
<213> ORGANISM: Artificial Sequence
<220> FEATURE:
<223> OTHER INFORMATION: ERK1 V63G

<400> SEQUENCE: 25
ctatgaccac gggcgcaaga ctcgcgtg                              28

<210> SEQ ID NO 26
<211> LENGTH: 28
<212> TYPE: DNA
<213> ORGANISM: Artificial Sequence
<220> FEATURE:
<223> OTHER INFORMATION: GC - ERK1 V63G

<400> SEQUENCE: 26
cacgcgagtc ttgcgcccgt ggtcatag                              28

<210> SEQ ID NO 27
<211> LENGTH: 27
<212> TYPE: DNA
<213> ORGANISM: Artificial Sequence
<220> FEATURE:
<223> OTHER INFORMATION: ERK1 K71R

<400> SEQUENCE: 27
cgcgtggcca tcaggaagat cagcccc                               27

<210> SEQ ID NO 28
<211> LENGTH: 27
<212> TYPE: DNA
<213> ORGANISM: Artificial Sequence
<220> FEATURE:
<223> OTHER INFORMATION: GC - ERK1 K71R

<400> SEQUENCE: 28
ggggctgatc ttcctgatgg ccacgcg                               27

<210> SEQ ID NO 29
<211> LENGTH: 34
<212> TYPE: DNA
<213> ORGANISM: Artificial Sequence
<220> FEATURE:
<223> OTHER INFORMATION: ERK1 S74G

<400> SEQUENCE: 29
catcaagaag atcggcccct tcgaacatca gacc                       34

<210> SEQ ID NO 30
<211> LENGTH: 34
<212> TYPE: DNA
<213> ORGANISM: Artificial Sequence
<220> FEATURE:

```
<223> OTHER INFORMATION: GC - ERK1 S74G

<400> SEQUENCE: 30
ggtctgatgt tcgaaggggc cgatcttctt gatg                              34

<210> SEQ ID NO 31
<211> LENGTH: 35
<212> TYPE: DNA
<213> ORGANISM: Artificial Sequence
<220> FEATURE:
<223> OTHER INFORMATION: ERK1 P75L

<400> SEQUENCE: 31
ccatcaagaa gatcagcctc ttcgaacatc agacc                             35

<210> SEQ ID NO 32
<211> LENGTH: 35
<212> TYPE: DNA
<213> ORGANISM: Artificial Sequence
<220> FEATURE:
<223> OTHER INFORMATION: GC - ERK1 P75L

<400> SEQUENCE: 32
ggtctgatgt tcgaagaggc tgatcttctt gatgg                             35

<210> SEQ ID NO 33
<211> LENGTH: 29
<212> TYPE: DNA
<213> ORGANISM: Artificial Sequence
<220> FEATURE:
<223> OTHER INFORMATION: ERK1 Y81C

<400> SEQUENCE: 33
cttcgaacat cagacctgct gccagcgca                                    29

<210> SEQ ID NO 34
<211> LENGTH: 30
<212> TYPE: DNA
<213> ORGANISM: Artificial Sequence
<220> FEATURE:
<223> OTHER INFORMATION: GC - ERK1 Y81C

<400> SEQUENCE: 34
gtgcgctggc agcaggtctg atgttcgaag                                   30

<210> SEQ ID NO 35
<211> LENGTH: 32
<212> TYPE: DNA
<213> ORGANISM: Artificial Sequence
<220> FEATURE:
<223> OTHER INFORMATION: ERK1 C82Y

<400> SEQUENCE: 35
cgaacatcag acctactacc agcgcacgct cc                                32

<210> SEQ ID NO 36
<211> LENGTH: 32
<212> TYPE: DNA
<213> ORGANISM: Artificial Sequence
<220> FEATURE:
<223> OTHER INFORMATION: GC - ERK1 C82Y

<400> SEQUENCE: 36
ggagcgtgcg ctggtagtag gtctgatgtt cg                                32
```

```
<210> SEQ ID NO 37
<211> LENGTH: 27
<212> TYPE: DNA
<213> ORGANISM: Artificial Sequence
<220> FEATURE:
<223> OTHER INFORMATION: ERK1 R84H

<400> SEQUENCE: 37
cagacctact gccagcacac gctccgg                                            27

<210> SEQ ID NO 38
<211> LENGTH: 27
<212> TYPE: DNA
<213> ORGANISM: Artificial Sequence
<220> FEATURE:
<223> OTHER INFORMATION: GC - ERK1 R84H

<400> SEQUENCE: 38
ccggagcgtg tgctggcagt aggtctg                                            27

<210> SEQ ID NO 39
<211> LENGTH: 28
<212> TYPE: DNA
<213> ORGANISM: Artificial Sequence
<220> FEATURE:
<223> OTHER INFORMATION: ERK1 Q90R

<400> SEQUENCE: 39
cacgctccgg gagatccgga tcctgctg                                           28

<210> SEQ ID NO 40
<211> LENGTH: 28
<212> TYPE: DNA
<213> ORGANISM: Artificial Sequence
<220> FEATURE:
<223> OTHER INFORMATION: GC - ERK1 Q90R

<400> SEQUENCE: 40
cagcaggatc cggatctccc ggagcgtg                                           28

<210> SEQ ID NO 41
<211> LENGTH: 33
<212> TYPE: DNA
<213> ORGANISM: Artificial Sequence
<220> FEATURE:
<223> OTHER INFORMATION: ERK1 Y148H

<400> SEQUENCE: 41
ccatatctgc tacttcctcc accagatcct gcg                                     33

<210> SEQ ID NO 42
<211> LENGTH: 33
<212> TYPE: DNA
<213> ORGANISM: Artificial Sequence
<220> FEATURE:
<223> OTHER INFORMATION: GC - ERK1 Y148H

<400> SEQUENCE: 42
cgcaggatct ggtggaggaa gtagcagata tgg                                     33

<210> SEQ ID NO 43
<211> LENGTH: 31
<212> TYPE: DNA
<213> ORGANISM: Artificial Sequence
<220> FEATURE:
<223> OTHER INFORMATION: ERK1 T176P
```

```
<400> SEQUENCE: 43
cctgctcatc aaccccacct gcgaccttaa g                              31

<210> SEQ ID NO 44
<211> LENGTH: 31
<212> TYPE: DNA
<213> ORGANISM: Artificial Sequence
<220> FEATURE:
<223> OTHER INFORMATION: GC - ERK1 T176P

<400> SEQUENCE: 44
cttaaggtcg caggtggggt tgatgagcag g                              31

<210> SEQ ID NO 45
<211> LENGTH: 31
<212> TYPE: DNA
<213> ORGANISM: Artificial Sequence
<220> FEATURE:
<223> OTHER INFORMATION: ERK1 T177P

<400> SEQUENCE: 45
cctgctcatc aacacccct gcgaccttaa g                               31

<210> SEQ ID NO 46
<211> LENGTH: 31
<212> TYPE: DNA
<213> ORGANISM: Artificial Sequence
<220> FEATURE:
<223> OTHER INFORMATION: GC - ERK1 T177P

<400> SEQUENCE: 46
cttaaggtcg caggggtgt tgatgagcag g                               31

<210> SEQ ID NO 47
<211> LENGTH: 32
<212> TYPE: DNA
<213> ORGANISM: Artificial Sequence
<220> FEATURE:
<223> OTHER INFORMATION: ERK1 G186D

<400> SEQUENCE: 47
gatttgtgat ttcgacctgg cccggattgc cg                             32

<210> SEQ ID NO 48
<211> LENGTH: 32
<212> TYPE: DNA
<213> ORGANISM: Artificial Sequence
<220> FEATURE:
<223> OTHER INFORMATION: GC - ERK1 G186D

<400> SEQUENCE: 48
cggcaatccg ggccaggtcg aaatcacaaa tc                             32

<210> SEQ ID NO 49
<211> LENGTH: 29
<212> TYPE: DNA
<213> ORGANISM: Artificial Sequence
<220> FEATURE:
<223> OTHER INFORMATION: ERK1 A206V

<400> SEQUENCE: 49
gacgggagta tgtggttacg cgctggtac                                 29

<210> SEQ ID NO 50
<211> LENGTH: 29
```

<212> TYPE: DNA
<213> ORGANISM: Artificial Sequence
<220> FEATURE:
<223> OTHER INFORMATION: GC - ERK1 A206V

<400> SEQUENCE: 50
gtaccagcgc gtaaccacat actcccgtc                                    29

<210> SEQ ID NO 51
<211> LENGTH: 34
<212> TYPE: DNA
<213> ORGANISM: Artificial Sequence
<220> FEATURE:
<223> OTHER INFORMATION: ERK1 M216I

<400> SEQUENCE: 51
cccagagatc attctgaact ccaagggcta tacc                              34

<210> SEQ ID NO 52
<211> LENGTH: 34
<212> TYPE: DNA
<213> ORGANISM: Artificial Sequence
<220> FEATURE:
<223> OTHER INFORMATION: GC - ERK1 M216I

<400> SEQUENCE: 52
ggtatagccc ttggagttca gaatgatctc tggg                              34

<210> SEQ ID NO 53
<211> LENGTH: 32
<212> TYPE: DNA
<213> ORGANISM: Artificial Sequence
<220> FEATURE:
<223> OTHER INFORMATION: ERK1 S219P

<400> SEQUENCE: 53
cagagatcat gctgaacccc aagggctata cc                                32

<210> SEQ ID NO 54
<211> LENGTH: 32
<212> TYPE: DNA
<213> ORGANISM: Artificial Sequence
<220> FEATURE:
<223> OTHER INFORMATION: GC - ERK1 S219P

<400> SEQUENCE: 54
ggtatagccc ttggggttca gcatgatctc tg                                32

<210> SEQ ID NO 55
<211> LENGTH: 31
<212> TYPE: DNA
<213> ORGANISM: Artificial Sequence
<220> FEATURE:
<223> OTHER INFORMATION: ERK1 A303V

<400> SEQUENCE: 55
gtcagactcc aaagtccttg acctgctgga c                                 31

<210> SEQ ID NO 56
<211> LENGTH: 31
<212> TYPE: DNA
<213> ORGANISM: Artificial Sequence
<220> FEATURE:
<223> OTHER INFORMATION: GC - ERK1 A303V

<400> SEQUENCE: 56
gtccagcagg tcaaggactt tggagtctga c                    31

<210> SEQ ID NO 57
<211> LENGTH: 28
<212> TYPE: DNA
<213> ORGANISM: Artificial Sequence
<220> FEATURE:
<223> OTHER INFORMATION: ERK1 Y329C

<400> SEQUENCE: 57 gctcaccct gcctggagca gtactatg                         28

<210> SEQ ID NO 58
<211> LENGTH: 28
<212> TYPE: DNA
<213> ORGANISM: Artificial Sequence
<220> FEATURE:
<223> OTHER INFORMATION: GC - ERK1 Y329C

<400> SEQUENCE: 58
catagtactg ctccaggcag gggtgagc                        28

<210> SEQ ID NO 59
<211> LENGTH: 29
<212> TYPE: DNA
<213> ORGANISM: Artificial Sequence
<220> FEATURE:
<223> OTHER INFORMATION: ERK1 D338N

<400> SEQUENCE: 59
actatgaccc gacgaatgag ccagtggcc                       29

<210> SEQ ID NO 60
<211> LENGTH: 29
<212> TYPE: DNA
<213> ORGANISM: Artificial Sequence
<220> FEATURE:
<223> OTHER INFORMATION: GC - ERK1 D338N

<400> SEQUENCE: 60
ggccactggc tcattcgtcg ggtcatagt                       29

<210> SEQ ID NO 61
<211> LENGTH: 28
<212> TYPE: DNA
<213> ORGANISM: Artificial Sequence
<220> FEATURE:
<223> OTHER INFORMATION: ERK1 E339K

<400> SEQUENCE: 61
gacccgacgg ataagccagt ggccgagg                        28

<210> SEQ ID NO 62
<211> LENGTH: 28
<212> TYPE: DNA
<213> ORGANISM: Artificial Sequence
<220> FEATURE:
<223> OTHER INFORMATION: GC - ERK1 E339K

<400> SEQUENCE: 62
cctcggccac tggcttatcc gtcgggtc                        28

<210> SEQ ID NO 63
<211> LENGTH: 27
<212> TYPE: DNA
<213> ORGANISM: Artificial Sequence

```
<220> FEATURE:
<223> OTHER INFORMATION: ERK1 T347A

<400> SEQUENCE: 63
gagcccttcg ccttcgccat ggagctg                                            27

<210> SEQ ID NO 64
<211> LENGTH: 27
<212> TYPE: DNA
<213> ORGANISM: Artificial Sequence
<220> FEATURE:
<223> OTHER INFORMATION: GC - ERK1 T347A

<400> SEQUENCE: 64
cagctccatg gcgaaggcga agggctc                                            27

<210> SEQ ID NO 65
<211> LENGTH: 36
<212> TYPE: DNA
<213> ORGANISM: Artificial Sequence
<220> FEATURE:
<223> OTHER INFORMATION: ERK2 'open'

<400> SEQUENCE: 65
ttccagccag gatacagatc tttgccaact ttcttg                                  36

<210> SEQ ID NO 66
<211> LENGTH: 36
<212> TYPE: DNA
<213> ORGANISM: Artificial Sequence
<220> FEATURE:
<223> OTHER INFORMATION: GC - ERK2 'open'

<400> SEQUENCE: 66
caagaaagtt ggcaaagatc tgtatcctgg ctggaa                                  36

<210> SEQ ID NO 67
<211> LENGTH: 25
<212> TYPE: DNA
<213> ORGANISM: Artificial Sequence
<220> FEATURE:
<223> OTHER INFORMATION: ERK2 Y36N

<400> SEQUENCE: 67
cgagggcgcc aacggcatgg tgtgc                                              25

<210> SEQ ID NO 68
<211> LENGTH: 25
<212> TYPE: DNA
<213> ORGANISM: Artificial Sequence
<220> FEATURE:
<223> OTHER INFORMATION: GC - ERK2 Y36N

<400> SEQUENCE: 68
gcacaccatg ccgttggcgc cctcg                                              25

<210> SEQ ID NO 69
<211> LENGTH: 25
<212> TYPE: DNA
<213> ORGANISM: Artificial Sequence
<220> FEATURE:
<223> OTHER INFORMATION: ERK2 Y36H

<400> SEQUENCE: 69
cgagggcgcc cacggcatgg tgtgc                                              25
```

```
<210> SEQ ID NO 70
<211> LENGTH: 25
<212> TYPE: DNA
<213> ORGANISM: Artificial Sequence
<220> FEATURE:
<223> OTHER INFORMATION: GC - ERK2 Y36H

<400> SEQUENCE: 70
gcacaccatg ccgtgggcgc cctcg                                  25

<210> SEQ ID NO 71
<211> LENGTH: 28
<212> TYPE: DNA
<213> ORGANISM: Artificial Sequence
<220> FEATURE:
<223> OTHER INFORMATION: ERK2 G37S

<400> SEQUENCE: 71
gagggcgcct acagcatggt gtgctctg                               28

<210> SEQ ID NO 72
<211> LENGTH: 28
<212> TYPE: DNA
<213> ORGANISM: Artificial Sequence
<220> FEATURE:
<223> OTHER INFORMATION: GC - ERK2 G37S

<400> SEQUENCE: 72
cagagcacac catgctgtag gcgccctc                               28

<210> SEQ ID NO 73
<211> LENGTH: 39
<212> TYPE: DNA
<213> ORGANISM: Artificial Sequence
<220> FEATURE:
<223> OTHER INFORMATION: ERK2 K54R

<400> SEQUENCE: 73
aaagttcgag tagctatcag gaaaatcagc ccctttgag                   39

<210> SEQ ID NO 74
<211> LENGTH: 39
<212> TYPE: DNA
<213> ORGANISM: Artificial Sequence
<220> FEATURE:
<223> OTHER INFORMATION: GC - ERK2 K54R

<400> SEQUENCE: 74
ctcaaagggg ctgattttcc tgatagctac tcgaacttt                   39

<210> SEQ ID NO 75
<211> LENGTH: 36
<212> TYPE: DNA
<213> ORGANISM: Artificial Sequence
<220> FEATURE:
<223> OTHER INFORMATION: ERK2 P58T

<400> SEQUENCE: 75
gctatcaaga aaatcagcac ctttgagcac cagacc                      36

<210> SEQ ID NO 76
<211> LENGTH: 36
<212> TYPE: DNA
<213> ORGANISM: Artificial Sequence
<220> FEATURE:
<223> OTHER INFORMATION: GC - ERK2 P58T
```

-continued

```
<400> SEQUENCE: 76
ggtctggtgc tcaaaggtgc tgattttctt gatagc                                 36

<210> SEQ ID NO 77
<211> LENGTH: 36
<212> TYPE: DNA
<213> ORGANISM: Artificial Sequence
<220> FEATURE:
<223> OTHER INFORMATION: ERK2 P58S

<400> SEQUENCE: 77
gctatcaaga aaatcagctc ctttgagcac cagacc                                 36

<210> SEQ ID NO 78
<211> LENGTH: 34
<212> TYPE: DNA
<213> ORGANISM: Artificial Sequence
<220> FEATURE:
<223> OTHER INFORMATION: GC - ERK2 P58S

<400> SEQUENCE: 78
ggtctggtgc tcaaaggagc tgattttctt gata                                   34

<210> SEQ ID NO 79
<211> LENGTH: 28
<212> TYPE: DNA
<213> ORGANISM: Artificial Sequence
<220> FEATURE:
<223> OTHER INFORMATION: ERK2 Y64N

<400> SEQUENCE: 79
gcaccagacc aactgccaga gaaccctg                                          28

<210> SEQ ID NO 80
<211> LENGTH: 28
<212> TYPE: DNA
<213> ORGANISM: Artificial Sequence
<220> FEATURE:
<223> OTHER INFORMATION: GC - ERK2 Y64N

<400> SEQUENCE: 80
cagggttctc tggcagttgg tctggtgc                                          28

<210> SEQ ID NO 81
<211> LENGTH: 32
<212> TYPE: DNA
<213> ORGANISM: Artificial Sequence
<220> FEATURE:
<223> OTHER INFORMATION: ERK2 C65Y

<400> SEQUENCE: 81
gagcaccaga cctactacca gagaaccctg ag                                     32

<210> SEQ ID NO 82
<211> LENGTH: 32
<212> TYPE: DNA
<213> ORGANISM: Artificial Sequence
<220> FEATURE:
<223> OTHER INFORMATION: GC - ERK2 C65Y

<400> SEQUENCE: 82
ctcagggttc tctggtagta ggtctggtgc tc                                     32

<210> SEQ ID NO 83
```

```
<211> LENGTH: 29
<212> TYPE: DNA
<213> ORGANISM: Artificial Sequence
<220> FEATURE:
<223> OTHER INFORMATION: ERK2 V39G

<400> SEQUENCE: 83
cgcctacggc atgggtgct ctgcttatg                                         29

<210> SEQ ID NO 84
<211> LENGTH: 29
<212> TYPE: DNA
<213> ORGANISM: Artificial Sequence
<220> FEATURE:
<223> OTHER INFORMATION: GC - ERK2 V39G

<400> SEQUENCE: 84
cataagcaga gcaccccatg ccgtaggcg                                        29

<210> SEQ ID NO 85
<211> LENGTH: 36
<212> TYPE: DNA
<213> ORGANISM: Artificial Sequence
<220> FEATURE:
<223> OTHER INFORMATION: ERK2 P58L

<400> SEQUENCE: 85
gctatcaaga aaatcagcct ctttgagcac cagacc                                36

<210> SEQ ID NO 86
<211> LENGTH: 36
<212> TYPE: DNA
<213> ORGANISM: Artificial Sequence
<220> FEATURE:
<223> OTHER INFORMATION: GC - ERK2 P58L

<400> SEQUENCE: 86
ggtctggtgc tcaaagaggc tgattttctt gatagc                                36

<210> SEQ ID NO 87
<211> LENGTH: 31
<212> TYPE: DNA
<213> ORGANISM: Artificial Sequence
<220> FEATURE:
<223> OTHER INFORMATION: ERK2 R67K

<400> SEQUENCE: 87
ccagacctac tgccagaaaa ccctgaggga g                                     31

<210> SEQ ID NO 88
<211> LENGTH: 31
<212> TYPE: DNA
<213> ORGANISM: Artificial Sequence
<220> FEATURE:
<223> OTHER INFORMATION: GC - ERK2 R67K

<400> SEQUENCE: 88
ctccctcagg gttttctggc agtaggtctg g                                     31

<210> SEQ ID NO 89
<211> LENGTH: 45
<212> TYPE: DNA
<213> ORGANISM: Artificial Sequence
<220> FEATURE:
<223> OTHER INFORMATION: ERK2 Q105A

<400> SEQUENCE: 89
```
ccatcgagca aatgaaagat gtatatatag tagcggacct catgg                45

<210> SEQ ID NO 90
<211> LENGTH: 45
<212> TYPE: DNA
<213> ORGANISM: Artificial Sequence
<220> FEATURE:
<223> OTHER INFORMATION: GC - ERK2 Q105A

<400> SEQUENCE: 90
ccatgaggtc cgctactata tatacatctt tcatttgctc gatgg                45

<210> SEQ ID NO 91
<211> LENGTH: 32
<212> TYPE: DNA
<213> ORGANISM: Artificial Sequence
<220> FEATURE:
<223> OTHER INFORMATION: ERK2 H120P

<400> SEQUENCE: 91
gctcttgaag acacaacccc tcagcaatga cc                              32

<210> SEQ ID NO 92
<211> LENGTH: 32
<212> TYPE: DNA
<213> ORGANISM: Artificial Sequence
<220> FEATURE:
<223> OTHER INFORMATION: GC - ERK2 H120P

<400> SEQUENCE: 92
ggtcattgct gaggggttgt gtcttcaaga gc                              32

<210> SEQ ID NO 93
<211> LENGTH: 39
<212> TYPE: DNA
<213> ORGANISM: Artificial Sequence
<220> FEATURE:
<223> OTHER INFORMATION: ERK2 Y131F

<400> SEQUENCE: 93
gaccatatct gctattttct cttccagatc ctcagaggg                       39

<210> SEQ ID NO 94
<211> LENGTH: 39
<212> TYPE: DNA
<213> ORGANISM: Artificial Sequence
<220> FEATURE:
<223> OTHER INFORMATION: GC - ERK2 Y131F

<400> SEQUENCE: 94
ccctctgagg atctggaaga gaaaatagca gatatggtc                       39

<210> SEQ ID NO 95
<211> LENGTH: 31
<212> TYPE: DNA
<213> ORGANISM: Artificial Sequence
<220> FEATURE:
<223> OTHER INFORMATION: ERK2 T159P

<400> SEQUENCE: 95
cctgctgctc aaccccacct gtgatctcaa g                               31

<210> SEQ ID NO 96
<211> LENGTH: 31
<212> TYPE: DNA

```
<213> ORGANISM: Artificial Sequence
<220> FEATURE:
<223> OTHER INFORMATION: GC - ERK2 T159P

<400> SEQUENCE: 96
cttgagatca caggtggggt tgagcagcag g                             31

<210> SEQ ID NO 97
<211> LENGTH: 30
<212> TYPE: DNA
<213> ORGANISM: Artificial Sequence
<220> FEATURE:
<223> OTHER INFORMATION: ERK2 T160P

<400> SEQUENCE: 97
gctgctcaac accccctgtg atctcaagat                               30

<210> SEQ ID NO 98
<211> LENGTH: 31
<212> TYPE: DNA
<213> ORGANISM: Artificial Sequence
<220> FEATURE:
<223> OTHER INFORMATION: GC - ERK2 T160P

<400> SEQUENCE: 98
gatcttgaga tcacaggggg tgttgagcag c                             31

<210> SEQ ID NO 99
<211> LENGTH: 36
<212> TYPE: DNA
<213> ORGANISM: Artificial Sequence
<220> FEATURE:
<223> OTHER INFORMATION: ERK2 V214A

<400> SEQUENCE: 99
ccattgatat ttggtctgca ggctgcattc tggcag                        36

<210> SEQ ID NO 100
<211> LENGTH: 35
<212> TYPE: DNA
<213> ORGANISM: Artificial Sequence
<220> FEATURE:
<223> OTHER INFORMATION: GC - ERK2 V214A

<400> SEQUENCE: 100
ctgccagaat gcagcctgca gaccaaatat caatg                         35

<210> SEQ ID NO 101
<211> LENGTH: 29
<212> TYPE: DNA
<213> ORGANISM: Artificial Sequence
<220> FEATURE:
<223> OTHER INFORMATION: ERK2 D321G

<400> SEQUENCE: 101
gtattacgac ccgagtggcg agcccatcg                                29

<210> SEQ ID NO 102
<211> LENGTH: 29
<212> TYPE: DNA
<213> ORGANISM: Artificial Sequence
<220> FEATURE:
<223> OTHER INFORMATION: GC - ERK2 D321G

<400> SEQUENCE: 102
cgatgggctc gccactcggg tcgtaatac                                29
```

<210> SEQ ID NO 103
<211> LENGTH: 33
<212> TYPE: DNA
<213> ORGANISM: Artificial Sequence
<220> FEATURE:
<223> OTHER INFORMATION: ERK2 D321N

<400> SEQUENCE: 103
gagcagtatt acgacccgag taacgagccc atc                                    33

<210> SEQ ID NO 104
<211> LENGTH: 33
<212> TYPE: DNA
<213> ORGANISM: Artificial Sequence
<220> FEATURE:
<223> OTHER INFORMATION: GC - ERK2 D321N

<400> SEQUENCE: 104
gatgggctcg ttactcgggt cgtaatactg ctc                                    33

<210> SEQ ID NO 105
<211> LENGTH: 30
<212> TYPE: DNA
<213> ORGANISM: Artificial Sequence
<220> FEATURE:
<223> OTHER INFORMATION: ERK2 E322K

<400> SEQUENCE: 105
cgacccgagt gacaagccca tcgccgaagc                                        30

<210> SEQ ID NO 106
<211> LENGTH: 30
<212> TYPE: DNA
<213> ORGANISM: Artificial Sequence
<220> FEATURE:
<223> OTHER INFORMATION: GC - ERK2 E322K

<400> SEQUENCE: 106
gcttcggcga tgggcttgtc actcgggtcg                                        30

<210> SEQ ID NO 107
<211> LENGTH: 28
<212> TYPE: DNA
<213> ORGANISM: Artificial Sequence
<220> FEATURE:
<223> OTHER INFORMATION: ERK2 P323S

<400> SEQUENCE: 107
cgagtgacga gtccatcgcc gaagcacc                                          28

<210> SEQ ID NO 108
<211> LENGTH: 28
<212> TYPE: DNA
<213> ORGANISM: Artificial Sequence
<220> FEATURE:
<223> OTHER INFORMATION: GC - ERK2 P323S

<400> SEQUENCE: 108
ggtgcttcgg cgatggactc gtcactcg                                          28

<210> SEQ ID NO 109
<211> LENGTH: 42
<212> TYPE: DNA
<213> ORGANISM: Artificial Sequence
<220> FEATURE:

<223> OTHER INFORMATION: ERK2 V104V

<400> SEQUENCE: 109
gcaaatgaaa gatgtatata tagtgcagga cctcatggaa ac  42

<210> SEQ ID NO 110
<211> LENGTH: 42
<212> TYPE: DNA
<213> ORGANISM: Artificial Sequence
<220> FEATURE:
<223> OTHER INFORMATION: GC - ERK2 V104V

<400> SEQUENCE: 110
gtttccatga ggtcctgcac tatatataca tctttcattt gc  42

<210> SEQ ID NO 111
<211> LENGTH: 33
<212> TYPE: DNA
<213> ORGANISM: Artificial Sequence
<220> FEATURE:
<223> OTHER INFORMATION: ERK2 A189V

<400> SEQUENCE: 111
gacagaatat gtggtcacac gttggtacag ggc  33

<210> SEQ ID NO 112
<211> LENGTH: 33
<212> TYPE: DNA
<213> ORGANISM: Artificial Sequence
<220> FEATURE:
<223> OTHER INFORMATION: GC - ERK2 A189V

<400> SEQUENCE: 112
gccctgtacc aacgtgtgac cacatattct gtc  33

<210> SEQ ID NO 113
<211> LENGTH: 36
<212> TYPE: DNA
<213> ORGANISM: Artificial Sequence
<220> FEATURE:
<223> OTHER INFORMATION: ERK2 S202P

<400> SEQUENCE: 113
ccagaaatta tgttgaatcc caagggctac accaag  36

<210> SEQ ID NO 114
<211> LENGTH: 36
<212> TYPE: DNA
<213> ORGANISM: Artificial Sequence
<220> FEATURE:
<223> OTHER INFORMATION: GC - ERK2 S202P

<400> SEQUENCE: 114
cttggtgtag cccttgggat tcaacataat ttctgg  36

<210> SEQ ID NO 115
<211> LENGTH: 39
<212> TYPE: DNA
<213> ORGANISM: Artificial Sequence
<220> FEATURE:
<223> OTHER INFORMATION: ERK2 Y205N

<400> SEQUENCE: 115
gttgaattcc aagggcaaca ccaagtccat tgatatttg  39

```
<210> SEQ ID NO 116
<211> LENGTH: 39
<212> TYPE: DNA
<213> ORGANISM: Artificial Sequence
<220> FEATURE:
<223> OTHER INFORMATION: GC - ERK2 Y205N

<400> SEQUENCE: 116
caaatatcaa tggacttggt gttgcccttg gaattcaac                          39
```